US008383372B2

(12) United States Patent
Nonaka et al.

(10) Patent No.: US 8,383,372 B2

(45) Date of Patent: Feb. 26, 2013

(54) L-CYSTEINE PRODUCING BACTERIUM AND A METHOD FOR PRODUCING L-CYSTEINE

(75) Inventors: Gen Nonaka, Kawasaki (JP); Kazuhiro Takumi, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 830 days.

(21) Appl. No.: 12/397,683

(22) Filed: Mar. 4, 2009

(65) Prior Publication Data

US 2009/0226984 A1 Sep. 10, 2009

(30) Foreign Application Priority Data

Mar. 6, 2008 (JP) ................................ 2008-056371

(51) Int. Cl.
*C12P 13/12* (2006.01)
*C12N 1/00* (2006.01)
*C12N 1/20* (2006.01)

(52) U.S. Cl. ..................... 435/113; 435/243; 435/252.1; 435/252.3

(58) Field of Classification Search .................. 435/113
See application file for complete search history.

(56) References Cited

U.S. PATENT DOCUMENTS 5,618,716 A 4/1997 Burlingame
5,856,148 A 1/1999 Burlingame
5,972,663 A 10/1999 Winterhalter et al.
6,218,168 B1 4/2001 Leinfelder et al.
7,148,047 B2 * 12/2006 Takagi et al. ................ 435/193
7,348,037 B2 3/2008 Buchholz et al.
8,008,048 B2 * 8/2011 Nonaka et al. ............... 435/113
2003/0077766 A1 4/2003 Takagi et al.
2003/0186393 A1 10/2003 Takagi et al.
2004/0038352 A1 2/2004 Maier
2005/0009162 A1 1/2005 Maier et al.
2005/0112731 A1 5/2005 Kashiwagi et al.
2005/0124049 A1 6/2005 Ziyatdinov et al.
2005/0221453 A1 10/2005 Takagi et al.
2008/0076163 A1 3/2008 Takagi et al.

FOREIGN PATENT DOCUMENTS

CA 2386539 4/2007
JP 11-155571 6/1999
JP 2002-233384 8/2002
JP 2003-169668 6/2003
JP 2005-245311 9/2005
JP 2005-287333 10/2005
WO WO01/27307 4/2001
WO WO 2008/010565 * 1/2008

OTHER PUBLICATIONS

Database UniProt [Online], Database Accession No. A8AK06, pp. 1-2.

(Continued)

*Primary Examiner* — Ruth Davis
*Assistant Examiner* — Sheridan Macauley
(74) *Attorney, Agent, or Firm* — Shelley Guest Cermak; Cermak Nakajima LLP

(57) ABSTRACT

The present invention describes a bacterium belonging to the family *Enterobacteriaceae* which has L-cysteine-producing ability and has been modified to decrease the activity of a protein encoded by the d0191 gene. This bacterium is cultured in a medium, and L-cysteine, L-cystine, derivatives thereof, or a mixture thereof is collected from the medium.

7 Claims, 10 Drawing Sheets

TERrrnB
KpnI
cat
HindIII
KpnI
Red-tL3
PlacUV5
sacB
Hin dIII
lacI
RSF-Red-TER
12568 bp
PlacUV5

OTHER PUBLICATIONS

Denk, D., et al., "L-Cysteine Biosynthesis in *Escherichia coli*: Nucleotide Sequence and Expression of the Serine Acetyltransferase (*cysE*) Gene from the Wild-type and a Cysteine-excreting Mutant," J. Gen. Microbiol. 1987;133:515-525.

Takagi, H., et al., "Overproduction of L-Cysteine and L-Cystine by expression of genes for feedback inhibition-insensitive serine acetyltransferase from *Arabidopsis thaliana* in *Escherichia coli*," FEMS Microbiol. Lett. 1999;179:453-459.

Wada, M., et al., "Metabolic pathways and biotechnological production of L-cysteine," Appl. Microbiol. Biotechnol. 2006;73:48-54.

Yamada, S., et al., "Effect of Drug Transporter Genes on Cysteine Export and Overproduction in *Escherichia coli*," Appl. Environmen. Microbiol. 2006;72(7):4735-4742.

European Search Report for European Patent App. No. 09003107.1 (Nov. 11, 2009).

Awano, N., et al., "Effect of cysteine desulthydrase gene disruption on L-cysteine overproduction in *Escherichia coli*," Appl. Microbiol. Biotechnol. 2003;62:239-243.

Awano, N., et al., "Identification and Functional Analysis of *Escherichia coli* Cysteine Desulfhydrases," Appl. Environmen. Microbiol. 2005;71(7):4149-4152.

Daβler, T., et al., "Identification of a major facilitator protein from *Escherichia coli* involved in efflux of metabolites of the cysteine pathway," Molecular Microbiol. 2000;36(5):1101-1112.

Dominy, J. E., et al., "Identification and Characterization of Bacterial Cysteine Dioxygenases: a New Route of Cysteine Degradation for Eubacteria," J. Bacteriol. 2006;188(15):5561-5569.

Flatley, J., et al., "Transcriptional Responses of *Escherichia coli* to S-Nitrosoglutathione under Defined Chemostat Conditions Reveal Major Changes in Methionine Biosynthesis," J. Biol. Chem. 2005;280(11):10065-10072.

Pae, K. M., et at., "Kinetic Properties of a L-Cysteine Desulfhydrase-Deficient Mutant in the Enzymatic Formation of L-Cysteine from D,L-ATC," Biotechnol. Lett. 1992;14(12):1143-1148.

Soutourina, J., et al., "Role of D-Cysteine Desulfhydrase in the Adaptation of *Escherichia coli* to D-Cysteine," J. Biol. Chem. 2001;276(44):40864-40872.

Tchong, S-I., et al., "L-Cysteine Desulfidase: An [4Fe-4S] Enzyme Isolated from *Methanocaldococcus jannaschli* That Catalyzes the Breakdown of L-Cysteine into Pyruvate, Ammonia, and Sulfide," Biochem. 2005;44(5):1659-1670.

Wada, M., et al., "Purification, characterization and identification of cysteine desultbydrase of *Corynebacterium glutamicum*, and its relationship to cysteine production," FEMS Microbiol. Lett. 2002;217:103-107.

Zdych, E., et al., "MalY of *Escherichia coli* Is an Enzyme with the Activity of a βC-S Lyase (Cystathionase)," J. Bacteriol. 1995; I 77(17):5035-5039.

* cited by examiner lane 1: SC17 lane 2: SC17 d0191::Km$^r$ lane 3: SC17/pHSG299 lane 4: SC17/pHSG-d0191

SEQUENCE LISTING

```
<160> NUMBER OF SEQ ID NOS: 67

<210> SEQ ID NO 1
<211> LENGTH: 1035
<212> TYPE: DNA
<213> ORGANISM: Pantoea ananatis
<220> FEATURE:
<221> NAME/KEY: CDS
<222> LOCATION: (1)..(1035)

<400> SEQUENCE: 1

atg tca aca tgc tgg gta cgc cac gcg att aac gaa att aac gct gat       48
Met Ser Thr Cys Trp Val Arg His Ala Ile Asn Glu Ile Asn Ala Asp
1               5                   10                  15

ttt caa cgc tca gcg gac aca cac tta att cgc ttc agt ttg ccg gat       96
Phe Gln Arg Ser Ala Asp Thr His Leu Ile Arg Phe Ser Leu Pro Asp
            20                  25                  30

ttt ccg ggc atc agg ttc tat ctc aaa gat gaa agc acg cat ccc agc      144
Phe Pro Gly Ile Arg Phe Tyr Leu Lys Asp Glu Ser Thr His Pro Ser
        35                  40                  45

gga agt ctg aaa cat cgt ctg gcg cgc tct ctg ttt ctg tac gcc ctg      192
Gly Ser Leu Lys His Arg Leu Ala Arg Ser Leu Phe Leu Tyr Ala Leu
    50                  55                  60

gcc aac ggt tgg atc aaa caa gat aca ccg gtt att gag gca tct tcg      240
Ala Asn Gly Trp Ile Lys Gln Asp Thr Pro Val Ile Glu Ala Ser Ser
65                  70                  75                  80

ggc agt acg gcc gtg tct gaa gcc tat ttt gcc cgc ctg ctg ggc ttg      288
Gly Ser Thr Ala Val Ser Glu Ala Tyr Phe Ala Arg Leu Leu Gly Leu
                85                  90                  95

cct ttt att gcc gtc atg ccc gcc agc acc gcg aag cgt aaa att gag      336
Pro Phe Ile Ala Val Met Pro Ala Ser Thr Ala Lys Arg Lys Ile Glu
            100                 105                 110
```

```
cag atc acc ttt tac ggc ggt cag tgt cac ttt gtc agc gat ccc tgt      384
Gln Ile Thr Phe Tyr Gly Gly Gln Cys His Phe Val Ser Asp Pro Cys
        115                 120                 125

cag ctc tat gca gaa tcc gag cgc ctc gcc cgg gaa ctg aac ggc cat      432
Gln Leu Tyr Ala Glu Ser Glu Arg Leu Ala Arg Glu Leu Asn Gly His
    130                 135                 140

ttt atg gat cag ttt acc tac gcg gaa cgg gcc acc gac tgg cgc ggc      480
Phe Met Asp Gln Phe Thr Tyr Ala Glu Arg Ala Thr Asp Trp Arg Gly
145                 150                 155                 160

aac aac aac att gct gaa agc atc ttc cgt cag atg gca aac gaa ccc      528
Asn Asn Asn Ile Ala Glu Ser Ile Phe Arg Gln Met Ala Asn Glu Pro
                165                 170                 175

ttt ccc gtt cct cac acc ctg att atg agt gcc ggc act ggc ggt acc      576
Phe Pro Val Pro His Thr Leu Ile Met Ser Ala Gly Thr Gly Gly Thr
            180                 185                 190

tcg gcc acg ctg gga cgc tat att cgc tat cag gga tgc gat acg cga      624
Ser Ala Thr Leu Gly Arg Tyr Ile Arg Tyr Gln Gly Cys Asp Thr Arg
        195                 200                 205

tta ctg gtc gtt gat ccg cag cat tcc gtt ttt tat gac tac tgg cac      672
Leu Leu Val Val Asp Pro Gln His Ser Val Phe Tyr Asp Tyr Trp His
    210                 215                 220

aac cgt gac gcc acc ctg acc agc aat cgt ggc agc atg att gaa ggc      720
Asn Arg Asp Ala Thr Leu Thr Ser Asn Arg Gly Ser Met Ile Glu Gly
225                 230                 235                 240

att ggt cgt cca cgc gtc gag cct tcc ttt atg ccc gat gtg att gac      768
Ile Gly Arg Pro Arg Val Glu Pro Ser Phe Met Pro Asp Val Ile Asp
                245                 250                 255

gaa atg ctt cgc gta ccg gat ggc gca tca att gcc gcc atg ctg aag      816
Glu Met Leu Arg Val Pro Asp Gly Ala Ser Ile Ala Ala Met Leu Lys
            260                 265                 270

ctg gaa acg ctg ctg gga cgc aaa ccg ggc ccg tct acc ggc acc aac      864
Leu Glu Thr Leu Leu Gly Arg Lys Pro Gly Pro Ser Thr Gly Thr Asn
        275                 280                 285

ttc tgg ggc atg atg cag gtg gca aaa cgc tta cgc gat aac cac gag      912
Phe Trp Gly Met Met Gln Val Ala Lys Arg Leu Arg Asp Asn His Glu
    290                 295                 300

cag ggc tcg ctg gtg aca ctg ctg tgc gac agc gga gaa cgt tat cct      960
Gln Gly Ser Leu Val Thr Leu Leu Cys Asp Ser Gly Glu Arg Tyr Pro
305                 310                 315                 320

gat act tac tat caa cct gag tgg gtt gcc gag cac att ggc gat att     1008
Asp Thr Tyr Tyr Gln Pro Glu Trp Val Ala Glu His Ile Gly Asp Ile
                325                 330                 335

acg ccc tgg cag cgc gaa ctg ggc tag                                 1035
Thr Pro Trp Gln Arg Glu Leu Gly
            340


<210> SEQ ID NO 2
<211> LENGTH: 344
<212> TYPE: PRT
<213> ORGANISM: Pantoea ananatis

<400> SEQUENCE: 2

Met Ser Thr Cys Trp Val Arg His Ala Ile Asn Glu Ile Asn Ala Asp
1               5                   10                  15

Phe Gln Arg Ser Ala Asp Thr His Leu Ile Arg Phe Ser Leu Pro Asp
            20                  25                  30

Phe Pro Gly Ile Arg Phe Tyr Leu Lys Asp Glu Ser Thr His Pro Ser
        35                  40                  45

Gly Ser Leu Lys His Arg Leu Ala Arg Ser Leu Phe Leu Tyr Ala Leu
    50                  55                  60
```

```
Ala Asn Gly Trp Ile Lys Gln Asp Thr Pro Val Ile Glu Ala Ser Ser
65                  70                  75                  80

Gly Ser Thr Ala Val Ser Glu Ala Tyr Phe Ala Arg Leu Leu Gly Leu
                85                  90                  95

Pro Phe Ile Ala Val Met Pro Ala Ser Thr Ala Lys Arg Lys Ile Glu
            100                 105                 110

Gln Ile Thr Phe Tyr Gly Gly Gln Cys His Phe Val Ser Asp Pro Cys
        115                 120                 125

Gln Leu Tyr Ala Glu Ser Glu Arg Leu Ala Arg Glu Leu Asn Gly His
    130                 135                 140

Phe Met Asp Gln Phe Thr Tyr Ala Glu Arg Ala Thr Asp Trp Arg Gly
145                 150                 155                 160

Asn Asn Asn Ile Ala Glu Ser Ile Phe Arg Gln Met Ala Asn Glu Pro
                165                 170                 175

Phe Pro Val Pro His Thr Leu Ile Met Ser Ala Gly Thr Gly Gly Thr
            180                 185                 190

Ser Ala Thr Leu Gly Arg Tyr Ile Arg Tyr Gln Gly Cys Asp Thr Arg
        195                 200                 205

Leu Leu Val Val Asp Pro Gln His Ser Val Phe Tyr Asp Tyr Trp His
    210                 215                 220

Asn Arg Asp Ala Thr Leu Thr Ser Asn Arg Gly Ser Met Ile Glu Gly
225                 230                 235                 240

Ile Gly Arg Pro Arg Val Glu Pro Ser Phe Met Pro Asp Val Ile Asp
                245                 250                 255

Glu Met Leu Arg Val Pro Asp Gly Ala Ser Ile Ala Ala Met Leu Lys
            260                 265                 270

Leu Glu Thr Leu Leu Gly Arg Lys Pro Gly Pro Ser Thr Gly Thr Asn
        275                 280                 285

Phe Trp Gly Met Met Gln Val Ala Lys Arg Leu Arg Asp Asn His Glu
    290                 295                 300

Gln Gly Ser Leu Val Thr Leu Leu Cys Asp Ser Gly Glu Arg Tyr Pro
305                 310                 315                 320

Asp Thr Tyr Tyr Gln Pro Glu Trp Val Ala Glu His Ile Gly Asp Ile
                325                 330                 335

Thr Pro Trp Gln Arg Glu Leu Gly
            340
```

<210> SEQ ID NO 3
<211> LENGTH: 1308
<212> TYPE: DNA
<213> ORGANISM: Pantoea ananatis

<400> SEQUENCE: 3

```
atgagcagaa tcatgacgcc cgtgaactgg gaagcctgca gcagcgaggc gcagcaggcg      60

ctgttggcac gccctgcgct cgcctcgtct gacagcatca gccagatcgt gcgcgatgtg     120

ttggtcagag tgaaagagga aggcgatgcg gctttacgag aattcagcgc gcgctttgac     180

aaggttgaaa cagacgacct gcgcgttacg ccacagcaga tgcaggcggc cagcgatcgc     240

cttggtgacg agctgaaaca ggcgatggcc gtggccattg gcaatattga aacctttcac     300

cgtgcgcaga tcctgccgcc ggtggatgtg gaaacgcagc ccggcgtgcg ctgtcagcaa     360

attacgcgcc cgatgaaatc ggtgggcttg tatattccgg gcggttctgc cccgctgttt     420

tctaccgttc tgatgctggc taccccggcg cggattgcgg gctgtggtcg cgtggtgctg     480

tgctcgcccc cgccgattgc tgatgaaatt ctctacgcgg ccaaactttg cggtgtggaa     540
```

```
gaagtgttcc aggtgggtgg atcacaggcg attgccgccc tggcttttgg caccgaaagc    600

atccctaagg tagataaaat ttttggtccg ggcaacgcgt gggttaccga agccaaacgt    660

caggtcagcc agcgccttga tggcgcggcg attgatatgc ccgctggccc gtcggaagtg    720

ctggtgattg ccgatgaagg tgccacaccg gccttcgttg cctctgatct gctgtcgcag    780

gcggaacacg gccctgactc gcaggtgatt ttactgacgc cttcgctggc gctggccgag    840

cgcgtcgccg aggcggtgga ggatcagctg gcccagttgc cacgtgcggc gacagcccgc    900

caggcactgg aaagcagccg cctgatcgtc gcccgggata tgcagcaatg cattgcgatc    960

tccaaccgct atggtccgga gcacctgatt ctgcaaaccc gcacgccacg ggatctggtg   1020

gaacagatta ccagcgccgg ttcggttttc ctgggcgact ggtcaccgga atccgcagga   1080

gattatgctt cgggcaccaa ccacgtgctg ccgacctacg gctataccgc gacatgctcc   1140

agcctgggcc tggccgactt tcagaaacgc atgacggtac aggagctgac gccgcagggc   1200

ttcctgaacc tggcggcgac catcgaaacc ctggcggccg ctgaacagct gcacgcccac   1260

aaaaatgccg tcacgttgcg cgttgccgca ctcaaggagc aagcatga                1308
```

<210> SEQ ID NO 4
<211> LENGTH: 68
<212> TYPE: DNA
<213> ORGANISM: Artificial Sequence
<220> FEATURE:
<223> OTHER INFORMATION: primer

<400> SEQUENCE: 4

```
ccatagcggt tggagatcgc aatgcattgc tgcatatccc tgaagcctgc ttttttatac     60

taagttgg                                                              68
```

<210> SEQ ID NO 5
<211> LENGTH: 68
<212> TYPE: DNA
<213> ORGANISM: Artificial Sequence
<220> FEATURE:
<223> OTHER INFORMATION: primer

<400> SEQUENCE: 5

```
gcccgccagg cactggaaag cagccgcctg atcgtcgccc cgctcaagtt agtataaaaa     60

agctgaac                                                              68
```

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6

```
tagcgagatc tctgatgtcc ggcggtgctt ttg                                  33
```

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7

```
aaaaagagct cttacgcccc gccctgccac tc                                   32
```

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
caggatctag aaggagacat gaacgatgaa catc 34

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9
gataaggatc cgaaataaaa gaaaatgcca atagga 36

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
cctttgagct cgcgggcagt gagcgcaacg c 31

<210> SEQ ID NO 11
<211> LENGTH: 48
<212> TYPE: DNA
<213> ORGANISM: Artificial Sequence
<220> FEATURE:
<223> OTHER INFORMATION: primer

<400> SEQUENCE: 11
ctagagcggc cgccgatcgg gatcctcctg tgtgaaattg ttatccgc 48

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
ctctacgatc gaggaggtta taaaaaatgg atattaatac tg 42

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
tcaaagcggc cgcttcttcg tctgtttcta ctggta 36

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14

```
cctttggtac cgcgggcagt gagcgcaacg c                                  31


<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15

aacaggaatt ctttgcctgg cggcagtagc gcgg                               34


<210> SEQ ID NO 16
<211> LENGTH: 34
<212> TYPE: DNA
<213> ORGANISM: Artificial Sequence
<220> FEATURE:
<223> OTHER INFORMATION: primer

<400> SEQUENCE: 16

cgcggatcca agcttttcat tatccagcag agcg                               34


<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17

cgcggatcct aatgctgtag ggcctgaacc ag                                 32


<210> SEQ ID NO 18
<211> LENGTH: 80
<212> TYPE: DNA
<213> ORGANISM: Artificial Sequence
<220> FEATURE:
<223> OTHER INFORMATION: primer

<400> SEQUENCE: 18

ccgtgtctga agcctatttt gcccgcctgc tgggcttgcc ttttattgcc tgaagcctgc   60

tttttatac taagttggca                                                80


<210> SEQ ID NO 19
<211> LENGTH: 80
<212> TYPE: DNA
<213> ORGANISM: Artificial Sequence
<220> FEATURE:
<223> OTHER INFORMATION: primer

<400> SEQUENCE: 19

ctagcccagt tcgcgctgcc agggcgtaat atcgccaatg tgctcggcaa cgctcaagtt   60

agtataaaaa agctgaacga                                               80


<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20

agctgagtcg acatgtcgtg tgaagaactg gaa                                33
```

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21
agctgatcta gaatagatga ttacatcgca tcc 33

<210> SEQ ID NO 22
<211> LENGTH: 34
<212> TYPE: DNA
<213> ORGANISM: Artificial Sequence
<220> FEATURE:
<223> OTHER INFORMATION: primer

<400> SEQUENCE: 22
agctgagtcg acaaccctct gttatatgcc ttta 34

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
agctgagcat gcgagtgaag gttttgtttt gac 33

<210> SEQ ID NO 24
<211> LENGTH: 62
<212> TYPE: DNA
<213> ORGANISM: Artificial Sequence
<220> FEATURE:
<223> OTHER INFORMATION: primer

<400> SEQUENCE: 24
aagcttaaca cagaaaaaag cccgcacctg acagtgcggg cttttttttt cgaccactgc 60
ag 62

<210> SEQ ID NO 25
<211> LENGTH: 62
<212> TYPE: DNA
<213> ORGANISM: Artificial Sequence
<220> FEATURE:
<223> OTHER INFORMATION: primer

<400> SEQUENCE: 25
ttcgaattgt gtcttttttc gggcgtggac tgtcacgccc gaaaaaaaaa gctggtgacg 60
tc 62

<210> SEQ ID NO 26
<211> LENGTH: 37
<212> TYPE: DNA
<213> ORGANISM: Artificial Sequence
<220> FEATURE:
<223> OTHER INFORMATION: primer

<400> SEQUENCE: 26
ccagatcttg aagcctgctt ttttatacta agttggc 37

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
gaaatcaaat aatgatttta ttttg 25

<210> SEQ ID NO 28
<211> LENGTH: 26
<212> TYPE: DNA
<213> ORGANISM: Artificial Sequence
<220> FEATURE:
<223> OTHER INFORMATION: primer

<400> SEQUENCE: 28
ttacgccccg ccctgccact catcgc 26

<210> SEQ ID NO 29
<211> LENGTH: 34
<212> TYPE: DNA
<213> ORGANISM: Artificial Sequence
<220> FEATURE:
<223> OTHER INFORMATION: primer

<400> SEQUENCE: 29
gtcactgcag ctgatgtccg gcggtgcttt tgcc 34

<210> SEQ ID NO 30
<211> LENGTH: 31
<212> TYPE: DNA
<213> ORGANISM: Artificial Sequence
<220> FEATURE:
<223> OTHER INFORMATION: primer

<400> SEQUENCE: 30
cagctgcagt ctgttacagg tcactaatac c 31

<210> SEQ ID NO 31
<211> LENGTH: 37
<212> TYPE: DNA
<213> ORGANISM: Artificial Sequence
<220> FEATURE:
<223> OTHER INFORMATION: primer

<400> SEQUENCE: 31
ccgagctccg ctcaagttag tataaaaaag ctgaacg 37

<210> SEQ ID NO 32
<211> LENGTH: 70
<212> TYPE: DNA
<213> ORGANISM: Artificial Sequence
<220> FEATURE:
<223> OTHER INFORMATION: primer

<400> SEQUENCE: 32
cccgagctcg gtacctcgcg aatgcatcta gatgggcccg tcgactgcag aggcctgcat 60
gcaagcttcc 70

<210> SEQ ID NO 33
<211> LENGTH: 1056
<212> TYPE: DNA
<213> ORGANISM: Citrobacter koseri
<220> FEATURE:
<221> NAME/KEY: CDS
<222> LOCATION: (1)..(1056)

<400> SEQUENCE: 33

-continued

```
atg atg aat agc acc tgg gtt aaa aac gcc att aat gaa att aac gct       48
Met Met Asn Ser Thr Trp Val Lys Asn Ala Ile Asn Glu Ile Asn Ala
1               5                   10                  15

gac tat cag cgt tca gcc gac acg cat ctg atc cgg ttg tcg cta cca       96
Asp Tyr Gln Arg Ser Ala Asp Thr His Leu Ile Arg Leu Ser Leu Pro
            20                  25                  30

gcg ttt ccg ggc atc cag atc tac ctg aag gat gaa agc acc cat ccg      144
Ala Phe Pro Gly Ile Gln Ile Tyr Leu Lys Asp Glu Ser Thr His Pro
        35                  40                  45

acc ggc agc ctg aag cac cgt ctg gcg cgt tca ttg ttc ctg tat ggg      192
Thr Gly Ser Leu Lys His Arg Leu Ala Arg Ser Leu Phe Leu Tyr Gly
    50                  55                  60

ttg tgt aac ggc tgg att aaa gaa aac acg acc att att gaa tcc tcc      240
Leu Cys Asn Gly Trp Ile Lys Glu Asn Thr Thr Ile Ile Glu Ser Ser
65                  70                  75                  80

tcc ggt tca acg gcg gtt tcc gaa gcc tgg ttc gcc cga ctg ctc ggc      288
Ser Gly Ser Thr Ala Val Ser Glu Ala Trp Phe Ala Arg Leu Leu Gly
                85                  90                  95

ctg ccg ttt atc gcg gta atg cct tcc tgc acg gca aaa cgc aaa atc      336
Leu Pro Phe Ile Ala Val Met Pro Ser Cys Thr Ala Lys Arg Lys Ile
            100                 105                 110

gaa caa att gcg ttt tat ggc ggt cgc tgc cac ttt gtc gaa agc gcc      384
Glu Gln Ile Ala Phe Tyr Gly Gly Arg Cys His Phe Val Glu Ser Ala
        115                 120                 125

tgc gag att tac gcc gcc tct gag cag ctg gcg cac gaa ctg aac ggt      432
Cys Glu Ile Tyr Ala Ala Ser Glu Gln Leu Ala His Glu Leu Asn Gly
    130                 135                 140

cac tat atg gat cag ttc acc tat gcc gaa cgc gcc acc gac tgg cgc      480
His Tyr Met Asp Gln Phe Thr Tyr Ala Glu Arg Ala Thr Asp Trp Arg
145                 150                 155                 160

ggc aac aat aat atc gcc gac agt att ttc cat cag atg cag cgt gag      528
Gly Asn Asn Asn Ile Ala Asp Ser Ile Phe His Gln Met Gln Arg Glu
                165                 170                 175

cct aat ccg gtg ccg aag cat atc gtg atg agc gcg ggg acg ggc ggc      576
Pro Asn Pro Val Pro Lys His Ile Val Met Ser Ala Gly Thr Gly Gly
            180                 185                 190

acg tca gcg aca att ggc cgc tat att cgc tgt cat ggg tat gac acg      624
Thr Ser Ala Thr Ile Gly Arg Tyr Ile Arg Cys His Gly Tyr Asp Thr
        195                 200                 205

cgc ctg atg gtg gtt gac ccg gaa aac tcg gtc ttc ctg ccc tac tgg      672
Arg Leu Met Val Val Asp Pro Glu Asn Ser Val Phe Leu Pro Tyr Trp
    210                 215                 220

cag gat cgc gac gcc aca ttg cgc agc ccg gtg ggc agc aaa att gag      720
Gln Asp Arg Asp Ala Thr Leu Arg Ser Pro Val Gly Ser Lys Ile Glu
225                 230                 235                 240

ggg att ggc cgc ccg cgc gtg gaa ccc tcc ttc atc ccg gat gtg gtg      768
Gly Ile Gly Arg Pro Arg Val Glu Pro Ser Phe Ile Pro Asp Val Val
                245                 250                 255

gac gaa atg ctg cgc gta ccc gac gcc gcc agc gtc gcg acc gcg cac      816
Asp Glu Met Leu Arg Val Pro Asp Ala Ala Ser Val Ala Thr Ala His
            260                 265                 270

tgg ctg gaa aca cag ctg ggc cgt aaa gtg ggc gcc tcc acc ggc act      864
Trp Leu Glu Thr Gln Leu Gly Arg Lys Val Gly Ala Ser Thr Gly Thr
        275                 280                 285

aat atg tgg gga acg ttg cag atc gca gcc aga atg cgc gac gcc gga      912
Asn Met Trp Gly Thr Leu Gln Ile Ala Ala Arg Met Arg Asp Ala Gly
    290                 295                 300

gag acc ggt tct ctc gtc acg ctg ctg tgt gac agc ggc gaa cgc tat      960
Glu Thr Gly Ser Leu Val Thr Leu Leu Cys Asp Ser Gly Glu Arg Tyr
305                 310                 315                 320
```

```
ctc gac acc tat tac aat ccc cag tgg gtt aac gat cac att ggc gat      1008
Leu Asp Thr Tyr Tyr Asn Pro Gln Trp Val Asn Asp His Ile Gly Asp
                325                 330                 335

tta gcg ccg tgg cag gcg gaa att gcc caa ctg ctg aac gtc cgt taa      1056
Leu Ala Pro Trp Gln Ala Glu Ile Ala Gln Leu Leu Asn Val Arg
            340                 345                 350


<210> SEQ ID NO 34
<211> LENGTH: 351
<212> TYPE: PRT
<213> ORGANISM: Citrobacter koseri

<400> SEQUENCE: 34

Met Met Asn Ser Thr Trp Val Lys Asn Ala Ile Asn Glu Ile Asn Ala
1               5                   10                  15

Asp Tyr Gln Arg Ser Ala Asp Thr His Leu Ile Arg Leu Ser Leu Pro
            20                  25                  30

Ala Phe Pro Gly Ile Gln Ile Tyr Leu Lys Asp Glu Ser Thr His Pro
        35                  40                  45

Thr Gly Ser Leu Lys His Arg Leu Ala Arg Ser Leu Phe Leu Tyr Gly
    50                  55                  60

Leu Cys Asn Gly Trp Ile Lys Glu Asn Thr Thr Ile Ile Glu Ser Ser
65                  70                  75                  80

Ser Gly Ser Thr Ala Val Ser Glu Ala Trp Phe Ala Arg Leu Leu Gly
                85                  90                  95

Leu Pro Phe Ile Ala Val Met Pro Ser Cys Thr Ala Lys Arg Lys Ile
            100                 105                 110

Glu Gln Ile Ala Phe Tyr Gly Gly Arg Cys His Phe Val Glu Ser Ala
        115                 120                 125

Cys Glu Ile Tyr Ala Ala Ser Glu Gln Leu Ala His Glu Leu Asn Gly
    130                 135                 140

His Tyr Met Asp Gln Phe Thr Tyr Ala Glu Arg Ala Thr Asp Trp Arg
145                 150                 155                 160

Gly Asn Asn Asn Ile Ala Asp Ser Ile Phe His Gln Met Gln Arg Glu
                165                 170                 175

Pro Asn Pro Val Pro Lys His Ile Val Met Ser Ala Gly Thr Gly Gly
            180                 185                 190

Thr Ser Ala Thr Ile Gly Arg Tyr Ile Arg Cys His Gly Tyr Asp Thr
        195                 200                 205

Arg Leu Met Val Val Asp Pro Glu Asn Ser Val Phe Leu Pro Tyr Trp
    210                 215                 220

Gln Asp Arg Asp Ala Thr Leu Arg Ser Pro Val Gly Ser Lys Ile Glu
225                 230                 235                 240

Gly Ile Gly Arg Pro Arg Val Glu Pro Ser Phe Ile Pro Asp Val Val
                245                 250                 255

Asp Glu Met Leu Arg Val Pro Asp Ala Ala Ser Val Ala Thr Ala His
            260                 265                 270

Trp Leu Glu Thr Gln Leu Gly Arg Lys Val Gly Ala Ser Thr Gly Thr
        275                 280                 285

Asn Met Trp Gly Thr Leu Gln Ile Ala Ala Arg Met Arg Asp Ala Gly
    290                 295                 300

Glu Thr Gly Ser Leu Val Thr Leu Leu Cys Asp Ser Gly Glu Arg Tyr
305                 310                 315                 320

Leu Asp Thr Tyr Tyr Asn Pro Gln Trp Val Asn Asp His Ile Gly Asp
                325                 330                 335

Leu Ala Pro Trp Gln Ala Glu Ile Ala Gln Leu Leu Asn Val Arg
```

```
            340                 345                 350


<210> SEQ ID NO 35
<211> LENGTH: 1053
<212> TYPE: DNA
<213> ORGANISM: Klebsiella pneumoniae
<220> FEATURE:
<221> NAME/KEY: CDS
<222> LOCATION: (1)..(1053)

<400> SEQUENCE: 35

atg aat agc gcc tgg gtt aaa cat gcc att agc gaa atc aac gct gac       48
Met Asn Ser Ala Trp Val Lys His Ala Ile Ser Glu Ile Asn Ala Asp
1               5                   10                  15

tat cag cgc tcc gcc gac acg cac ctg atc cgt ctg ccg ctg ccc gct       96
Tyr Gln Arg Ser Ala Asp Thr His Leu Ile Arg Leu Pro Leu Pro Ala
            20                  25                  30

ttt ccg ggc atc cac ctg tat ctg aaa gat gaa agc acc cac ccc acc      144
Phe Pro Gly Ile His Leu Tyr Leu Lys Asp Glu Ser Thr His Pro Thr
        35                  40                  45

ggc agc ctg aag cat cgc ctg gcg cgg tcg ctg ttt ctc tat ggc ttg      192
Gly Ser Leu Lys His Arg Leu Ala Arg Ser Leu Phe Leu Tyr Gly Leu
    50                  55                  60

tgc aac ggc tgg atc aaa gaa ggc acg cca att ata gag tcc tcc tca      240
Cys Asn Gly Trp Ile Lys Glu Gly Thr Pro Ile Ile Glu Ser Ser Ser
65                  70                  75                  80

ggt tca acc gcc gtt tcg gag gcc tat ttc gcc cgc ctg ctg ggg ctg      288
Gly Ser Thr Ala Val Ser Glu Ala Tyr Phe Ala Arg Leu Leu Gly Leu
                85                  90                  95

ccg ttt atc gct gtg atg cct tcc tgc acc gcc aag cgc aaa atc gaa      336
Pro Phe Ile Ala Val Met Pro Ser Cys Thr Ala Lys Arg Lys Ile Glu
            100                 105                 110

cag atc gag ttc tac ggc gga cgc tgc cat ttt gtg cag agc gcc ggc      384
Gln Ile Glu Phe Tyr Gly Gly Arg Cys His Phe Val Gln Ser Ala Gly
        115                 120                 125

gaa atc tac gcg gct tcc gaa acg ctg gcc cgc gag ctg aac ggc cat      432
Glu Ile Tyr Ala Ala Ser Glu Thr Leu Ala Arg Glu Leu Asn Gly His
    130                 135                 140

tat atg gat cag ttt acc ttc gcc gag cgg gcc acc gac tgg cgc ggc      480
Tyr Met Asp Gln Phe Thr Phe Ala Glu Arg Ala Thr Asp Trp Arg Gly
145                 150                 155                 160

aac aac aat atc gcc gac agt att ttc cgc cag atg agc cat gag ccg      528
Asn Asn Asn Ile Ala Asp Ser Ile Phe Arg Gln Met Ser His Glu Pro
                165                 170                 175

cac ccg cag ccg tca tgg atc gtc atg agc gcc ggc acc ggc ggc acc      576
His Pro Gln Pro Ser Trp Ile Val Met Ser Ala Gly Thr Gly Gly Thr
            180                 185                 190

tca gcg acc att ggc cgc tat att cgc agc cag ggc tac gag acg cag      624
Ser Ala Thr Ile Gly Arg Tyr Ile Arg Ser Gln Gly Tyr Glu Thr Gln
        195                 200                 205

ctg atg gtc gtt gat ccg cag aat tcg gtg ttc ctc gat tac tgg cag      672
Leu Met Val Val Asp Pro Gln Asn Ser Val Phe Leu Asp Tyr Trp Gln
    210                 215                 220

acc cgc gac gcc agc ctg cgc agc ccg gtc ggc agc aaa att gaa ggc      720
Thr Arg Asp Ala Ser Leu Arg Ser Pro Val Gly Ser Lys Ile Glu Gly
225                 230                 235                 240

atc gga cgg ccg cgc gtc gag ccg tcg ttt att ccc gac gtt gtc gat      768
Ile Gly Arg Pro Arg Val Glu Pro Ser Phe Ile Pro Asp Val Val Asp
                245                 250                 255

gag atg ctg cgc gtg ccg gat gcg gcg agc gta gcc acc gcc ctg tgg      816
Glu Met Leu Arg Val Pro Asp Ala Ala Ser Val Ala Thr Ala Leu Trp
            260                 265                 270
```

```
ctg gaa acg cag ctt ggg cgc aag gtc ggc gcc tcg acc ggc acc aat      864
Leu Glu Thr Gln Leu Gly Arg Lys Val Gly Ala Ser Thr Gly Thr Asn
        275                 280                 285

atg tgg ggc gta ttg cag ctg gcc acg cgg atg cgc gag gaa ggt cgc      912
Met Trp Gly Val Leu Gln Leu Ala Thr Arg Met Arg Glu Glu Gly Arg
    290                 295                 300

acc ggc tcg ata gtg aca ctc ctg tgc gac agc ggc gag cgt tac ctg      960
Thr Gly Ser Ile Val Thr Leu Leu Cys Asp Ser Gly Glu Arg Tyr Leu
305                 310                 315                 320

gaa agc tat tac aac ccg cag tgg gtg gcg gac aat atc ggc gat att     1008
Glu Ser Tyr Tyr Asn Pro Gln Trp Val Ala Asp Asn Ile Gly Asp Ile
                325                 330                 335

gcg ccc tgg cag gcg gag atc gcc ggt ctg gtc gaa agg cga taa         1053
Ala Pro Trp Gln Ala Glu Ile Ala Gly Leu Val Glu Arg Arg
            340                 345                 350


<210> SEQ ID NO 36
<211> LENGTH: 350
<212> TYPE: PRT
<213> ORGANISM: Klebsiella pneumoniae

<400> SEQUENCE: 36

Met Asn Ser Ala Trp Val Lys His Ala Ile Ser Glu Ile Asn Ala Asp
1               5                   10                  15

Tyr Gln Arg Ser Ala Asp Thr His Leu Ile Arg Leu Pro Leu Pro Ala
            20                  25                  30

Phe Pro Gly Ile His Leu Tyr Leu Lys Asp Glu Ser Thr His Pro Thr
        35                  40                  45

Gly Ser Leu Lys His Arg Leu Ala Arg Ser Leu Phe Leu Tyr Gly Leu
    50                  55                  60

Cys Asn Gly Trp Ile Lys Glu Gly Thr Pro Ile Ile Glu Ser Ser Ser
65                  70                  75                  80

Gly Ser Thr Ala Val Ser Glu Ala Tyr Phe Ala Arg Leu Leu Gly Leu
                85                  90                  95

Pro Phe Ile Ala Val Met Pro Ser Cys Thr Ala Lys Arg Lys Ile Glu
            100                 105                 110

Gln Ile Glu Phe Tyr Gly Gly Arg Cys His Phe Val Gln Ser Ala Gly
        115                 120                 125

Glu Ile Tyr Ala Ala Ser Glu Thr Leu Ala Arg Glu Leu Asn Gly His
    130                 135                 140

Tyr Met Asp Gln Phe Thr Phe Ala Glu Arg Ala Thr Asp Trp Arg Gly
145                 150                 155                 160

Asn Asn Asn Ile Ala Asp Ser Ile Phe Arg Gln Met Ser His Glu Pro
                165                 170                 175

His Pro Gln Pro Ser Trp Ile Val Met Ser Ala Gly Thr Gly Gly Thr
            180                 185                 190

Ser Ala Thr Ile Gly Arg Tyr Ile Arg Ser Gln Gly Tyr Glu Thr Gln
        195                 200                 205

Leu Met Val Val Asp Pro Gln Asn Ser Val Phe Leu Asp Tyr Trp Gln
    210                 215                 220

Thr Arg Asp Ala Ser Leu Arg Ser Pro Val Gly Ser Lys Ile Glu Gly
225                 230                 235                 240

Ile Gly Arg Pro Arg Val Glu Pro Ser Phe Ile Pro Asp Val Val Asp
                245                 250                 255

Glu Met Leu Arg Val Pro Asp Ala Ala Ser Val Ala Thr Ala Leu Trp
            260                 265                 270
```

```
Leu Glu Thr Gln Leu Gly Arg Lys Val Gly Ala Ser Thr Gly Thr Asn
        275                 280                 285

Met Trp Gly Val Leu Gln Leu Ala Thr Arg Met Arg Glu Glu Gly Arg
    290                 295                 300

Thr Gly Ser Ile Val Thr Leu Leu Cys Asp Ser Gly Glu Arg Tyr Leu
305                 310                 315                 320

Glu Ser Tyr Tyr Asn Pro Gln Trp Val Ala Asp Asn Ile Gly Asp Ile
                325                 330                 335

Ala Pro Trp Gln Ala Glu Ile Ala Gly Leu Val Glu Arg Arg
            340                 345                 350


<210> SEQ ID NO 37
<211> LENGTH: 1047
<212> TYPE: DNA
<213> ORGANISM: Enterobacter sp.638
<220> FEATURE:
<221> NAME/KEY: CDS
<222> LOCATION: (1)..(1047)

<400> SEQUENCE: 37

atg aat agc tct tgg gtc aaa cat gcg att agc gaa att aat gcc gat       48
Met Asn Ser Ser Trp Val Lys His Ala Ile Ser Glu Ile Asn Ala Asp
1               5                   10                  15

tat caa cgt tcg gcg gat acg cat ctg att cgc ctc gcg ctg ccg ggt       96
Tyr Gln Arg Ser Ala Asp Thr His Leu Ile Arg Leu Ala Leu Pro Gly
            20                  25                  30

ttt gca ggc att cag ctc tat cta aaa gat gaa agt act cac cct aca      144
Phe Ala Gly Ile Gln Leu Tyr Leu Lys Asp Glu Ser Thr His Pro Thr
        35                  40                  45

ggc agc ctc aag cat cgt ctg gcg cga tcg ttg ttt ttg tat ggt ttg      192
Gly Ser Leu Lys His Arg Leu Ala Arg Ser Leu Phe Leu Tyr Gly Leu
    50                  55                  60

tgc aac ggc tgg atc aaa gaa ggc aca acg atc att gaa tcg tca tcg      240
Cys Asn Gly Trp Ile Lys Glu Gly Thr Thr Ile Ile Glu Ser Ser Ser
65                  70                  75                  80

ggt tca acg gcc gtg tca gaa gcc tat ttc gcg cgc ctg ctt ggc ctg      288
Gly Ser Thr Ala Val Ser Glu Ala Tyr Phe Ala Arg Leu Leu Gly Leu
                85                  90                  95

ccg ttt atc gcc gtg atg ccc tcc tgt acc gcg aaa cgc aaa atc gaa      336
Pro Phe Ile Ala Val Met Pro Ser Cys Thr Ala Lys Arg Lys Ile Glu
            100                 105                 110

cag atc gaa ttc tac ggc ggc cgc tgc cac ttt gtg gaa agc gcc tgc      384
Gln Ile Glu Phe Tyr Gly Gly Arg Cys His Phe Val Glu Ser Ala Cys
        115                 120                 125

gag att tac gcc gcc tcg gaa atg ctc gcc cgt gag ctg aac ggt cac      432
Glu Ile Tyr Ala Ala Ser Glu Met Leu Ala Arg Glu Leu Asn Gly His
    130                 135                 140

tat atg gac cag ttt acg ttt gct gag cgt gcg acc gac tgg cgc ggg      480
Tyr Met Asp Gln Phe Thr Phe Ala Glu Arg Ala Thr Asp Trp Arg Gly
145                 150                 155                 160

aac aac aac att gcg gac agt att ttc cgt cag atg aac aat gag ccg      528
Asn Asn Asn Ile Ala Asp Ser Ile Phe Arg Gln Met Asn Asn Glu Pro
                165                 170                 175

cac ccc cag ccg tcg tat atc gtc atg agc gcc ggg acg ggc ggt acc      576
His Pro Gln Pro Ser Tyr Ile Val Met Ser Ala Gly Thr Gly Gly Thr
            180                 185                 190

tcg gcg acg att ggt cgc tat atc cgc tgc cag ggc tat gac act caa      624
Ser Ala Thr Ile Gly Arg Tyr Ile Arg Cys Gln Gly Tyr Asp Thr Gln
        195                 200                 205

ctc atg gtg gtt gat ccg cag aat tct gtg ttt atg gat tac tgg cag      672
Leu Met Val Val Asp Pro Gln Asn Ser Val Phe Met Asp Tyr Trp Gln
```

```
    210                 215                 220

agc cgc gat gcc acg ctt cgc agc cca gtg ggc agt aaa atc gaa ggg      720
Ser Arg Asp Ala Thr Leu Arg Ser Pro Val Gly Ser Lys Ile Glu Gly
225                 230                 235                 240

att ggc cgc ccg cgc gta gag cct tct ttc att cct gat gtc gtc gat      768
Ile Gly Arg Pro Arg Val Glu Pro Ser Phe Ile Pro Asp Val Val Asp
                245                 250                 255

gag atg ttg cgt gtg cca gat gcg gca agc gtg gcg acg gca cac tgg      816
Glu Met Leu Arg Val Pro Asp Ala Ala Ser Val Ala Thr Ala His Trp
            260                 265                 270

ctg gaa acg cag ctt ggc cgc aaa gtg ggc gcg tca acc ggg acc aat      864
Leu Glu Thr Gln Leu Gly Arg Lys Val Gly Ala Ser Thr Gly Thr Asn
        275                 280                 285

atg tgg ggc gtt ctg cac ctg gct tca cga atg cgc gag gaa ggc cgc      912
Met Trp Gly Val Leu His Leu Ala Ser Arg Met Arg Glu Glu Gly Arg
    290                 295                 300

acc ggt tct atc gtt acc ctg ctg tgc gac agc ggc gag cgc tat ctc      960
Thr Gly Ser Ile Val Thr Leu Leu Cys Asp Ser Gly Glu Arg Tyr Leu
305                 310                 315                 320

gac acc tat tac aac gca gag tgg gtg aaa acc aat atc ggg gat atc     1008
Asp Thr Tyr Tyr Asn Ala Glu Trp Val Lys Thr Asn Ile Gly Asp Ile
                325                 330                 335

gaa ccg tgg aaa gcg cag atc gcg cag atg ctg aaa taa                 1047
Glu Pro Trp Lys Ala Gln Ile Ala Gln Met Leu Lys
            340                 345


<210> SEQ ID NO 38
<211> LENGTH: 348
<212> TYPE: PRT
<213> ORGANISM: Enterobacter sp.638

<400> SEQUENCE: 38

Met Asn Ser Ser Trp Val Lys His Ala Ile Ser Glu Ile Asn Ala Asp
1               5                   10                  15

Tyr Gln Arg Ser Ala Asp Thr His Leu Ile Arg Leu Ala Leu Pro Gly
            20                  25                  30

Phe Ala Gly Ile Gln Leu Tyr Leu Lys Asp Glu Ser Thr His Pro Thr
        35                  40                  45

Gly Ser Leu Lys His Arg Leu Ala Arg Ser Leu Phe Leu Tyr Gly Leu
    50                  55                  60

Cys Asn Gly Trp Ile Lys Glu Gly Thr Thr Ile Ile Glu Ser Ser Ser
65                  70                  75                  80

Gly Ser Thr Ala Val Ser Glu Ala Tyr Phe Ala Arg Leu Leu Gly Leu
                85                  90                  95

Pro Phe Ile Ala Val Met Pro Ser Cys Thr Ala Lys Arg Lys Ile Glu
            100                 105                 110

Gln Ile Glu Phe Tyr Gly Gly Arg Cys His Phe Val Glu Ser Ala Cys
        115                 120                 125

Glu Ile Tyr Ala Ala Ser Glu Met Leu Ala Arg Glu Leu Asn Gly His
    130                 135                 140

Tyr Met Asp Gln Phe Thr Phe Ala Glu Arg Ala Thr Asp Trp Arg Gly
145                 150                 155                 160

Asn Asn Asn Ile Ala Asp Ser Ile Phe Arg Gln Met Asn Asn Glu Pro
                165                 170                 175

His Pro Gln Pro Ser Tyr Ile Val Met Ser Ala Gly Thr Gly Gly Thr
            180                 185                 190

Ser Ala Thr Ile Gly Arg Tyr Ile Arg Cys Gln Gly Tyr Asp Thr Gln
        195                 200                 205
```

```
Leu Met Val Val Asp Pro Gln Asn Ser Val Phe Met Asp Tyr Trp Gln
    210                 215                 220

Ser Arg Asp Ala Thr Leu Arg Ser Pro Val Gly Ser Lys Ile Glu Gly
225                 230                 235                 240

Ile Gly Arg Pro Arg Val Glu Pro Ser Phe Ile Pro Asp Val Val Asp
                245                 250                 255

Glu Met Leu Arg Val Pro Asp Ala Ala Ser Val Ala Thr Ala His Trp
            260                 265                 270

Leu Glu Thr Gln Leu Gly Arg Lys Val Gly Ala Ser Thr Gly Thr Asn
        275                 280                 285

Met Trp Gly Val Leu His Leu Ala Ser Arg Met Arg Glu Glu Gly Arg
    290                 295                 300

Thr Gly Ser Ile Val Thr Leu Leu Cys Asp Ser Gly Glu Arg Tyr Leu
305                 310                 315                 320

Asp Thr Tyr Tyr Asn Ala Glu Trp Val Lys Thr Asn Ile Gly Asp Ile
                325                 330                 335

Glu Pro Trp Lys Ala Gln Ile Ala Gln Met Leu Lys
            340                 345


<210> SEQ ID NO 39
<211> LENGTH: 1056
<212> TYPE: DNA
<213> ORGANISM: Salmonella typhimurium
<220> FEATURE:
<221> NAME/KEY: CDS
<222> LOCATION: (1)..(1056)

<400> SEQUENCE: 39

atg atg agt agc aat tgg gtt aaa aat gcc att aat gaa att aac gct      48
Met Met Ser Ser Asn Trp Val Lys Asn Ala Ile Asn Glu Ile Asn Ala
1               5                   10                  15

gac cac cag cgc tcg gcg gat acg cat ctt att cgt ttg ccc ctg tcg      96
Asp His Gln Arg Ser Ala Asp Thr His Leu Ile Arg Leu Pro Leu Ser
            20                  25                  30

gca ttt cca ggt atc cag ctt tac ctg aaa gac gaa agc acg cat ccc     144
Ala Phe Pro Gly Ile Gln Leu Tyr Leu Lys Asp Glu Ser Thr His Pro
        35                  40                  45

acc ggt agc ctc aag cat cgt ctg gcg cgc tcg ctg ttc ctt tat ggg     192
Thr Gly Ser Leu Lys His Arg Leu Ala Arg Ser Leu Phe Leu Tyr Gly
    50                  55                  60

ttg tgc aat ggc tgg att aaa gaa ggc act ccg att att gaa gcg tca     240
Leu Cys Asn Gly Trp Ile Lys Glu Gly Thr Pro Ile Ile Glu Ala Ser
65                  70                  75                  80

tca ggc tca acg gcg att tcc gaa gcc tgg ttc gcg cgt tta ctg gga     288
Ser Gly Ser Thr Ala Ile Ser Glu Ala Trp Phe Ala Arg Leu Leu Gly
                85                  90                  95

ctg ccg ttc atc gcc gtc atg ccc gcc tgt acc gca aaa cgt aaa atc     336
Leu Pro Phe Ile Ala Val Met Pro Ala Cys Thr Ala Lys Arg Lys Ile
            100                 105                 110

gaa cag att caa ttt tac ggc ggc cac tgt cat ttt gtg gag agc gcc     384
Glu Gln Ile Gln Phe Tyr Gly Gly His Cys His Phe Val Glu Ser Ala
        115                 120                 125

tgc gaa att tat gcc gcc tcc gag cgg ctg gcg cat gaa ctg aac ggt     432
Cys Glu Ile Tyr Ala Ala Ser Glu Arg Leu Ala His Glu Leu Asn Gly
    130                 135                 140

cac tat atg gac cag ttt acc tac gca gaa cga gct acc gac tgg cgg     480
His Tyr Met Asp Gln Phe Thr Tyr Ala Glu Arg Ala Thr Asp Trp Arg
145                 150                 155                 160

ggc aac aat aat att gcc gac agt att ttc cgc cag atg cgc aac gaa     528
```

```
Gly Asn Asn Asn Ile Ala Asp Ser Ile Phe Arg Gln Met Arg Asn Glu
                165                 170                 175

ctc cat ccg gta ccg cga ttt atc gtc atg agc gcc gga acg ggc gga      576
Leu His Pro Val Pro Arg Phe Ile Val Met Ser Ala Gly Thr Gly Gly
            180                 185                 190

acc tct gcg acg att ggg cgc tat att cgc tgc cag ggc tat gat act      624
Thr Ser Ala Thr Ile Gly Arg Tyr Ile Arg Cys Gln Gly Tyr Asp Thr
        195                 200                 205

cag ctc atg gtg gtg gat ccg gaa aat tcc gtc ttt tta cct tac tgg      672
Gln Leu Met Val Val Asp Pro Glu Asn Ser Val Phe Leu Pro Tyr Trp
    210                 215                 220

cag gat cgc gac gct tca tta cgc agc ccg gta ggc agt aaa att gaa      720
Gln Asp Arg Asp Ala Ser Leu Arg Ser Pro Val Gly Ser Lys Ile Glu
225                 230                 235                 240

gga att ggt cgt ccg cga gta gag cct tct ttt att ccg gat gtc gtg      768
Gly Ile Gly Arg Pro Arg Val Glu Pro Ser Phe Ile Pro Asp Val Val
                245                 250                 255

gat gag atg ctg cgc gtg ccg gac gcc gcc agc gtt gcc acc gca cac      816
Asp Glu Met Leu Arg Val Pro Asp Ala Ala Ser Val Ala Thr Ala His
            260                 265                 270

tgg ctg gaa acg cag cta ggc cgt aaa gtc ggc gcc tct acc ggc acg      864
Trp Leu Glu Thr Gln Leu Gly Arg Lys Val Gly Ala Ser Thr Gly Thr
        275                 280                 285

aat atg tgg gga gct ctg cag ctt gcg gcc cgg atg cgc gag gct gga      912
Asn Met Trp Gly Ala Leu Gln Leu Ala Ala Arg Met Arg Glu Ala Gly
    290                 295                 300

gaa acc ggc gct atc gtg acg tta ttg tgc gat agc ggc gat cgc tat      960
Glu Thr Gly Ala Ile Val Thr Leu Leu Cys Asp Ser Gly Asp Arg Tyr
305                 310                 315                 320

ctg gat acc tat tac cat ccg gcc tgg gtt agc gac cat atc ggc gat     1008
Leu Asp Thr Tyr Tyr His Pro Ala Trp Val Ser Asp His Ile Gly Asp
                325                 330                 335

ttg acg ccg tgg tca gcg gcc atc gca aaa tta ctt acc ggc gac tag     1056
Leu Thr Pro Trp Ser Ala Ala Ile Ala Lys Leu Leu Thr Gly Asp
            340                 345                 350


<210> SEQ ID NO 40
<211> LENGTH: 351
<212> TYPE: PRT
<213> ORGANISM: Salmonella typhimurium

<400> SEQUENCE: 40

Met Met Ser Ser Asn Trp Val Lys Asn Ala Ile Asn Glu Ile Asn Ala
1               5                   10                  15

Asp His Gln Arg Ser Ala Asp Thr His Leu Ile Arg Leu Pro Leu Ser
            20                  25                  30

Ala Phe Pro Gly Ile Gln Leu Tyr Leu Lys Asp Glu Ser Thr His Pro
        35                  40                  45

Thr Gly Ser Leu Lys His Arg Leu Ala Arg Ser Leu Phe Leu Tyr Gly
    50                  55                  60

Leu Cys Asn Gly Trp Ile Lys Glu Gly Thr Pro Ile Ile Glu Ala Ser
65                  70                  75                  80

Ser Gly Ser Thr Ala Ile Ser Glu Ala Trp Phe Ala Arg Leu Leu Gly
                85                  90                  95

Leu Pro Phe Ile Ala Val Met Pro Ala Cys Thr Ala Lys Arg Lys Ile
            100                 105                 110

Glu Gln Ile Gln Phe Tyr Gly Gly His Cys His Phe Val Glu Ser Ala
        115                 120                 125

Cys Glu Ile Tyr Ala Ala Ser Glu Arg Leu Ala His Glu Leu Asn Gly
```

```
    130                 135                 140

His Tyr Met Asp Gln Phe Thr Tyr Ala Glu Arg Ala Thr Asp Trp Arg
145                 150                 155                 160

Gly Asn Asn Asn Ile Ala Asp Ser Ile Phe Arg Gln Met Arg Asn Glu
                165                 170                 175

Leu His Pro Val Pro Arg Phe Ile Val Met Ser Ala Gly Thr Gly Gly
            180                 185                 190

Thr Ser Ala Thr Ile Gly Arg Tyr Ile Arg Cys Gln Gly Tyr Asp Thr
        195                 200                 205

Gln Leu Met Val Val Asp Pro Glu Asn Ser Val Phe Leu Pro Tyr Trp
    210                 215                 220

Gln Asp Arg Asp Ala Ser Leu Arg Ser Pro Val Gly Ser Lys Ile Glu
225                 230                 235                 240

Gly Ile Gly Arg Pro Arg Val Glu Pro Ser Phe Ile Pro Asp Val Val
                245                 250                 255

Asp Glu Met Leu Arg Val Pro Asp Ala Ala Ser Val Ala Thr Ala His
            260                 265                 270

Trp Leu Glu Thr Gln Leu Gly Arg Lys Val Gly Ala Ser Thr Gly Thr
        275                 280                 285

Asn Met Trp Gly Ala Leu Gln Leu Ala Ala Arg Met Arg Glu Ala Gly
    290                 295                 300

Glu Thr Gly Ala Ile Val Thr Leu Leu Cys Asp Ser Gly Asp Arg Tyr
305                 310                 315                 320

Leu Asp Thr Tyr Tyr His Pro Ala Trp Val Ser Asp His Ile Gly Asp
                325                 330                 335

Leu Thr Pro Trp Ser Ala Ala Ile Ala Lys Leu Leu Thr Gly Asp
            340                 345                 350


<210> SEQ ID NO 41
<211> LENGTH: 1044
<212> TYPE: DNA
<213> ORGANISM: Serratia proteamaculans
<220> FEATURE:
<221> NAME/KEY: CDS
<222> LOCATION: (1)..(1044)

<400> SEQUENCE: 41

atg atg aca aat tct tgg gta aaa tat gct atc ggt gaa ata gaa gcg       48
Met Met Thr Asn Ser Trp Val Lys Tyr Ala Ile Gly Glu Ile Glu Ala
1               5                   10                  15

gat ttt caa cgc tcc gcc gat act cac ctg atc cgc ctg aac ctg ccg       96
Asp Phe Gln Arg Ser Ala Asp Thr His Leu Ile Arg Leu Asn Leu Pro
            20                  25                  30

gaa ttt ccc ggc atc tgc ctg tac ctg aaa gat gaa agc act cac ccg      144
Glu Phe Pro Gly Ile Cys Leu Tyr Leu Lys Asp Glu Ser Thr His Pro
        35                  40                  45

acc ggc agc ctg aag cac cgg ctg gcg cgt tca cta ttt ttg tat ggt      192
Thr Gly Ser Leu Lys His Arg Leu Ala Arg Ser Leu Phe Leu Tyr Gly
    50                  55                  60

ctg tgt aac ggc tgg atc acc gaa aac acc acg att atc gag gcc tcc      240
Leu Cys Asn Gly Trp Ile Thr Glu Asn Thr Thr Ile Ile Glu Ala Ser
65                  70                  75                  80

tcc ggc agt acc gcg gta tcc gaa gct tac ttc gcc cgg ctg att ggc      288
Ser Gly Ser Thr Ala Val Ser Glu Ala Tyr Phe Ala Arg Leu Ile Gly
                85                  90                  95

ctg ccg ttt att gcc gtc atg cct tcc tgt acc gca cgc cgc aag gtt      336
Leu Pro Phe Ile Ala Val Met Pro Ser Cys Thr Ala Arg Arg Lys Val
            100                 105                 110
```

```
gag cag atc gcg ttc tac ggc ggt cgc tgt cac ttc gtc gac cat gcg      384
Glu Gln Ile Ala Phe Tyr Gly Gly Arg Cys His Phe Val Asp His Ala
        115                 120                 125

gcg caa att tac gcc gtc tcc gaa cag ttg gcg aaa gag ctg aac ggc      432
Ala Gln Ile Tyr Ala Val Ser Glu Gln Leu Ala Lys Glu Leu Asn Gly
    130                 135                 140

cac tat atg gat cag ttc acc tac gct gaa cgg gcc acc gac tgg cgc      480
His Tyr Met Asp Gln Phe Thr Tyr Ala Glu Arg Ala Thr Asp Trp Arg
145                 150                 155                 160

ggc aac aac aac atc gcc gac agc atc ttc cgc cag atg gaa cgc gaa      528
Gly Asn Asn Asn Ile Ala Asp Ser Ile Phe Arg Gln Met Glu Arg Glu
                165                 170                 175

cct ttc ccg gta ccc aag cat atc gta atg agt gcc ggt acc ggt ggc      576
Pro Phe Pro Val Pro Lys His Ile Val Met Ser Ala Gly Thr Gly Gly
            180                 185                 190

acc tct gcg acc ctg ggc cgc tat atc cgc tat cag ggg cac gac acc      624
Thr Ser Ala Thr Leu Gly Arg Tyr Ile Arg Tyr Gln Gly His Asp Thr
        195                 200                 205

cgc ctg acg gtg gtc gat ccg gaa aat tcg gtg ttc tat gat tgc ttc      672
Arg Leu Thr Val Val Asp Pro Glu Asn Ser Val Phe Tyr Asp Cys Phe
    210                 215                 220

cac cag cat gac cgc acc ctt atc ggc agt tgc ggc agc cgt atc gag      720
His Gln His Asp Arg Thr Leu Ile Gly Ser Cys Gly Ser Arg Ile Glu
225                 230                 235                 240

ggc att ggc cgc cca cgc gcc gag cca tcc ttt att ccg tcg gtg gtc      768
Gly Ile Gly Arg Pro Arg Ala Glu Pro Ser Phe Ile Pro Ser Val Val
                245                 250                 255

gac agc atg atc cgc gtg ccg gat gcc gcc agc gtc gcc act atc cac      816
Asp Ser Met Ile Arg Val Pro Asp Ala Ala Ser Val Ala Thr Ile His
            260                 265                 270

tgg ctg gaa acg gtg ctc gga cgc aag gtc ggg gcc tcc acc ggc acc      864
Trp Leu Glu Thr Val Leu Gly Arg Lys Val Gly Ala Ser Thr Gly Thr
        275                 280                 285

aac gtg tgg ggt gcg ctg ctg ttg gcg aag caa atg cgg gaa aac ggc      912
Asn Val Trp Gly Ala Leu Leu Leu Ala Lys Gln Met Arg Glu Asn Gly
    290                 295                 300

gag cag ggt tcg att gtg act ctg ctg tgc gac agc ggt gag cgc tac      960
Glu Gln Gly Ser Ile Val Thr Leu Leu Cys Asp Ser Gly Glu Arg Tyr
305                 310                 315                 320

ctg gac acc tat tac aac ccg gaa tgg gtc aga aac aat atc ggt gat     1008
Leu Asp Thr Tyr Tyr Asn Pro Glu Trp Val Arg Asn Asn Ile Gly Asp
                325                 330                 335

ctg acg cct tat ctg gcg cag tta gca gat ttg taa                     1044
Leu Thr Pro Tyr Leu Ala Gln Leu Ala Asp Leu
            340                 345


<210> SEQ ID NO 42
<211> LENGTH: 347
<212> TYPE: PRT
<213> ORGANISM: Serratia proteamaculans

<400> SEQUENCE: 42

Met Met Thr Asn Ser Trp Val Lys Tyr Ala Ile Gly Glu Ile Glu Ala
1               5                   10                  15

Asp Phe Gln Arg Ser Ala Asp Thr His Leu Ile Arg Leu Asn Leu Pro
            20                  25                  30

Glu Phe Pro Gly Ile Cys Leu Tyr Leu Lys Asp Glu Ser Thr His Pro
        35                  40                  45

Thr Gly Ser Leu Lys His Arg Leu Ala Arg Ser Leu Phe Leu Tyr Gly
    50                  55                  60
```

```
Leu Cys Asn Gly Trp Ile Thr Glu Asn Thr Thr Ile Ile Glu Ala Ser
65                  70                  75                  80

Ser Gly Ser Thr Ala Val Ser Glu Ala Tyr Phe Ala Arg Leu Ile Gly
                85                  90                  95

Leu Pro Phe Ile Ala Val Met Pro Ser Cys Thr Ala Arg Arg Lys Val
            100                 105                 110

Glu Gln Ile Ala Phe Tyr Gly Gly Arg Cys His Phe Val Asp His Ala
        115                 120                 125

Ala Gln Ile Tyr Ala Val Ser Glu Gln Leu Ala Lys Glu Leu Asn Gly
    130                 135                 140

His Tyr Met Asp Gln Phe Thr Tyr Ala Glu Arg Ala Thr Asp Trp Arg
145                 150                 155                 160

Gly Asn Asn Asn Ile Ala Asp Ser Ile Phe Arg Gln Met Glu Arg Glu
                165                 170                 175

Pro Phe Pro Val Pro Lys His Ile Val Met Ser Ala Gly Thr Gly Gly
            180                 185                 190

Thr Ser Ala Thr Leu Gly Arg Tyr Ile Arg Tyr Gln Gly His Asp Thr
        195                 200                 205

Arg Leu Thr Val Val Asp Pro Glu Asn Ser Val Phe Tyr Asp Cys Phe
    210                 215                 220

His Gln His Asp Arg Thr Leu Ile Gly Ser Cys Gly Ser Arg Ile Glu
225                 230                 235                 240

Gly Ile Gly Arg Pro Arg Ala Glu Pro Ser Phe Ile Pro Ser Val Val
                245                 250                 255

Asp Ser Met Ile Arg Val Pro Asp Ala Ala Ser Val Ala Thr Ile His
            260                 265                 270

Trp Leu Glu Thr Val Leu Gly Arg Lys Val Gly Ala Ser Thr Gly Thr
        275                 280                 285

Asn Val Trp Gly Ala Leu Leu Leu Ala Lys Gln Met Arg Glu Asn Gly
    290                 295                 300

Glu Gln Gly Ser Ile Val Thr Leu Leu Cys Asp Ser Gly Glu Arg Tyr
305                 310                 315                 320

Leu Asp Thr Tyr Tyr Asn Pro Glu Trp Val Arg Asn Asn Ile Gly Asp
                325                 330                 335

Leu Thr Pro Tyr Leu Ala Gln Leu Ala Asp Leu
            340                 345


<210> SEQ ID NO 43
<211> LENGTH: 1077
<212> TYPE: DNA
<213> ORGANISM: Erwinia carotovora
<220> FEATURE:
<221> NAME/KEY: CDS
<222> LOCATION: (1)..(1077)

<400> SEQUENCE: 43

atg acc aat gcc tgg gtt aaa aat gcc atc agc gct atc gaa gca gat       48
Met Thr Asn Ala Trp Val Lys Asn Ala Ile Ser Ala Ile Glu Ala Asp
1               5                   10                  15

ttt cag cgt tcg gct gat acg cat ctt ata cgt ctg acc ctg ccg gat       96
Phe Gln Arg Ser Ala Asp Thr His Leu Ile Arg Leu Thr Leu Pro Asp
            20                  25                  30

tat ccc ggt atc tat ttt tat ctc aaa gat gaa agc aca cac ccc agc      144
Tyr Pro Gly Ile Tyr Phe Tyr Leu Lys Asp Glu Ser Thr His Pro Ser
        35                  40                  45

ggt agc ctg aag cat cgc ctg gcg cgc tcc ttg ttt ctc tac ggg ctg      192
Gly Ser Leu Lys His Arg Leu Ala Arg Ser Leu Phe Leu Tyr Gly Leu
    50                  55                  60
```

```
tgc aac ggt tgg att aaa gaa ggt acg cca att atc gaa gcg tca tct      240
Cys Asn Gly Trp Ile Lys Glu Gly Thr Pro Ile Ile Glu Ala Ser Ser
65                  70                  75                  80

ggc agt acc gcc gta tca gaa gcc tat ttt gca cgc ttg ctt ggc tta      288
Gly Ser Thr Ala Val Ser Glu Ala Tyr Phe Ala Arg Leu Leu Gly Leu
                85                  90                  95

ccg ttt att gcc gtc atg ccg tcc tgc acc gca aaa aga aaa ata gag      336
Pro Phe Ile Ala Val Met Pro Ser Cys Thr Ala Lys Arg Lys Ile Glu
            100                 105                 110

caa atc gct ttc tat ggc ggg cgc tgt cat ttt gtt gag cag gcg gga      384
Gln Ile Ala Phe Tyr Gly Gly Arg Cys His Phe Val Glu Gln Ala Gly
        115                 120                 125

caa atc tat gct gca tcc gaa cag ctg gcg caa gag atg aac ggc cac      432
Gln Ile Tyr Ala Ala Ser Glu Gln Leu Ala Gln Glu Met Asn Gly His
    130                 135                 140

tat atg gac cag ttc acc tac gcg gaa cgc gct acc gac tgg cgt ggc      480
Tyr Met Asp Gln Phe Thr Tyr Ala Glu Arg Ala Thr Asp Trp Arg Gly
145                 150                 155                 160

aat aac aat att gcc gac agc att tac cgt caa atg gca cgt gaa ccc      528
Asn Asn Asn Ile Ala Asp Ser Ile Tyr Arg Gln Met Ala Arg Glu Pro
                165                 170                 175

cat ccc gta ccg gac tac att gtg atg agt gcc ggt acg ggc ggc acg      576
His Pro Val Pro Asp Tyr Ile Val Met Ser Ala Gly Thr Gly Gly Thr
            180                 185                 190

tca gca acg ctc ggt cgc tac att cgc tat cag ggg ttg gat acg caa      624
Ser Ala Thr Leu Gly Arg Tyr Ile Arg Tyr Gln Gly Leu Asp Thr Gln
        195                 200                 205

ctg gtc gtc gtc gat cca gaa aac tcg gtc ttc tac gac tgc tat cag      672
Leu Val Val Val Asp Pro Glu Asn Ser Val Phe Tyr Asp Cys Tyr Gln
    210                 215                 220

aaa cag gat cgt tcc atc att ggc cca tgc ggc agt cgg ata gaa ggt      720
Lys Gln Asp Arg Ser Ile Ile Gly Pro Cys Gly Ser Arg Ile Glu Gly
225                 230                 235                 240

atc ggc cgc ccg cgt gcc gag cct tct ttt att cca ggc gtc att gat      768
Ile Gly Arg Pro Arg Ala Glu Pro Ser Phe Ile Pro Gly Val Ile Asp
                245                 250                 255

agc atg atc aaa gtg ccg gat gcc gcc agc atc gca acg ctg tac tgg      816
Ser Met Ile Lys Val Pro Asp Ala Ala Ser Ile Ala Thr Leu Tyr Trp
            260                 265                 270

ctg gaa agc gta tta ggc cgc aaa gca ggc gcc tct act ggc acg aat      864
Leu Glu Ser Val Leu Gly Arg Lys Ala Gly Ala Ser Thr Gly Thr Asn
        275                 280                 285

gtt tgg ggt atg ctg caa ttg gcc aaa gaa atg gtt aac cat ggc caa      912
Val Trp Gly Met Leu Gln Leu Ala Lys Glu Met Val Asn His Gly Gln
    290                 295                 300

aaa ggc gcg att gtg acc ctg tta tgt gac agc ggc gaa cgc tat ctg      960
Lys Gly Ala Ile Val Thr Leu Leu Cys Asp Ser Gly Glu Arg Tyr Leu
305                 310                 315                 320

gac acc tac tac aac agt agc tgg gta gaa aaa aac atc ggc gac att     1008
Asp Thr Tyr Tyr Asn Ser Ser Trp Val Glu Lys Asn Ile Gly Asp Ile
                325                 330                 335

agc cct tac ctc aac gcc ctg aac aac ccg gag atg tcc ttt ctc ata     1056
Ser Pro Tyr Leu Asn Ala Leu Asn Asn Pro Glu Met Ser Phe Leu Ile
            340                 345                 350

ccg gaa ccc agt ctg gcg tga                                         1077
Pro Glu Pro Ser Leu Ala
        355
```

<210> SEQ ID NO 44
<211> LENGTH: 358

```
<212> TYPE: PRT
<213> ORGANISM: Erwinia carotovora

<400> SEQUENCE: 44

Met Thr Asn Ala Trp Val Lys Asn Ala Ile Ser Ala Ile Glu Ala Asp
1               5                   10                  15

Phe Gln Arg Ser Ala Asp Thr His Leu Ile Arg Leu Thr Leu Pro Asp
            20                  25                  30

Tyr Pro Gly Ile Tyr Phe Tyr Leu Lys Asp Glu Ser Thr His Pro Ser
        35                  40                  45

Gly Ser Leu Lys His Arg Leu Ala Arg Ser Leu Phe Leu Tyr Gly Leu
    50                  55                  60

Cys Asn Gly Trp Ile Lys Glu Gly Thr Pro Ile Ile Glu Ala Ser Ser
65                  70                  75                  80

Gly Ser Thr Ala Val Ser Glu Ala Tyr Phe Ala Arg Leu Leu Gly Leu
                85                  90                  95

Pro Phe Ile Ala Val Met Pro Ser Cys Thr Ala Lys Arg Lys Ile Glu
            100                 105                 110

Gln Ile Ala Phe Tyr Gly Gly Arg Cys His Phe Val Glu Gln Ala Gly
        115                 120                 125

Gln Ile Tyr Ala Ala Ser Glu Gln Leu Ala Gln Glu Met Asn Gly His
    130                 135                 140

Tyr Met Asp Gln Phe Thr Tyr Ala Glu Arg Ala Thr Asp Trp Arg Gly
145                 150                 155                 160

Asn Asn Asn Ile Ala Asp Ser Ile Tyr Arg Gln Met Ala Arg Glu Pro
                165                 170                 175

His Pro Val Pro Asp Tyr Ile Val Met Ser Ala Gly Thr Gly Gly Thr
            180                 185                 190

Ser Ala Thr Leu Gly Arg Tyr Ile Arg Tyr Gln Gly Leu Asp Thr Gln
        195                 200                 205

Leu Val Val Val Asp Pro Glu Asn Ser Val Phe Tyr Asp Cys Tyr Gln
    210                 215                 220

Lys Gln Asp Arg Ser Ile Ile Gly Pro Cys Gly Ser Arg Ile Glu Gly
225                 230                 235                 240

Ile Gly Arg Pro Arg Ala Glu Pro Ser Phe Ile Pro Gly Val Ile Asp
                245                 250                 255

Ser Met Ile Lys Val Pro Asp Ala Ala Ser Ile Ala Thr Leu Tyr Trp
            260                 265                 270

Leu Glu Ser Val Leu Gly Arg Lys Ala Gly Ala Ser Thr Gly Thr Asn
        275                 280                 285

Val Trp Gly Met Leu Gln Leu Ala Lys Glu Met Val Asn His Gly Gln
    290                 295                 300

Lys Gly Ala Ile Val Thr Leu Leu Cys Asp Ser Gly Glu Arg Tyr Leu
305                 310                 315                 320

Asp Thr Tyr Tyr Asn Ser Ser Trp Val Glu Lys Asn Ile Gly Asp Ile
                325                 330                 335

Ser Pro Tyr Leu Asn Ala Leu Asn Asn Pro Glu Met Ser Phe Leu Ile
            340                 345                 350

Pro Glu Pro Ser Leu Ala
        355


<210> SEQ ID NO 45
<211> LENGTH: 1068
<212> TYPE: DNA
<213> ORGANISM: Vibrio cholerae
<220> FEATURE:
```

```
<221> NAME/KEY: CDS
<222> LOCATION: (1)..(1068)

<400> SEQUENCE: 45

atg tgt acc gac cat cag tgg att aac agt gca att cgt aaa att gaa       48
Met Cys Thr Asp His Gln Trp Ile Asn Ser Ala Ile Arg Lys Ile Glu
1               5                   10                  15

gca gac tat caa cgc tcc gcc gac acc cat ctg att aaa ctc gat tta       96
Ala Asp Tyr Gln Arg Ser Ala Asp Thr His Leu Ile Lys Leu Asp Leu
            20                  25                  30

cct tgc gtc tct ggc gtc gat atc tat ctg aaa gat gaa agt acc cac      144
Pro Cys Val Ser Gly Val Asp Ile Tyr Leu Lys Asp Glu Ser Thr His
        35                  40                  45

ccc acc ggt tct ctc aaa cac cgt ctc gcc cgt tca ctg ttt tta tat      192
Pro Thr Gly Ser Leu Lys His Arg Leu Ala Arg Ser Leu Phe Leu Tyr
    50                  55                  60

ggg ctg tgt aat ggc tgg att ggc cca gaa act acc att att gaa tcc      240
Gly Leu Cys Asn Gly Trp Ile Gly Pro Glu Thr Thr Ile Ile Glu Ser
65                  70                  75                  80

tca tct ggc agt act gcc gta tcg gaa gct tac ttt gct cgc ttg ctt      288
Ser Ser Gly Ser Thr Ala Val Ser Glu Ala Tyr Phe Ala Arg Leu Leu
                85                  90                  95

ggc cta ccc ttt att gcc gtg atg cca aag tgc acc gcg cgt aaa aaa      336
Gly Leu Pro Phe Ile Ala Val Met Pro Lys Cys Thr Ala Arg Lys Lys
            100                 105                 110

atc gaa cag atc cag ttc tat ggg ggc aag gcg cat ctt gta gat cgc      384
Ile Glu Gln Ile Gln Phe Tyr Gly Gly Lys Ala His Leu Val Asp Arg
        115                 120                 125

tcc gat caa att tac gca gaa tct cat cgt ctc gcg aaa gag ctg aaa      432
Ser Asp Gln Ile Tyr Ala Glu Ser His Arg Leu Ala Lys Glu Leu Lys
    130                 135                 140

ggc cac tac atg gat cag ttt act tac gct gaa cga gcc acc gac tgg      480
Gly His Tyr Met Asp Gln Phe Thr Tyr Ala Glu Arg Ala Thr Asp Trp
145                 150                 155                 160

cgt ggt aac agc aac atc gct gac agt att ttt agc cag atg cag atg      528
Arg Gly Asn Ser Asn Ile Ala Asp Ser Ile Phe Ser Gln Met Gln Met
                165                 170                 175

gaa caa cac ccc gtt cca agc tgg att gtg atg agc ccg ggg acg gga      576
Glu Gln His Pro Val Pro Ser Trp Ile Val Met Ser Pro Gly Thr Gly
            180                 185                 190

ggc acc tca gcc act atc ggc cgc ttt att cgc tac caa caa tac aac      624
Gly Thr Ser Ala Thr Ile Gly Arg Phe Ile Arg Tyr Gln Gln Tyr Asn
        195                 200                 205

acc aaa ctg tgt gtg gtt gac ccg gaa aac tcg gtt ttt tat gac tac      672
Thr Lys Leu Cys Val Val Asp Pro Glu Asn Ser Val Phe Tyr Asp Tyr
    210                 215                 220

tac cgc acg cga aat gcc gag cta acc cgt gac tgc ggc agc aaa att      720
Tyr Arg Thr Arg Asn Ala Glu Leu Thr Arg Asp Cys Gly Ser Lys Ile
225                 230                 235                 240

gaa ggc att ggc cgc cca aga gtc gag ccg agc ttt att cct gat gtg      768
Glu Gly Ile Gly Arg Pro Arg Val Glu Pro Ser Phe Ile Pro Asp Val
                245                 250                 255

gta gat gaa atg cgt gcg atc cct gat gcc gcg agt gta gcg acc atc      816
Val Asp Glu Met Arg Ala Ile Pro Asp Ala Ala Ser Val Ala Thr Ile
            260                 265                 270

tac tgg ttg gag aaa att ctt ggc cgt aaa gca ggc gcc tcc act ggc      864
Tyr Trp Leu Glu Lys Ile Leu Gly Arg Lys Ala Gly Ala Ser Thr Gly
        275                 280                 285

act aac ctg tat ggc gcg ctg caa ctc gcc tgc gaa atg aag cgc cgc      912
Thr Asn Leu Tyr Gly Ala Leu Gln Leu Ala Cys Glu Met Lys Arg Arg
    290                 295                 300
```

```
ggt gag caa ggt tcg att gtc acg ctc ttg tgc gat agc ggt gaa cgc      960
Gly Glu Gln Gly Ser Ile Val Thr Leu Leu Cys Asp Ser Gly Glu Arg
305                 310                 315                 320

tac ctt gat acc tat tac aac tct gag tgg gtc aaa aac aac att ggc     1008
Tyr Leu Asp Thr Tyr Tyr Asn Ser Glu Trp Val Lys Asn Asn Ile Gly
                325                 330                 335

gat tta agt aaa tat ctg cac aag ttg gaa aca ttc tcc gcg aca ggc     1056
Asp Leu Ser Lys Tyr Leu His Lys Leu Glu Thr Phe Ser Ala Thr Gly
            340                 345                 350

tgt ttg gat taa                                                     1068
Cys Leu Asp
        355


<210> SEQ ID NO 46
<211> LENGTH: 355
<212> TYPE: PRT
<213> ORGANISM: Vibrio cholerae

<400> SEQUENCE: 46

Met Cys Thr Asp His Gln Trp Ile Asn Ser Ala Ile Arg Lys Ile Glu
1               5                   10                  15

Ala Asp Tyr Gln Arg Ser Ala Asp Thr His Leu Ile Lys Leu Asp Leu
            20                  25                  30

Pro Cys Val Ser Gly Val Asp Ile Tyr Leu Lys Asp Glu Ser Thr His
        35                  40                  45

Pro Thr Gly Ser Leu Lys His Arg Leu Ala Arg Ser Leu Phe Leu Tyr
    50                  55                  60

Gly Leu Cys Asn Gly Trp Ile Gly Pro Glu Thr Thr Ile Ile Glu Ser
65                  70                  75                  80

Ser Ser Gly Ser Thr Ala Val Ser Glu Ala Tyr Phe Ala Arg Leu Leu
                85                  90                  95

Gly Leu Pro Phe Ile Ala Val Met Pro Lys Cys Thr Ala Arg Lys Lys
            100                 105                 110

Ile Glu Gln Ile Gln Phe Tyr Gly Gly Lys Ala His Leu Val Asp Arg
        115                 120                 125

Ser Asp Gln Ile Tyr Ala Glu Ser His Arg Leu Ala Lys Glu Leu Lys
    130                 135                 140

Gly His Tyr Met Asp Gln Phe Thr Tyr Ala Glu Arg Ala Thr Asp Trp
145                 150                 155                 160

Arg Gly Asn Ser Asn Ile Ala Asp Ser Ile Phe Ser Gln Met Gln Met
                165                 170                 175

Glu Gln His Pro Val Pro Ser Trp Ile Val Met Ser Pro Gly Thr Gly
            180                 185                 190

Gly Thr Ser Ala Thr Ile Gly Arg Phe Ile Arg Tyr Gln Gln Tyr Asn
        195                 200                 205

Thr Lys Leu Cys Val Val Asp Pro Glu Asn Ser Val Phe Tyr Asp Tyr
    210                 215                 220

Tyr Arg Thr Arg Asn Ala Glu Leu Thr Arg Asp Cys Gly Ser Lys Ile
225                 230                 235                 240

Glu Gly Ile Gly Arg Pro Arg Val Glu Pro Ser Phe Ile Pro Asp Val
                245                 250                 255

Val Asp Glu Met Arg Ala Ile Pro Asp Ala Ala Ser Val Ala Thr Ile
            260                 265                 270

Tyr Trp Leu Glu Lys Ile Leu Gly Arg Lys Ala Gly Ala Ser Thr Gly
        275                 280                 285

Thr Asn Leu Tyr Gly Ala Leu Gln Leu Ala Cys Glu Met Lys Arg Arg
```

```
    290                 295                 300

Gly Glu Gln Gly Ser Ile Val Thr Leu Leu Cys Asp Ser Gly Glu Arg
305                 310                 315                 320

Tyr Leu Asp Thr Tyr Tyr Asn Ser Glu Trp Val Lys Asn Asn Ile Gly
                325                 330                 335

Asp Leu Ser Lys Tyr Leu His Lys Leu Glu Thr Phe Ser Ala Thr Gly
            340                 345                 350

Cys Leu Asp
        355


<210> SEQ ID NO 47
<211> LENGTH: 1095
<212> TYPE: DNA
<213> ORGANISM: Pseudomonas fluorescens
<220> FEATURE:
<221> NAME/KEY: CDS
<222> LOCATION: (1)..(1095)

<400> SEQUENCE: 47

atg agc gac aac cga cag tgg gcc cgc gaa gcc atc cgg atc atc gaa       48
Met Ser Asp Asn Arg Gln Trp Ala Arg Glu Ala Ile Arg Ile Ile Glu
1               5                   10                  15

gcg gac ttc cag cgc agc gcc gac acc cac ctg atc cct ttg ccg ctg       96
Ala Asp Phe Gln Arg Ser Ala Asp Thr His Leu Ile Pro Leu Pro Leu
            20                  25                  30

ccg ggt ttt ccg ggc atc aaa ctg tac ttc aag gac gag tcc agc cac      144
Pro Gly Phe Pro Gly Ile Lys Leu Tyr Phe Lys Asp Glu Ser Ser His
        35                  40                  45

ccg acc ggc agc ctc aag cat cgg ctg gcc cgg tcg ctg ttt ctt tac      192
Pro Thr Gly Ser Leu Lys His Arg Leu Ala Arg Ser Leu Phe Leu Tyr
    50                  55                  60

gcg ttg tgt aat ggc tgg ctc aaa ccc ggg gcg ccg gtg atc gag gcg      240
Ala Leu Cys Asn Gly Trp Leu Lys Pro Gly Ala Pro Val Ile Glu Ala
65                  70                  75                  80

tcc agc gga tcg acg gcg att tcc gaa gcg tac ttc gca cgg atg ctc      288
Ser Ser Gly Ser Thr Ala Ile Ser Glu Ala Tyr Phe Ala Arg Met Leu
                85                  90                  95

ggc ctg ccg ttc att gcg gtg atg ccg gcg acc acc tcc aag gag aag      336
Gly Leu Pro Phe Ile Ala Val Met Pro Ala Thr Thr Ser Lys Glu Lys
            100                 105                 110

att gcg cag atc gcc ttc tac ggt ggc cag agt cat ctg gtg gat gat      384
Ile Ala Gln Ile Ala Phe Tyr Gly Gly Gln Ser His Leu Val Asp Asp
        115                 120                 125

ccg acc cag atc tac gcc gaa tcc gaa cgc ctg gcc cgc gag cac gac      432
Pro Thr Gln Ile Tyr Ala Glu Ser Glu Arg Leu Ala Arg Glu His Asp
    130                 135                 140

ggt cac ttc atc gac cag ttc acc tac gcc gag cgc gcc acc gac tgg      480
Gly His Phe Ile Asp Gln Phe Thr Tyr Ala Glu Arg Ala Thr Asp Trp
145                 150                 155                 160

cgg gcg aac aac aac atc gcc gag tcg atc ttc cag cag atg cgc tat      528
Arg Ala Asn Asn Asn Ile Ala Glu Ser Ile Phe Gln Gln Met Arg Tyr
                165                 170                 175

gag cag cat cca tgc ccg gcc tgg ctg att tcc agc ccc ggc acc ggt      576
Glu Gln His Pro Cys Pro Ala Trp Leu Ile Ser Ser Pro Gly Thr Gly
            180                 185                 190

ggt acc acg gcg acc ctg ggg cgt tac gta cgt tat cgc cag cac tgc      624
Gly Thr Thr Ala Thr Leu Gly Arg Tyr Val Arg Tyr Arg Gln His Cys
        195                 200                 205

act cgc gtg ctg tgc gcc gat gcc gag cgt tcg gtg ttc ttc gac ttt      672
Thr Arg Val Leu Cys Ala Asp Ala Glu Arg Ser Val Phe Phe Asp Phe
    210                 215                 220
```

```
tac cag agc ggc gat gcc agc ctg cgt ctg gac cac ggt tcg cgg atc      720
Tyr Gln Ser Gly Asp Ala Ser Leu Arg Leu Asp His Gly Ser Arg Ile
225                 230                 235                 240

gaa ggg atc ggc cgg ccg cgg gta gaa gcg tcg ttc ctg ccg aag gta      768
Glu Gly Ile Gly Arg Pro Arg Val Glu Ala Ser Phe Leu Pro Lys Val
                245                 250                 255

atc gat gcg atg gtc aag gtg ccg gac gcc ttg tcg ctg gcg gcc atg      816
Ile Asp Ala Met Val Lys Val Pro Asp Ala Leu Ser Leu Ala Ala Met
            260                 265                 270

cat tac ctg gcg cag cgt ctg ggc cgg cat gtt ggc ggg tcg agc ggc      864
His Tyr Leu Ala Gln Arg Leu Gly Arg His Val Gly Gly Ser Ser Gly
        275                 280                 285

act aac ctg atc ggc gca ttg atg gcg gcg cag cag atg aaa gcg gcg      912
Thr Asn Leu Ile Gly Ala Leu Met Ala Ala Gln Gln Met Lys Ala Ala
    290                 295                 300

ggg gag tcg ggc tcg atc gtg gcg atc ctg tgc gat ggt ggc gag cgt      960
Gly Glu Ser Gly Ser Ile Val Ala Ile Leu Cys Asp Gly Gly Glu Arg
305                 310                 315                 320

tac gcg gac acc tat tac gat cag gcg tgg ctc aag gcg caa ggc tat     1008
Tyr Ala Asp Thr Tyr Tyr Asp Gln Ala Trp Leu Lys Ala Gln Gly Tyr
                325                 330                 335

gaa ctg gat gga ttg atg gcg gcc gtg gca gcg agt gcc gag cag ggt     1056
Glu Leu Asp Gly Leu Met Ala Ala Val Ala Ala Ser Ala Glu Gln Gly
            340                 345                 350

gag gcg ctg ccg gcc tcg gtt ctg cgt gcc aat atc tga                 1095
Glu Ala Leu Pro Ala Ser Val Leu Arg Ala Asn Ile
        355                 360


<210> SEQ ID NO 48
<211> LENGTH: 364
<212> TYPE: PRT
<213> ORGANISM: Pseudomonas fluorescens

<400> SEQUENCE: 48

Met Ser Asp Asn Arg Gln Trp Ala Arg Glu Ala Ile Arg Ile Ile Glu
1               5                   10                  15

Ala Asp Phe Gln Arg Ser Ala Asp Thr His Leu Ile Pro Leu Pro Leu
            20                  25                  30

Pro Gly Phe Pro Gly Ile Lys Leu Tyr Phe Lys Asp Glu Ser Ser His
        35                  40                  45

Pro Thr Gly Ser Leu Lys His Arg Leu Ala Arg Ser Leu Phe Leu Tyr
    50                  55                  60

Ala Leu Cys Asn Gly Trp Leu Lys Pro Gly Ala Pro Val Ile Glu Ala
65                  70                  75                  80

Ser Ser Gly Ser Thr Ala Ile Ser Glu Ala Tyr Phe Ala Arg Met Leu
                85                  90                  95

Gly Leu Pro Phe Ile Ala Val Met Pro Ala Thr Thr Ser Lys Glu Lys
            100                 105                 110

Ile Ala Gln Ile Ala Phe Tyr Gly Gly Gln Ser His Leu Val Asp Asp
        115                 120                 125

Pro Thr Gln Ile Tyr Ala Glu Ser Glu Arg Leu Ala Arg Glu His Asp
    130                 135                 140

Gly His Phe Ile Asp Gln Phe Thr Tyr Ala Glu Arg Ala Thr Asp Trp
145                 150                 155                 160

Arg Ala Asn Asn Asn Ile Ala Glu Ser Ile Phe Gln Gln Met Arg Tyr
                165                 170                 175

Glu Gln His Pro Cys Pro Ala Trp Leu Ile Ser Ser Pro Gly Thr Gly
            180                 185                 190
```

```
Gly Thr Thr Ala Thr Leu Gly Arg Tyr Val Arg Tyr Arg Gln His Cys
        195                 200                 205

Thr Arg Val Leu Cys Ala Asp Ala Glu Arg Ser Val Phe Phe Asp Phe
    210                 215                 220

Tyr Gln Ser Gly Asp Ala Ser Leu Arg Leu Asp His Gly Ser Arg Ile
225                 230                 235                 240

Glu Gly Ile Gly Arg Pro Arg Val Glu Ala Ser Phe Leu Pro Lys Val
                245                 250                 255

Ile Asp Ala Met Val Lys Val Pro Asp Ala Leu Ser Leu Ala Ala Met
            260                 265                 270

His Tyr Leu Ala Gln Arg Leu Gly Arg His Val Gly Gly Ser Ser Gly
        275                 280                 285

Thr Asn Leu Ile Gly Ala Leu Met Ala Ala Gln Gln Met Lys Ala Ala
    290                 295                 300

Gly Glu Ser Gly Ser Ile Val Ala Ile Leu Cys Asp Gly Gly Glu Arg
305                 310                 315                 320

Tyr Ala Asp Thr Tyr Tyr Asp Gln Ala Trp Leu Lys Ala Gln Gly Tyr
                325                 330                 335

Glu Leu Asp Gly Leu Met Ala Ala Val Ala Ala Ser Ala Glu Gln Gly
            340                 345                 350

Glu Ala Leu Pro Ala Ser Val Leu Arg Ala Asn Ile
        355                 360


<210> SEQ ID NO 49
<211> LENGTH: 1125
<212> TYPE: DNA
<213> ORGANISM: Streptomyces coelicolor
<220> FEATURE:
<221> NAME/KEY: CDS
<222> LOCATION: (1)..(1125)

<400> SEQUENCE: 49

gtg agc act gac cga cag acc ggc acc ggc acc acc ctc gac gtc gac       48
Val Ser Thr Asp Arg Gln Thr Gly Thr Gly Thr Thr Leu Asp Val Asp
1               5                   10                  15

cgc agc gac gcc tcc tac cgt gcc tgg ctg aaa gag gcc gtc cgc aag       96
Arg Ser Asp Ala Ser Tyr Arg Ala Trp Leu Lys Glu Ala Val Arg Lys
            20                  25                  30

gtc cag gcc gac gcg aac cgc tcg gcc gac acc cac ctg ctc ctg ttc      144
Val Gln Ala Asp Ala Asn Arg Ser Ala Asp Thr His Leu Leu Leu Phe
        35                  40                  45

ccg ctc ccc gag cac tgg ggc atc gac ctg tac ctg aag gac gag tcg      192
Pro Leu Pro Glu His Trp Gly Ile Asp Leu Tyr Leu Lys Asp Glu Ser
    50                  55                  60

acc cac ccg acc ggc agc ctc aag cac cgg ctc gcc cgc tcc ctg ttc      240
Thr His Pro Thr Gly Ser Leu Lys His Arg Leu Ala Arg Ser Leu Phe
65                  70                  75                  80

ctc tac ggc ctg tgc aac ggc tgg atc cgg ccg gac cgc ccg gtg atc      288
Leu Tyr Gly Leu Cys Asn Gly Trp Ile Arg Pro Asp Arg Pro Val Ile
                85                  90                  95

gag gcg tcc agc ggc tcg acg gcc gtc tcc gag gcc tat ttc gcc aag      336
Glu Ala Ser Ser Gly Ser Thr Ala Val Ser Glu Ala Tyr Phe Ala Lys
            100                 105                 110

ctg gtc ggc gtc ccc ttc atc gcc gtc atg ccc cgg acg acg agc gcc      384
Leu Val Gly Val Pro Phe Ile Ala Val Met Pro Arg Thr Thr Ser Ala
        115                 120                 125

gag aag atc cgg ctg atc gag ttc cac ggg gga cgg tgc cac ttc gtg      432
Glu Lys Ile Arg Leu Ile Glu Phe His Gly Gly Arg Cys His Phe Val
    130                 135                 140
```

```
gac gac tcc cgg cgg atg tac gag gag tcg gcc cgc ctc gcg gcg gag      480
Asp Asp Ser Arg Arg Met Tyr Glu Glu Ser Ala Arg Leu Ala Ala Glu
145                 150                 155                 160

acc ggc ggc cac tac atg gac cag ttc acc tac gcc gaa cgc gcc acg      528
Thr Gly Gly His Tyr Met Asp Gln Phe Thr Tyr Ala Glu Arg Ala Thr
                165                 170                 175

gac tgg cgc ggc aac aac aac atc gcc gag tcg atc ttc cgt cag ctg      576
Asp Trp Arg Gly Asn Asn Asn Ile Ala Glu Ser Ile Phe Arg Gln Leu
            180                 185                 190

cgg ctg gaa cgg tat ccc gag ccg tcc tgg atc gtc gcc acg gcc ggc      624
Arg Leu Glu Arg Tyr Pro Glu Pro Ser Trp Ile Val Ala Thr Ala Gly
        195                 200                 205

acc ggc ggc acc tcg gcg acc ctc gcc cgc tac gtc cac tac atg cag      672
Thr Gly Gly Thr Ser Ala Thr Leu Ala Arg Tyr Val His Tyr Met Gln
    210                 215                 220

tac gac acc cgc gtc tgc gtc gcc gac ccg gac aac tcc tgc ttc ttc      720
Tyr Asp Thr Arg Val Cys Val Ala Asp Pro Asp Asn Ser Cys Phe Phe
225                 230                 235                 240

gag ggt tgg acc acc ggc gac ccc gac gtg gcc tgc gac cgc ggc tcc      768
Glu Gly Trp Thr Thr Gly Asp Pro Asp Val Ala Cys Asp Arg Gly Ser
                245                 250                 255

cgc atc gag ggc atc ggc cgg ccc cgg atg gaa ccg agc ttc gta ccc      816
Arg Ile Glu Gly Ile Gly Arg Pro Arg Met Glu Pro Ser Phe Val Pro
            260                 265                 270

ggc gcg atc gac cgc atg atg aag gtg ccg gac gcg gcc agc gtc gcg      864
Gly Ala Ile Asp Arg Met Met Lys Val Pro Asp Ala Ala Ser Val Ala
        275                 280                 285

gcc gtg cgg tcc ctg gag cgg gcc atc ggc cgc agg gcg ggc ggc tcc      912
Ala Val Arg Ser Leu Glu Arg Ala Ile Gly Arg Arg Ala Gly Gly Ser
    290                 295                 300

acc ggc acc ggg ctg tgg agc gcg ttg aag atc gtc gcc gag atg gtg      960
Thr Gly Thr Gly Leu Trp Ser Ala Leu Lys Ile Val Ala Glu Met Val
305                 310                 315                 320

gcc gcg ggg gag cgg ggc agc gtc gtg aca ctg ctg tgc gat ccg ggg     1008
Ala Ala Gly Glu Arg Gly Ser Val Val Thr Leu Leu Cys Asp Pro Gly
                325                 330                 335

gac cgg tac ctc gac aag tac tac tcg gac gcc tgg ctc gcc gaa cag     1056
Asp Arg Tyr Leu Asp Lys Tyr Tyr Ser Asp Ala Trp Leu Ala Glu Gln
            340                 345                 350

ggc ctc gac atc gag ccg tac acg gcg gcg atc gag tcc ctg ctg cgc     1104
Gly Leu Asp Ile Glu Pro Tyr Thr Ala Ala Ile Glu Ser Leu Leu Arg
        355                 360                 365

acc ggc agc ctg ctc gac tga                                         1125
Thr Gly Ser Leu Leu Asp
    370


<210> SEQ ID NO 50
<211> LENGTH: 374
<212> TYPE: PRT
<213> ORGANISM: Streptomyces coelicolor

<400> SEQUENCE: 50

Val Ser Thr Asp Arg Gln Thr Gly Thr Gly Thr Thr Leu Asp Val Asp
1               5                   10                  15

Arg Ser Asp Ala Ser Tyr Arg Ala Trp Leu Lys Glu Ala Val Arg Lys
            20                  25                  30

Val Gln Ala Asp Ala Asn Arg Ser Ala Asp Thr His Leu Leu Leu Phe
        35                  40                  45

Pro Leu Pro Glu His Trp Gly Ile Asp Leu Tyr Leu Lys Asp Glu Ser
    50                  55                  60
```

```
Thr His Pro Thr Gly Ser Leu Lys His Arg Leu Ala Arg Ser Leu Phe
65                  70                  75                  80

Leu Tyr Gly Leu Cys Asn Gly Trp Ile Arg Pro Asp Arg Pro Val Ile
                85                  90                  95

Glu Ala Ser Ser Gly Ser Thr Ala Val Ser Glu Ala Tyr Phe Ala Lys
            100                 105                 110

Leu Val Gly Val Pro Phe Ile Ala Val Met Pro Arg Thr Thr Ser Ala
        115                 120                 125

Glu Lys Ile Arg Leu Ile Glu Phe His Gly Gly Arg Cys His Phe Val
    130                 135                 140

Asp Asp Ser Arg Arg Met Tyr Glu Glu Ser Ala Arg Leu Ala Ala Glu
145                 150                 155                 160

Thr Gly Gly His Tyr Met Asp Gln Phe Thr Tyr Ala Glu Arg Ala Thr
                165                 170                 175

Asp Trp Arg Gly Asn Asn Asn Ile Ala Glu Ser Ile Phe Arg Gln Leu
            180                 185                 190

Arg Leu Glu Arg Tyr Pro Glu Pro Ser Trp Ile Val Ala Thr Ala Gly
        195                 200                 205

Thr Gly Gly Thr Ser Ala Thr Leu Ala Arg Tyr Val His Tyr Met Gln
    210                 215                 220

Tyr Asp Thr Arg Val Cys Val Ala Asp Pro Asp Asn Ser Cys Phe Phe
225                 230                 235                 240

Glu Gly Trp Thr Thr Gly Asp Pro Asp Val Ala Cys Asp Arg Gly Ser
                245                 250                 255

Arg Ile Glu Gly Ile Gly Arg Pro Arg Met Glu Pro Ser Phe Val Pro
            260                 265                 270

Gly Ala Ile Asp Arg Met Met Lys Val Pro Asp Ala Ala Ser Val Ala
        275                 280                 285

Ala Val Arg Ser Leu Glu Arg Ala Ile Gly Arg Arg Ala Gly Gly Ser
    290                 295                 300

Thr Gly Thr Gly Leu Trp Ser Ala Leu Lys Ile Val Ala Glu Met Val
305                 310                 315                 320

Ala Ala Gly Glu Arg Gly Ser Val Val Thr Leu Leu Cys Asp Pro Gly
                325                 330                 335

Asp Arg Tyr Leu Asp Lys Tyr Tyr Ser Asp Ala Trp Leu Ala Glu Gln
            340                 345                 350

Gly Leu Asp Ile Glu Pro Tyr Thr Ala Ala Ile Glu Ser Leu Leu Arg
        355                 360                 365

Thr Gly Ser Leu Leu Asp
    370
```

<210> SEQ ID NO 51
<211> LENGTH: 1104
<212> TYPE: DNA
<213> ORGANISM: Mycobacterium avium
<220> FEATURE:
<221> NAME/KEY: CDS
<222> LOCATION: (1)..(1104)

<400> SEQUENCE: 51

```
gtg acg cgg acc cgg atc gcg gtc cgc aac ctg cca cgc gac tgg acg       48
Val Thr Arg Thr Arg Ile Ala Val Arg Asn Leu Pro Arg Asp Trp Thr
1               5                   10                  15

gac aac gcg atc cgg ctg atc cag gcc gat gcg cgg cgc agc gcc gac       96
Asp Asn Ala Ile Arg Leu Ile Gln Ala Asp Ala Arg Arg Ser Ala Asp
            20                  25                  30
```

```
acc cat ctg ctg cgc tac ccg ctg ccg tcg gcc tgg gcc ggc gac gcc      144
Thr His Leu Leu Arg Tyr Pro Leu Pro Ser Ala Trp Ala Gly Asp Ala
        35                  40                  45

gac gtc gcg ctg tac ctc aag gac gag acg acg cac gtc acc ggc agc      192
Asp Val Ala Leu Tyr Leu Lys Asp Glu Thr Thr His Val Thr Gly Ser
    50                  55                  60

ctc aag cac cgg ctg gcg cgc tcg ctg ttc ctg tac gcg ctg tgc aac      240
Leu Lys His Arg Leu Ala Arg Ser Leu Phe Leu Tyr Ala Leu Cys Asn
65                  70                  75                  80

ggc tgg atc ggc gag ggc acc acg gtg gtc gag gcg tcg tcg ggg tcg      288
Gly Trp Ile Gly Glu Gly Thr Thr Val Val Glu Ala Ser Ser Gly Ser
                85                  90                  95

acg gcg gtg tcc gag gcc tac ttc gcg gcc ctg ctg ggg ctg ccg ttc      336
Thr Ala Val Ser Glu Ala Tyr Phe Ala Ala Leu Leu Gly Leu Pro Phe
            100                 105                 110

gtc gcc gtg atg ccg gag tcg acc agc gcg gcc aag gtc gcg ctg atc      384
Val Ala Val Met Pro Glu Ser Thr Ser Ala Ala Lys Val Ala Leu Ile
        115                 120                 125

gaa tca caa ggc ggc cgt tgc cat ttc gtc gcg gat tcc agc cag gtg      432
Glu Ser Gln Gly Gly Arg Cys His Phe Val Ala Asp Ser Ser Gln Val
    130                 135                 140

tac gcc gag gcc gag cgg gtg gcc cgg cag agc ggc ggg cac tac ctg      480
Tyr Ala Glu Ala Glu Arg Val Ala Arg Gln Ser Gly Gly His Tyr Leu
145                 150                 155                 160

gac cag ttc acc aac gcc gag cgg gcc acc gac tgg cgc ggc aac aac      528
Asp Gln Phe Thr Asn Ala Glu Arg Ala Thr Asp Trp Arg Gly Asn Asn
                165                 170                 175

aac atc gcc gag tcg atc ttc gag cag atg cgc gac gag aaa cac ccc      576
Asn Ile Ala Glu Ser Ile Phe Glu Gln Met Arg Asp Glu Lys His Pro
            180                 185                 190

gtg ccg gcc tgg atc gtg gtc ggc gcg ggc acc ggc ggg acg agc gcg      624
Val Pro Ala Trp Ile Val Val Gly Ala Gly Thr Gly Gly Thr Ser Ala
        195                 200                 205

acc atc ggc cgc tac atc cgc tac cgg cgg cac gcc acc cgg ctg tgc      672
Thr Ile Gly Arg Tyr Ile Arg Tyr Arg Arg His Ala Thr Arg Leu Cys
    210                 215                 220

gtc gtc gac ccg gag cac tcg gcg ttc ttc gcg gcc tac gcc gaa ggc      720
Val Val Asp Pro Glu His Ser Ala Phe Phe Ala Ala Tyr Ala Glu Gly
225                 230                 235                 240

cgg gac gac gtg gtg gcg tcc cgg tcg tcg cgg atc gag ggc atc ggc      768
Arg Asp Asp Val Val Ala Ser Arg Ser Ser Arg Ile Glu Gly Ile Gly
                245                 250                 255

cgg ccg cgg gtc gag ccg tcg ttt ctg ccc ggc gtg gtc gac cgc atg      816
Arg Pro Arg Val Glu Pro Ser Phe Leu Pro Gly Val Val Asp Arg Met
            260                 265                 270

gtc gcc gtg ccg gac gcg gcc tcc gtc gcc gcc gcc cgc cac gtc agc      864
Val Ala Val Pro Asp Ala Ala Ser Val Ala Ala Ala Arg His Val Ser
        275                 280                 285

gcc gtg ctg ggc cgg cgg gtg ggg ccc tcg acg ggc acc aac gtg tgg      912
Ala Val Leu Gly Arg Arg Val Gly Pro Ser Thr Gly Thr Asn Val Trp
    290                 295                 300

ggg gcg ttc ggc ctg ctg gcc gag ctg gtg tcg cag ggc cgc ggc ggt      960
Gly Ala Phe Gly Leu Leu Ala Glu Leu Val Ser Gln Gly Arg Gly Gly
305                 310                 315                 320

tcg gtg gtc acg ctg ctc gcc gac agc ggc gac cgg tac gcc gac acc     1008
Ser Val Val Thr Leu Leu Ala Asp Ser Gly Asp Arg Tyr Ala Asp Thr
                325                 330                 335

tac ttc gac gac gag tgg gtg gcg gcg cag ggg ctg gat ccg gcc gga     1056
Tyr Phe Asp Asp Glu Trp Val Ala Ala Gln Gly Leu Asp Pro Ala Gly
            340                 345                 350
```

```
ccg gcc gcg gcg ctg gcc gaa ttc gag cgc agt tgc gcg tgg cag tga      1104
Pro Ala Ala Ala Leu Ala Glu Phe Glu Arg Ser Cys Ala Trp Gln
        355                 360                 365


<210> SEQ ID NO 52
<211> LENGTH: 367
<212> TYPE: PRT
<213> ORGANISM: Mycobacterium avium

<400> SEQUENCE: 52

Val Thr Arg Thr Arg Ile Ala Val Arg Asn Leu Pro Arg Asp Trp Thr
1               5                   10                  15

Asp Asn Ala Ile Arg Leu Ile Gln Ala Asp Ala Arg Arg Ser Ala Asp
            20                  25                  30

Thr His Leu Leu Arg Tyr Pro Leu Pro Ser Ala Trp Ala Gly Asp Ala
        35                  40                  45

Asp Val Ala Leu Tyr Leu Lys Asp Glu Thr Thr His Val Thr Gly Ser
    50                  55                  60

Leu Lys His Arg Leu Ala Arg Ser Leu Phe Leu Tyr Ala Leu Cys Asn
65                  70                  75                  80

Gly Trp Ile Gly Glu Gly Thr Thr Val Val Glu Ala Ser Ser Gly Ser
                85                  90                  95

Thr Ala Val Ser Glu Ala Tyr Phe Ala Ala Leu Leu Gly Leu Pro Phe
            100                 105                 110

Val Ala Val Met Pro Glu Ser Thr Ser Ala Ala Lys Val Ala Leu Ile
        115                 120                 125

Glu Ser Gln Gly Gly Arg Cys His Phe Val Ala Asp Ser Ser Gln Val
    130                 135                 140

Tyr Ala Glu Ala Glu Arg Val Ala Arg Gln Ser Gly Gly His Tyr Leu
145                 150                 155                 160

Asp Gln Phe Thr Asn Ala Glu Arg Ala Thr Asp Trp Arg Gly Asn Asn
                165                 170                 175

Asn Ile Ala Glu Ser Ile Phe Glu Gln Met Arg Asp Glu Lys His Pro
            180                 185                 190

Val Pro Ala Trp Ile Val Val Gly Ala Gly Thr Gly Gly Thr Ser Ala
        195                 200                 205

Thr Ile Gly Arg Tyr Ile Arg Tyr Arg Arg His Ala Thr Arg Leu Cys
    210                 215                 220

Val Val Asp Pro Glu His Ser Ala Phe Phe Ala Ala Tyr Ala Glu Gly
225                 230                 235                 240

Arg Asp Asp Val Val Ala Ser Arg Ser Ser Arg Ile Glu Gly Ile Gly
                245                 250                 255

Arg Pro Arg Val Glu Pro Ser Phe Leu Pro Gly Val Val Asp Arg Met
            260                 265                 270

Val Ala Val Pro Asp Ala Ala Ser Val Ala Ala Ala Arg His Val Ser
        275                 280                 285

Ala Val Leu Gly Arg Arg Val Gly Pro Ser Thr Gly Thr Asn Val Trp
    290                 295                 300

Gly Ala Phe Gly Leu Leu Ala Glu Leu Val Ser Gln Gly Arg Gly Gly
305                 310                 315                 320

Ser Val Val Thr Leu Leu Ala Asp Ser Gly Asp Arg Tyr Ala Asp Thr
                325                 330                 335

Tyr Phe Asp Asp Glu Trp Val Ala Ala Gln Gly Leu Asp Pro Ala Gly
            340                 345                 350

Pro Ala Ala Ala Leu Ala Glu Phe Glu Arg Ser Cys Ala Trp Gln
        355                 360                 365
```

<210> SEQ ID NO 53
<211> LENGTH: 40
<212> TYPE: DNA
<213> ORGANISM: Artificial Sequence
<220> FEATURE:
<223> OTHER INFORMATION: primer for amplifying attL

<400> SEQUENCE: 53
ctagtaagat cttgaagcct gctttttat actaagttgg 40

<210> SEQ ID NO 54
<211> LENGTH: 41
<212> TYPE: DNA
<213> ORGANISM: Artificial Sequence
<220> FEATURE:
<223> OTHER INFORMATION: primer for amplifying attL

<400> SEQUENCE: 54
atgatcgaat tcgaaatcaa ataatgattt tattttgact g 41

<210> SEQ ID NO 55
<211> LENGTH: 120
<212> TYPE: DNA
<213> ORGANISM: Escherichia coli

<400> SEQUENCE: 55
agatcttgaa gcctgctttt ttatactaag ttggcattat aaaaaagcat tgcttatcaa 60
tttgttgcaa cgaacaggtc actatcagtc aaaataaaat cattatttga tttcgaattc 120

<210> SEQ ID NO 56
<211> LENGTH: 41
<212> TYPE: DNA
<213> ORGANISM: Artificial Sequence
<220> FEATURE:
<223> OTHER INFORMATION: primer for amplifying attR

<400> SEQUENCE: 56
atgccactgc agtctgttac aggtcactaa taccatctaa g 41

<210> SEQ ID NO 57
<211> LENGTH: 46
<212> TYPE: DNA
<213> ORGANISM: Artificial Sequence
<220> FEATURE:
<223> OTHER INFORMATION: primer for amplifying attR

<400> SEQUENCE: 57
accgttaagc tttctagacg ctcaagttag tataaaaaag ctgaac 46

<210> SEQ ID NO 58
<211> LENGTH: 184
<212> TYPE: DNA
<213> ORGANISM: Escherichia coli

<400> SEQUENCE: 58
ctgcagtctg ttacaggtca ctaataccat ctaagtagtt gattcatagt gactgcatat 60
gttgtgtttt acagtattat gtagtctgtt ttttatgcaa aatctaattt aatatattga 120
tatttatatc attttacgtt tctcgttcag cttttttata ctaacttgag cgtctagaaa 180
gctt 184

<210> SEQ ID NO 59
<211> LENGTH: 38

<212> TYPE: DNA
<213> ORGANISM: Artificial Sequence
<220> FEATURE:
<223> OTHER INFORMATION: primer for amplifying bla

<400> SEQUENCE: 59
ttcttagacg tcaggtggca cttttcgggg aaatgtgc 38

<210> SEQ ID NO 60
<211> LENGTH: 37
<212> TYPE: DNA
<213> ORGANISM: Artificial Sequence
<220> FEATURE:
<223> OTHER INFORMATION: primer for amplifying bla

<400> SEQUENCE: 60
taacagagat ctcgcgcaga aaaaaaggat ctcaaga 37

<210> SEQ ID NO 61
<211> LENGTH: 46
<212> TYPE: DNA
<213> ORGANISM: Artificial Sequence
<220> FEATURE:
<223> OTHER INFORMATION: primer for amplifying ter_rrnB

<400> SEQUENCE: 61
aacagagatc taagcttaga tcctttgcct ggcggcagta gcgcgg 46

<210> SEQ ID NO 62
<211> LENGTH: 35
<212> TYPE: DNA
<213> ORGANISM: Artificial Sequence
<220> FEATURE:
<223> OTHER INFORMATION: primer for amplifying ter_rrnB

<400> SEQUENCE: 62
ataaactgca gcaaaaagag tttgtagaaa cgcaa 35

<210> SEQ ID NO 63
<211> LENGTH: 1388
<212> TYPE: DNA
<213> ORGANISM: Escherichia coli

<400> SEQUENCE: 63
gaattctcat gtttgacagc ttatcatcga taagctttaa tgcggtagtt tatcacagtt 60
aaattgctaa cgcagtcagg caccgtgtat gaaatctaac aatgcgctca tcgtcatcct 120
cggcaccgtc accctggatg ctgtaggcat aggcttggtt atgccggtac tgccgggcct 180
cttgcgggat atcgtccatt ccgacagcat cgccagtcac tatggcgtgc tgctagcgct 240
atatgcgttg atgcaatttc tatgcgcacc cgttctcgga gcactgtccg accgctttgg 300
ccgccgccca gtcctgctcg cttcgctact tggagccact atcgactacg cgatcatggc 360
gaccacaccc gtcctgtgga tcctctacgc cggacgcatc gtggccggca tcaccggcgc 420
cacaggtgcg gttgctggcg cctatatcgc cgacatcacc gatggggaag atcgggctcg 480
ccacttcggg ctcatgagcg cttgtttcgg cgtgggtatg gtggcaggcc ccgtggccgg 540
gggactgttg ggcgccatct ccttgcatgc accattcctt gcggcggcgg tgctcaacgg 600
cctcaaccta ctactgggct gcttcctaat gcaggagtcg cataagggag agcgtcgacc 660
gatgcccttg agagccttca acccagtcag ctccttccgg tgggcgcggg gcatgactat 720
cgtcgccgca cttatgactg tcttctttat catgcaactc gtaggacagg tgccggcagc 780
gctctgggtc attttcggcg aggaccgctt tcgctggagc gcgacgatga tcggcctgtc 840

```
gcttgcggta ttcggaatct tgcacgccct cgctcaagcc ttcgtcactg gtcccgccac    900

caaacgtttc ggcgagaagc aggccattat cgccggcatg gcggccgacg cgctgggcta    960

cgtcttgctg gcgttcgcga cgcgaggctg gatggccttc cccattatga ttcttctcgc   1020

ttccggcggc atcgggatgc ccgcgttgca ggccatgctg tccaggcagg tagatgacga   1080

ccatcaggga cagcttcaag gatcgctcgc ggctcttacc agcctaactt cgatcactgg   1140

accgctgatc gtcacggcga tttatgccgc ctcggcgagc acatggaacg ggttggcatg   1200

gattgtaggc gccgccctat accttgtctg cctccccgcg ttgcgtcgcg gtgcatggag   1260

ccgggccacc tcgacctgaa tggaagccgg cggcacctcg ctaacggatt caccactcca   1320

actagaaagc ttaacacaga aaaaagcccg cacctgacag tgcgggcttt tttttcgac   1380

cactgcag                                                            1388
```

```
<210> SEQ ID NO 64
<211> LENGTH: 36
<212> TYPE: DNA
<213> ORGANISM: Artificial Sequence
<220> FEATURE:
<223> OTHER INFORMATION: primer for amplifying ter_thrL

<400> SEQUENCE: 64

agtaattcta gaaagcttaa cacagaaaaa agcccg                               36


<210> SEQ ID NO 65
<211> LENGTH: 43
<212> TYPE: DNA
<213> ORGANISM: Artificial Sequence
<220> FEATURE:
<223> OTHER INFORMATION: primer for amplifying ter_thrL

<400> SEQUENCE: 65

ctagtaggat ccctgcagtg gtcgaaaaaa aaagcccgca ctg                       43


<210> SEQ ID NO 66
<211> LENGTH: 501
<212> TYPE: DNA
<213> ORGANISM: Pantoea ananatis
<220> FEATURE:
<221> NAME/KEY: CDS
<222> LOCATION: (1)..(501)

<400> SEQUENCE: 66

atg gcg gta atg gag aaa ata ttt cta ccg gag ggc cgt atg cca gat       48
Met Ala Val Met Glu Lys Ile Phe Leu Pro Glu Gly Arg Met Pro Asp
1               5                   10                  15

aaa att gac ctt aaa ctg ttg gct atg ctg cag cag gac tgc acc act       96
Lys Ile Asp Leu Lys Leu Leu Ala Met Leu Gln Gln Asp Cys Thr Thr
            20                  25                  30

tca ctc cag gta ctg gca gat gcg gtt aat ctc acc acg acg ccc tgt      144
Ser Leu Gln Val Leu Ala Asp Ala Val Asn Leu Thr Thr Thr Pro Cys
        35                  40                  45

tgg aag cgc ctt aaa aag ctg gaa gaa gac ggc att att cgc gga cgg      192
Trp Lys Arg Leu Lys Lys Leu Glu Glu Asp Gly Ile Ile Arg Gly Arg
    50                  55                  60

gtc gct ctg ctg gat aat gaa aag ctt ggc ctc tgt ctc acg gcc ttt      240
Val Ala Leu Leu Asp Asn Glu Lys Leu Gly Leu Cys Leu Thr Ala Phe
65                  70                  75                  80

atg ttt gtc aaa acc acc cag cac agc aaa gcc tgg tat cag gag ttc      288
Met Phe Val Lys Thr Thr Gln His Ser Lys Ala Trp Tyr Gln Glu Phe
                85                  90                  95
```

-continued

```
gtc tcg gtg gtg cag agc atg ccg gaa gtg atg ggc ttt tac cgt atg      336
Val Ser Val Val Gln Ser Met Pro Glu Val Met Gly Phe Tyr Arg Met
            100                 105                 110

gcc ggt gag tac gat tat tta ctg cgt att cag gtt gcc gac atg aaa      384
Ala Gly Glu Tyr Asp Tyr Leu Leu Arg Ile Gln Val Ala Asp Met Lys
        115                 120                 125

agt tat gat gcc ttt tat aag cgt tta gtt aat ggt gta aca ggc ctg      432
Ser Tyr Asp Ala Phe Tyr Lys Arg Leu Val Asn Gly Val Thr Gly Leu
    130                 135                 140

atc gat gtg acc tcc agc ttc gcg atg gaa gag att aaa tac acg aca      480
Ile Asp Val Thr Ser Ser Phe Ala Met Glu Glu Ile Lys Tyr Thr Thr
145                 150                 155                 160

gcc ctg cct gtt ggc ccc tga                                          501
Ala Leu Pro Val Gly Pro
                165


<210> SEQ ID NO 67
<211> LENGTH: 166
<212> TYPE: PRT
<213> ORGANISM: Pantoea ananatis

<400> SEQUENCE: 67

Met Ala Val Met Glu Lys Ile Phe Leu Pro Glu Gly Arg Met Pro Asp
1               5                   10                  15

Lys Ile Asp Leu Lys Leu Leu Ala Met Leu Gln Gln Asp Cys Thr Thr
            20                  25                  30

Ser Leu Gln Val Leu Ala Asp Ala Val Asn Leu Thr Thr Thr Pro Cys
        35                  40                  45

Trp Lys Arg Leu Lys Lys Leu Glu Glu Asp Gly Ile Ile Arg Gly Arg
    50                  55                  60

Val Ala Leu Leu Asp Asn Glu Lys Leu Gly Leu Cys Leu Thr Ala Phe
65                  70                  75                  80

Met Phe Val Lys Thr Thr Gln His Ser Lys Ala Trp Tyr Gln Glu Phe
                85                  90                  95

Val Ser Val Val Gln Ser Met Pro Glu Val Met Gly Phe Tyr Arg Met
            100                 105                 110

Ala Gly Glu Tyr Asp Tyr Leu Leu Arg Ile Gln Val Ala Asp Met Lys
        115                 120                 125

Ser Tyr Asp Ala Phe Tyr Lys Arg Leu Val Asn Gly Val Thr Gly Leu
    130                 135                 140

Ile Asp Val Thr Ser Ser Phe Ala Met Glu Glu Ile Lys Tyr Thr Thr
145                 150                 155                 160

Ala Leu Pro Val Gly Pro
                165
```

L-CYSTEINE PRODUCING BACTERIUM AND A METHOD FOR PRODUCING L-CYSTEINE

This application claims priority under 35 U.S.C. §119 to Japanese Patent Application No. 2008-056371, filed on Mar. 6, 2008, which is incorporated in its entirety by reference. The Sequence Listing in electronic format filed herewith is also hereby incorporated by reference in its entirety (File Name: US-386_Seq_List; File Size: 95 KB; Date Created: Mar. 4, 2009).

BACKGROUND OF THE INVENTION

1. Field of the Invention

The present invention relates to a method for producing L-cysteine or related substances. More precisely, the present invention relates to a bacterium suitable for the production of L-cysteine or related substances and a method for producing L-cysteine or related substances utilizing such a bacterium. L-cysteine and L-cysteine-related substances are used in the fields of drugs, cosmetics, and foods.

2. Brief Description of the Related Art

Microorganisms which are able to produce L-cysteine are known, for example, a coryneform bacterium with increased intracellular serine acetyltransferase activity has been described (Japanese Patent Laid-open (Kokai) No. 2002-233384). Increasing L-cysteine-producing ability by incorporating a mutant serine acetyltransferase which is desensitized to feedback inhibition by L-cysteine has also been described (Japanese Patent Laid-open No. 11-155571, U.S. Patent Published Application No. 20050112731, U.S. Pat. No. 6,218,168).

Furthermore, microorganisms in which the ability to produce L-cysteine is enhanced by suppressing the L-cysteine decomposition system are also known, for example, coryneform bacteria or *Escherichia* bacteria have been reported in which the activity of cystathionine-β-lyase (U.S. Patent Published Application No. 20050112731), tryptophanase (Japanese Patent Laid-open No. 2003-169668), or O-acetylserine sulfhydrylase B (Japanese Patent Laid-open No. 2005-245311) is attenuated or deleted.

Furthermore, the ydeD gene, which encodes the YdeD protein, participates in secretion of the metabolic products of the cysteine pathway (Dabler et al., Mol. Microbiol., 36, 1101-1112 (2000)). Other techniques for enhancing L-cysteine-producing ability are known, including by increasing expression of the mar locus, emr locus, acr locus, cmr locus, mex gene, bmr gene, or qacA gene. These are all genes which encode proteins which function to secrete toxic substances out of cells (U.S. Pat. No. 5,972,663). The emrAB, emrKY, yojIH, acrEF, or cusA genes are also known (Japanese Patent Laid-open No. 2005-287333).

Furthermore, an L-cysteine-producing *Escherichia coli* has been reported in which the activity of the positive transcriptional control factor of the cysteine regulon encoded by the cysB gene is increased (International Patent Publication WO01/27307).

The d0191 gene is a novel gene of *Pantoea ananatis* which was found by the inventors of the present invention. Although presumably homologous genes to d0191 have been found in various bacteria by homology searches, the functions of all of them are unknown, and their relation with L-cysteine production is also unknown.

SUMMARY OF THE INVENTION

An aspect of the present invention is to develop a novel technique for improving bacterial L-cysteine-producing ability, and thereby provide an L-cysteine-producing bacterium, and a method for producing L-cysteine, L-cystine, their derivatives, or a mixture of these by using such a bacterium.

A novel gene has been found which encodes a protein having cysteine desulfhydrase activity in *Pantoea ananatis*, and it has been found that L-cysteine-producing ability of a bacterium can be enhanced by modifying the bacterium so that the activity of that protein is decreased.

It is an aspect of the present invention to provide a bacterium belonging to the family Enterobacteriaceae, which has L-cysteine-producing ability and has been modified to decrease the activity of a protein selected from the group consisting of:

(A) a protein comprising the amino acid sequence of SEQ ID NO: 2, and (B) a protein comprising the amino acid sequence of SEQ ID NO: 2 but which includes substitutions, deletions, insertions, or additions of one or several amino acid residues, and wherein said protein comprises cysteine desulfhydrase activity.

It is a further aspect of the present invention to provide the aforementioned bacterium, wherein the activity of the protein is decreased by a method selected from the group consisting of decreasing the expression of a gene encoding the protein, and by disrupting the gene encoding the protein.

It is a further aspect of the present invention to provide the aforementioned bacterium, wherein the gene is selected from the group consisting of:

(a) a DNA comprising the nucleotide sequence of SEQ ID NO: 1, and (b) a DNA which is able to hybridize with a sequence complementary to the nucleotide sequence of SEQ ID NO: 1, or a probe prepared from the nucleotide sequence, under stringent conditions, and encodes a protein comprising cysteine desulfhydrase activity.

It is a further aspect of the present invention to provide the aforementioned bacterium, in which serine acetyltransferase has been mutated so that feedback inhibition by L-cysteine is attenuated.

It is a further aspect of the present invention to provide the aforementioned bacterium, which is a *Pantoea* bacterium.

It is a further aspect of the present invention to provide the aforementioned bacterium, which is *Pantoea ananatis*.

It is a further aspect of the present invention to provide a method for producing an L-amino acid selected from the group consisting of L-cysteine, L-cystine, derivatives thereof, and combinations thereof, which comprises culturing the aforementioned bacterium in a medium and collecting the L-amino acid from the medium.

It is a further aspect of the present invention to provide the aforementioned method, wherein the derivative of L-cysteine is a thiazolidine derivative.

It is a further aspect of the present invention to provide a DNA encoding a protein selected from the group consisting of:

(A) a protein comprising the amino acid sequence of SEQ ID NO: 2, and (B) a protein comprising the amino acid sequence of SEQ ID NO: 2 but which includes substitutions, deletions, insertions, or additions of one or several amino acid residues, and wherein said protein comprises cysteine desulfhydrase activity.

It is a further aspect of the present invention to provide the aforementioned DNA, which is a DNA selected from the group consisting of:

(a) a DNA comprising the nucleotide sequence of SEQ ID NO: 1, and (b) a DNA which is able to hybridize with a sequence complementary to the nucleotide sequence of SEQ ID NO: 1, or a probe prepared from the nucleotide sequence, under stringent conditions, and encodes a protein comprising cysteine desulfhydrase activity.

According to the present invention, L-cysteine-producing ability of bacteria can be improved. Furthermore, according to the present invention, L-cysteine, L-cystine, their derivatives, or a mixture thereof can be efficiently produced.

Moreover, the present invention provides a novel gene encoding a protein having cysteine desulfhydrase activity.

DETAILED DESCRIPTION OF EXEMPLARY EMBODIMENTS

<1> Bacterium

Figure 1:
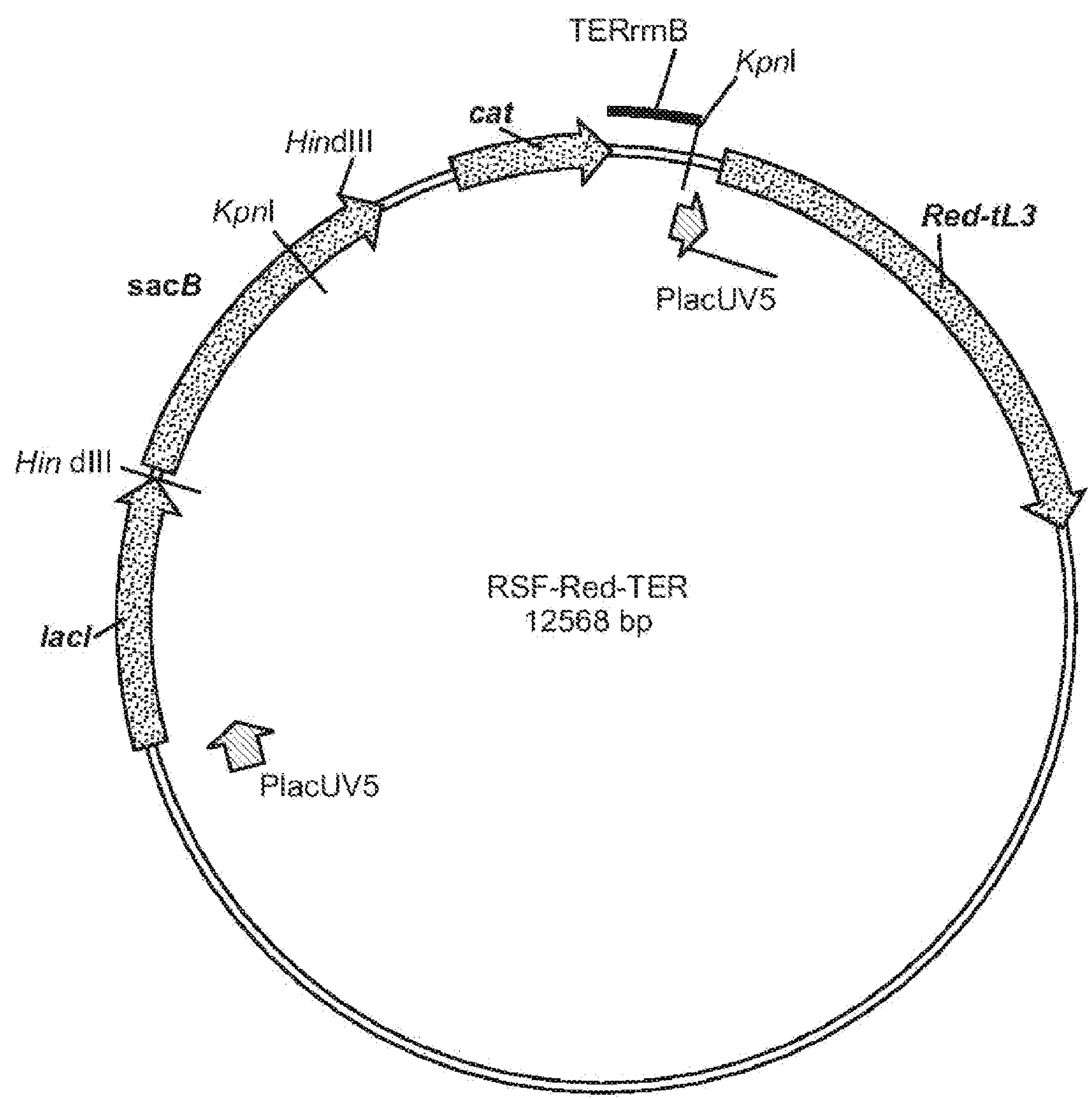
FIG. 1 shows the structure of the helper plasmid RSF-Red-TER.

The bacterium belongs to the family Enterobacteriaceae and is able to produce L-cysteine. The bacterium has been modified so that the activity of the protein encoded by the d0191 gene is decreased. The d0191 gene will be described herein.

The ability to produce L-cysteine means that the bacterium is able to produce and cause accumulation of L-cysteine in a medium or the bacterial cells in such an amount that the L-cysteine can be collected from the medium or cells when the bacterium is cultured in the medium. A bacterium having L-cysteine-producing ability means a bacterium which can produce and cause accumulation of a larger amount of L-cysteine in a medium as compared to a wild-type, parent, or unmodified strain. The L-cysteine is present after culture of the bacterium in an amount of 0.3 g/L or more, more preferably 0.4 g/L or more, and particularly preferably 0.5 g/L or more.

Some of the L-cysteine produced by the bacterium may change into L-cystine in the medium by the formation of a disulfide bond. Furthermore, as described later, S-sulfocysteine may be generated by the reaction of L-cysteine and thiosulfuric acid which are present in the medium (Szczepkowski T. W., Nature, vol. 182 (1958)). Furthermore, the L-cysteine that is generated in the bacterial cells may be condensed with a ketone, aldehyde, or, for example, pyruvic acid, which is also present in the cells, to produce a thiazolidine derivative via the intermediate hemithioketal (refer to Japanese Patent No. 2992010). The thiazolidine derivative and hemithioketal may exist as an equilibrated mixture. Therefore, the L-cysteine-producing ability is not limited to the ability to accumulate only L-cysteine in the medium or cells, but also includes the ability to accumulate L-cystine or derivatives thereof such as S-sulfocysteine, a thiazolidine derivative, a hemithioketal, or a mixture thereof in the medium.

The bacterium having L-cysteine-producing ability may inherently be able to produce L-cysteine, or this ability may be obtained by modifying a microorganism such as those described below by mutagenesis or a recombinant DNA technique so that the microorganism has L-cysteine-producing ability. The term L-cysteine refers to the reduced type L-cysteine, L-cystine, and derivatives such as those mentioned above or a mixture thereof, unless specifically denoted otherwise.

The bacterium is not particularly limited so long as the bacterium belongs to the family Enterobacteriaceae such as those of the genera *Escherichia, Enterobacter, Pantoea, Klebsiella, Serratia, Erwinia, Salmonella*, and *Morganella*, and has L-cysteine-producing ability. Specifically, bacteria classified into the family Enterobacteriaceae according to the taxonomy used in the NCBI (National Center for Biotechnology Information) database (http://www.ncbi.nlm.nih.gov/Taxonomy/Browser/wwwtax.cgi?id=91347) can be used. The parent, wild-type, or unmodified strain of the family Enterobacteriaceae which can be used for the modification is, preferably, a bacterium of the genus *Escherichia, Enterobacter, Pantoea, Erwinia*, or *Klebsiella.*

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. *Escherichia coli* is preferable. Examples of *Escherichia coli* include *Escherichia coli* W3110 (ATCC 27325), *Escherichia coli* MG1655 (ATCC 47076) and so forth, which are derived from the prototype wild-type strain, K12 strain.

These strains are available from, for example, the American Type Culture Collection (Address: 12301 Parklawn Drive, Rockville, Md. 20852, P.O. Box 1549, Manassas, Va. 20108, United States of America). That is, registration numbers are given to each of the strains, and the strains can be ordered by using these registration numbers (refer to http://www.atcc.org/). The registration numbers of the strains are listed in the catalogue of the American Type Culture Collection.

Examples of the *Enterobacter* bacteria include *Enterobacter agglomerans, Enterobacter aerogenes* and so forth, and examples of the *Pantoea* bacteria include *Pantoea* ananatis. Some strains of *Enterobacter agglomerans* were recently reclassified into *Pantoea* agglomerans, *Pantoea ananatis*, or *Pantoea stewartii* on the basis of nucleotide sequence analysis of the 16S rRNA etc. A bacterium belonging to any of the genus *Enterobacter* or *Pantoea* may be used so long as it is a bacterium classified into the family Enterobacteriaceae.

In particular, *Pantoea, Erwinia*, and *Enterobacter* bacteria are classified as γ-proteobacteria, and they are taxonomically very similar to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39:337-345). Furthermore, some bacteria belonging to the genus *Erwinia* were reclassified as *Pantoea ananas* or *Pantoea* stewartii (refer to Int. J. Syst. Bacteriol., 1993, 43:162-173).

Examples of the *Enterobacter* bacteria include, but are not limited to, *Enterobacter agglomerans, Enterobacter aerogenes*, and so forth. Specifically, the strains exemplified in European Patent Publication No. 952221 can be used.

An exemplary strain of the genus *Enterobacter* is the *Enterobacter* agglomeranses ATCC 12287 strain.

Exemplary strains of the *Pantoea* bacteria include, but are not limited to, *Pantoea* ananatis, *Pantoea stewartii, Pantoea* agglomerans, and *Pantoea citrea.*

Specific examples of *Pantoea ananatis* strains include AJ13355, SC17, and SC17(0). The SC17 strain is a low phlegm-producing mutant strain derived from the AJ13355 strain (FERM BP-6614), and was isolated from soil in Iwata-shi, Shizuoka-ken, Japan. This strain can proliferate in a low pH medium containing L-glutamic acid and a carbon source (U.S. Pat. No. 6,596,517). The SC17(0) strain was constructed to be resistant to the λ Red gene product for performing gene disruption in *Pantoea ananatis* (refer to Reference Example 1).

The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was identified as *Enterobacter agglomerans* when it was isolated and deposited, and given the private number AJ13355. However, this strain was recently reclassified as *Pantoea ananatis* on the basis of nucleotide sequencing of the 16S rRNA and so forth.

Examples of the *Erwinia* bacteria include, but are not limited to, *Erwinia amylovora* and *Erwinia carotovora*, and examples of the *Klebsiella* bacteria include *Klebsiella planticola.*

Hereinafter, methods for imparting L-cysteine-producing ability to bacteria belonging to Enterobacteriaceae, or methods for enhancing L-cysteine-producing ability of such bacteria, are described.

To impart the ability to produce L-cysteine, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an analogue-resistant strain, or a metabolic regulation mutant, or by constructing a recombinant strain so that it overexpresses an L-cysteine biosynthesis enzyme. Here, in the breeding of an L-cysteine-producing bacteria, one or more of the above described properties may be imparted. The expression of L-cysteine biosynthesis enzyme(s) can be enhanced alone or in combinations of two or more. Furthermore, imparting properties such as an auxotrophic mutation, analogue resistance, or metabolic regulation mutation may be combined with the methods of enhancing the biosynthesis enzymes.

An auxotrophic mutant strain, L-cysteine analogue-resistant strain, or metabolic regulation mutant strain with the ability to produce L-cysteine can be obtained by subjecting a parent, wild-type, or unmodified strain to conventional mutagenesis, such as exposure to X-rays or UV irradiation, or by treating with a mutagen such as N-methyl-N'-nitro-N-nitrosoguanidine, etc., then selecting those which exhibit autotrophy, analogue resistance, or a metabolic regulation mutation and which also have the ability to produce L-cysteine.

Specific examples of L-cysteine-producing bacteria include, but are not limited to, *E. coli* JM 15 transformed with multiple kinds of cysE gene alleles encoding serine acetyltransferase resistant to feedback inhibition (U.S. Pat. No. 6,218,168), *E. coli* W3110 in which a gene encoding a protein responsible for excretion of cytotoxic substances is overexpressed (U.S. Pat. No. 5,972,663), an *E. coli* strain having decreased cysteine desulfhydrase activity (Japanese Patent Laid-open No. 11-155571), and *E. coli* W3110 with increased activity of the positive transcriptional control factor of the cysteine regulon encoded by the cysB gene (WO01/27307).

The bacterium is modified to decrease the activity of the protein encoded by the d0191 gene. This protein has cysteine desulfhydrase activity. The following proteins are known to have the cysteine desulfhydrase activity of *E. coli*: cystathionine-β-lyase (metC product, Japanese Patent Laid-open No. 11-155571, Chandra et al., Biochemistry, 21 (1982) 3064-3069), tryptophanase (tnaA product, Japanese Patent Laid-open No. 2003-169668, Austin Newton et al., J. Biol. Chem., 240 (1965) 1211-1218)), O-acetylserine sulfhydrylase B (cysM gene product, Japanese Patent Laid-open No. 2005-245311) and the malY gene product (Japanese Patent Laid-open No. 2005-245311). In addition to decreasing the activity of the protein encoded by the d0191 gene, the activities of these proteins may be decreased.

The L-cysteine-producing bacterium preferably has a SAT which has been mutated to be resistant to feedback inhibition. The following mutations in SAT are known to induce resistance to feedback inhibition and are derived from *Escherichia coli*: when the methionine residue at position 256 is replaced with a glutamate residue (Japanese Patent Laid-open No. 11-155571), when the methionine residue at position 256 is replaced with an isoleucine residue (Denk, D. and Boeck, A., J. General Microbiol., 133, 515-525 (1987)), a mutation in the region from the amino acid residue at position 97 to the amino acid residue at position 273 or a deletion of the C-terminus region from the amino acid residue at position 227 (International Patent Publication WO97/15673, U.S. Pat. No. 6,218, 168), when the amino acid sequence corresponding to positions 89 to 96 of wild-type SAT contains one or more mutations (U.S. Patent Published Application No. 20050112731(A1)) and so forth. In the cysE5 gene which encodes the mutant SAT described in the examples, the Val residue and the Asp residue at positions 95 and 96 of the wild-type SAT are replaced with an Arg residue and Pro residue, respectively.

The SAT gene is not limited to the gene of *Escherichia coli*, but can be any gene encoding a protein having the SAT activity. An SAT isozyme of *Arabidopsis thaliana* and desensitized to feedback inhibition by L-cysteine is known, and the gene encoding this SAT can also be used (FEMS Microbiol. Lett., 179 (1999) 453-459).

If a gene encoding a mutant SAT is introduced into a bacterium, L-cysteine-producing ability is imparted to the bacterium. To introduce a mutant SAT gene into a bacterium, various vectors which are typically used for protein expression can be used. Examples of such vectors include pUC19, pUC18, pHSG299, pHSG399, pHSG398, RSF1010, pBR322, pACYC184, pMW219, and so forth.

In order to introduce a recombinant vector containing a SAT gene into a bacterium, methods which are typically used to transform bacteria can be used, such as the method of D. A. Morrison (Methods in Enzymology, 68, 326 (1979)), treating recipient cells with calcium chloride to increase permeability of the cells for DNA (Mandel, M. and Higa, A., J. Mol. Biol., 53, 159 (1970)), and a method based on electroporation.

Furthermore, the SAT activity can also be enhanced by increasing the copy number of the SAT gene. The copy number of the SAT gene can be increased by introducing the SAT gene into a bacterium by using a vector such as those described above, or by introducing multiple copies of the SAT gene onto the chromosomal DNA of a bacterium. Multiple copies of the SAT gene are introduced by homologous recombination which targets a sequence present on the chromosomal DNA in a multiple copies. A repetitive DNA or inverted repeat present at the end of a transposable element can be used as a sequence which is present on the chromosomal DNA in a multiple copies. Alternatively, as disclosed in Japanese Patent Laid-open No. 2-109985, multiple copies of the SAT gene can be introduced into the chromosomal DNA by incorporating them into a transposon and transferring it.

The bacterium can be obtained by modifying a *Enterobacteriaceae* bacterium which is able to produce cysteine so that the activity of the protein encoded by the d0191 gene (henceforth also referred to as "D0191") is decreased. Alternatively, after modifying the bacterium so that the activity of the D0191 protein is decreased, the L-cysteine-producing ability may then be imparted.

A novel gene encoding a protein having cysteine desulfhydrase activity from the chromosomal DNA of *Pantoea ananatis* has been found, and has been designated the d0191 gene. The nucleotide sequence of this gene and the amino acid sequence encoded by the gene are shown in SEQ ID NOS: 1 and 2, respectively.

When databases were searched for the sequence of the d0191 gene of *Pantoea ananatis*, homologous genes to the d0191 gene were found in the following bacteria, although their functions were unknown. The nucleotide sequences of these genes and their encoded amino acid sequences are shown in SEQ ID NOS: 34 to 52. Accession numbers in the NCBI (National Center for Biotechnology Information) database are shown in the parentheses (GenBank Identifier(gi) |RefSeq accession (ref)).

*Citrobacter koseri* ATCC BAA-895 (accession: gi|157146936|ref|YP_001454255.1|)

*Klebsiella pneumoniae* subsp. *pneumoniae* MGH 78578 (accession: gi|152968982|ref|YP_001334091.1|)

*Enterobacter* sp. 638 (accession: gi|146310575|ref|YP_001175649.1|)

*Salmonella typhimurium* LT2 (accession: gi|16763839|ref|NP_459454.1|)

*Serratia* proteamaculans 568 (accession: gi|57369348|ref|YP_001477337.1|)

*Erwinia carotovora* subsp. *atroseptica* SCR11043 (accession: gi|50120095|ref|YP_049262.1|)

*Vibrio cholerae* O1 biovar eltor str. N16961 (accession: gi|15641074|ref|NP_230706.1|)

*Pseudomonas fluorescens* PfO-1 (accession: gi|77457462|ref|YP_346967.1|)

*Streptomyces coelicolor* A3(2) (accession: gi|21219544|ref|NP_625323.1|)

*Mycobacterium avium* 104 (accession: gi|118467280|ref|YP_879726.1|)

In the present invention, the d0191 gene of *Pantoea ananatis* and it's homologues which are native to, or derived from, other bacteria are also encompassed by the term 'the d0191 gene'.

The phrase "decrease the activity of the protein encoded by the d0191 gene" means that the activity of the D0191 protein encoded by the d0191 gene is decreased as compared to a non-modified strain such as a wild-type strain or parent strain, and may also mean the complete disappearance of the activity.

As described in the examples, it was demonstrated that the protein encoded by the d0191 gene, i.e., the D0191 protein, has cysteine desulfhydrase activity by staining. Therefore, the activity of the D0191 protein specifically means cysteine desulfhydrase activity. The cysteine desulfhydrase activity can be measured by, for example, the method described in Japanese Patent Laid-open No. 2002-233384.

Modifications which result in a decrease in the activity of the D0191 protein include, for example, reducing expression of the d0191 gene. Specifically, for example, intracellular activity of the protein can be reduced by deleting a part or all of the coding region of the d0191 gene on the chromosome. Furthermore, the activity of the D0191 protein can also be decreased by reducing the expression by, for example, modifying an expression control sequence of the gene such as promoter or Shine-Dalgarno (SD) sequence. Furthermore, the expression of the gene can also be reduced by modifying a non-translated region other than an expression control sequence. Furthermore, the whole gene including the sequences on both sides of the gene on the chromosome may be deleted. Furthermore, a decrease in activity can also be attained by introducing a mutation for an amino acid substitution (missense mutation), a stop codon (nonsense mutation), or a frame shift mutation which adds or deletes one or two nucleotides into the coding region of the d0191 gene on the chromosome (Journal of Biological Chemistry, 272: 8611-8617 (1997); Proceedings of the National Academy of Sciences, USA, 95 5511-5515 (1998); Journal of Biological Chemistry, 266, 20833-20839 (1991)).

Furthermore, a transcriptional regulator gene which is involved in regulating the expression of the d0191 gene of the *Pantoea ananatis* SC17 strain may be used. This gene was named c0263. The ORF of the c0263 gene is located 80 bp upstream from the d0191 ORF in the opposite direction as the d0191. The c0263 gene is thought to be a homolog of the ybaO gene, which has been found in bacteria such as *E. coli*, by homology searches and encodes a translation regulator. The activity of the d0191 protein can be decreased by inactivating the ybaO gene. Additionally, both the c0263 and d0191 genes may be deleted. The nucleotide sequence of the d0191 gene from *Pantoea ananatis* and the amino acid sequence encoded by the gene are shown in SEQ ID NOS: 66 and 67, respectively.

Furthermore, modifications can be made by conventional mutagenesis using X-ray or ultraviolet irradiation, or via the use of a mutagen such as N-methyl-N'-nitro-N-nitrosoguanidine, so long as the modification results in a decrease in the activity of the D0191 protein.

One or more nucleotides, more preferably two or more nucleotides, particularly preferably three or more nucleotides in the expression control sequence can be modified. When deletions are made to the coding region, the deletions can be made in the N-terminus region, an internal region, or the C-terminus region, or even the entire coding region may be deleted, so long as the function of the d0191 protein is decreased or eliminated. The longer the region is that is deleted, the more likely inactivation of the gene will occur. Furthermore, it is preferred that reading frames upstream and downstream of the region to be deleted are not the same.

When another sequence is inserted into the coding region of the d0191 gene, the sequence may be inserted into any region of the gene, and the longer the sequence is that is inserted, the more likely the gene will be inactivated. It is preferred that reading frames upstream and downstream of the insertion site are not the same. The sequence that is inserted is not particularly limited so long as the function of the encoded D0191 protein is decreased or eliminated, and examples include a transposon carrying an antibiotic resistance gene, a gene useful for L-cysteine production and so forth.

The d0191 gene on the chromosome can be modified as described above, for example, by preparing a deletion-type version of the gene in which a partial sequence of the gene is deleted so that the deletion-type gene produces a non-functioning D0191 protein, and transforming a bacterium with a DNA containing the deletion-type gene to cause homologous recombination between the deletion-type gene and the native gene on the chromosome, and thereby substituting the deletion-type gene for the gene on the genome. The D0191 protein encoded by the deletion-type gene has a conformation different from that of the wild-type protein, if it is even produced, and thus the function is reduced or deleted. Gene disruption based on gene substitution utilizing homologous recombination is known, and includes the method called Red-driven integration (Datsenko, K. A, and Wanner, B. L., Proc. Natl. Acad. Sci. USA, 97:6640-6645 (2000)), use of a linear DNA in Red driven integration in combination with an excisive system derived from λ phage (Cho, E. H., Gumport, R. I., Gardner, J. F., J. Bacteriol., 184:5200-5203 (2002)), using a plasmid containing a temperature-sensitive replication origin or a plasmid capable of conjugative transfer, a method of utilizing a suicide vector not having replication origin in a host (U.S. Pat. No. 6,303,383, Japanese Patent Laid-open No. 05-007491), and so forth.

Decrease of the expression of the d0191 gene can be confirmed by comparing the amount of mRNA transcribed from the gene with that in a wild-type strain or non-modified strain. The expression can be confirmed by Northern hybridization, RT-PCR (Sambrook, J., Fritsch, E. F., and Maniatis, T. 1989, Molecular Cloning A Laboratory Manual/Second Edition, Cold Spring Harbor Laboratory Press, New York.), and the like.

A decrease of the amount of the D0191 protein can be confirmed by Western blotting using antibodies (Molecular cloning, Cold spring Harbor Laboratory Press, Cold spring Harbor, USA, 2001).

A decrease of the amount of the D0191 protein can also be confirmed by measuring the cysteine desulfhydrase activity in the cell.

Since the nucleotide sequence of the d0191 gene may different depending on the bacterial species or strain that is chosen, the d0191 gene to be modified may be a variant of the nucleotide sequence of SEQ ID NO: 1. Moreover, the d0191 gene to be modified may be any of the aforementioned d0191 gene homologues, for example, a variant of a gene having the nucleotide sequence shown as SEQ ID NOS: 33, 35, 37, 39, 41, 43, 45, 47, 49, or 51.

Variants of the d0191 gene can be found by using BLAST to search (http://blast.genome.jp/) by referring to the nucleotide sequence of SEQ ID NO: 1 or SEQ ID NO: 33, 35, 37, 39, 41, 43, 45, 47, 49, or 51. Moreover, variants of the d0191 gene include genes which can be amplified by PCR using the chromosome of bacterium belonging to the family Enterobacteriaceae or the like as the template, and synthetic oligonucleotides prepared on the basis of the nucleotide sequence of SEQ ID NO: 1, SEQ ID NO: 33, 35, 37, 39, 41, 43, 45, 47, 49, or 51.

Moreover, the d0191 gene may also encode a protein having a sequence corresponding to the amino acid sequence of the D0191 protein, such as the sequence of SEQ ID NO: 2, SEQ ID NO: 34, 36, 38, 40, 42, 44, 46, 48, 50 or 52, including substitutions, deletions, insertions, additions, or the like of one or several amino acid residues at one or several positions. Although the number of the "one or several" amino acid residues may differ depending on their position in the three-dimensional structure or the types of amino acid residues of the proteins, it is preferably 1 to 20, more preferably 1 to 10, particularly preferably 1 to 5. These substitutions, deletions, insertions, or additions of one or several amino acids are preferably conservative mutations so that the function of the protein in maintained. A conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Typical examples of conservative mutations are conservative substitutions. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion etc. may be the result of a naturally-occurring mutation or variation due to an individual difference, or a difference of species of a bacterium.

The d0191 gene encodes a protein having the amino acid sequence of SEQ ID NO: 2, or a protein having an amino acid sequence of SEQ ID NO: 2 which includes substitutions, deletions, insertions or additions of 1 to 50, preferably 1 to 40, more preferably 1 to 30, still more preferably 1 to 20, further still more preferably 1 to 10, particularly preferably 1 to 5, of amino acid residues, and has cysteine desulfhydrase activity.

Furthermore, the gene having such one or more conservative mutations as mentioned above may encode a protein showing a homology of 80% or more, preferably 90% or more, more preferably 95% or more, still more preferably 97% or more, further still more preferably 98% or more, particularly preferably 99% or more, to the entire encoded amino acid sequence, and which has a function equivalent to that of the wild-type D0191 protein. In the present specification, the term "homology" may mean "identity".

The d0191 gene may be a DNA which hybridizes with a probe prepared from known gene sequences, for example, the above described gene sequences or sequences complementary to the sequences under stringent conditions and which encode a protein which is a functional equivalent to the D0191 protein. The term "stringent conditions" refers to conditions where a so-called specific hybrid is formed and a non-specific hybrid is not formed. Examples thereof include conditions where DNAs having high homology, for example, at least 80%, preferably 90%, more preferably 95%, more preferably 97%, more preferably 98%, further preferably 99% homology, hybridize with each other and DNAs having homology less than the value do not hybridize with each other; and specifically include conditions corresponding to a salt concentration and temperature of washing which are typical of Southern hybridization, e.g., washing at 60° C., 1×SSC, 0.1% SDS, preferably 60° C., 0.1×SSC, 0.1% SDS, more preferably 68° C., 0.1×SSC, 0.1% SDS, once or preferably twice or three times.

The probe may be a partial sequence of the gene. Such a probe can be prepared by PCR using oligonucleotides prepared based on the known nucleotide sequences of genes as primers, and a DNA fragment containing these sequences as the template. When a DNA fragment of a length of about 300 bp is used as the probe, the conditions of washing after hybridization can be, for example, 50° C., 2×SSC, and 0.1% SDS.

The above descriptions about variants of genes and proteins are similarly applied to enzymes such as serine acetyltransferase and genes coding for them.

<2> Method for Producing L-Cysteine, L-Cystine, Derivatives Thereof, or Mixture Thereof These compounds can be produced by culturing the bacterium obtained as described above in a medium, and collecting L-cysteine, L-cystine, derivatives thereof, or a mixture thereof from the medium. Examples of a derivative of L-cysteine include S-sulfocysteine, a thiazolidine derivative, a hemithioketal corresponding the thiazolidine derivative mentioned above and so forth.

Examples of the medium used for the culture include ordinary media containing a carbon source, nitrogen source, sulfur source, inorganic ions, and other organic components as required.

As the carbon source, saccharides such as glucose, fructose, sucrose, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia, and so forth can be used.

As the sulfur source, inorganic sulfur compounds, such as sulfates, sulfites, sulfides, hyposulfites, and thiosulfates can be used.

As organic trace amount nutrients, it is desirable to add required substances such as vitamin $B_1$, yeast extract and so forth in appropriate amounts. Other than these, potassium phosphate, magnesium sulfate, iron ions, manganese ions, and so forth are added in small amounts.

The culture is preferably performed under aerobic conditions for 30 to 90 hours. The culture temperature is preferably controlled to be 25° C. to 37° C., and the pH is preferably controlled to be 5 to 8 during the culture. To adjust the pH, inorganic or organic acidic or alkaline substances, ammonia gas and so forth can be used. Collection of L-cysteine from the culture can be attained by, for example, any combination of known ion exchange resin methods, precipitation, and other known methods.

L-cysteine obtained as described above can be used to produce L-cysteine derivatives. The cysteine derivatives include methylcysteine, ethylcysteine, carbocysteine, sulfocysteine, acetylcysteine, and so forth.

Furthermore, when a thiazolidine derivative of L-cysteine is produced in the medium, L-cysteine can be produced by collecting the thiazolidine derivative from the medium to break the reaction equilibrium between the thiazolidine derivative and L-cysteine so that L-cysteine should be excessively produced.

Furthermore, when S-sulfocysteine is produced in the medium, it can be converted into L-cysteine by reduction with a reducing agent such as dithiothreitol.

EXAMPLES

Hereinafter, the present invention will be explained more specifically with reference to the following non-limiting examples.

Reference Example 1

Construction of *Pantoea ananatis* Strain which is Resistant to the λ Red Gene Product To disrupt the desired gene in *Pantoea ananatis*, a recipient strain was constructed which is able to efficiently carry out the method called "Red-driven integration" or "Red-mediated integration" (Proc. Natl. Acad. Sci. USA., 97, 6640-6645 (2000)).

First, the novel helper plasmid RSF-Red-TER was constructed. This plasmid expresses the gam, bet, and exo genes of λ (henceforth referred to as "λ Red gene") (FIG. 1). The details are described in Reference Example 2.

This plasmid can be used in a wide range of hosts having different genetic backgrounds. This is because 1) this plasmid has the replicon of the RSF110 wide-host spectrum plasmid (Scholz, et al., 1989; Buchanan-Wollaston et al., 1987), which may be stably maintained by many gram negative and gram positive bacteria, and even plants, 2) the λ Red genes, including the gam, bet, and exo genes, are under the control of the $P_{lacUV5}$ promoter, which is recognized by the RNA polymerases of many bacteria (for example, Brunschwig, E. and Darzins, A., Gene, 111, 1, 35-41 (1992); Dehio, M. et al, Gene, 215, 2, 223-229 (1998)), and 3) the autoregulation factor $P_{lacUV5}$-lacI and the ρ-non-dependent transcription terminator (TrrnB) of the rrnB operon of *Escherichia coli* lowers the basal expression level of the λ Red gene (Skorokhodova, A. Yu et al, Biotekhnologiya (Rus), 5, 3-21 (2004)). Furthermore, the RSF-Red-TER plasmid contains the levansucrase gene (sacB), and by using this gene, the plasmid can be collected from cells in a medium containing sucrose.

In *Escherichia coli*, the frequency of integration of a PCR-generated DNA fragment and the short flanking region provided by the RSF-Red-TER plasmid is high, and is typically to the same extent as when the pKD46 helper plasmid is used (Datsenko, K A., Wanner, B. L., Proc. Natl. Acad. Sci. USA, 97, 6640-6645 (2000)). However, expression of the λ Red gene is toxic to *Pantoea ananatis*. The cells transformed with the RSF-Red-TER helper plasmid grew extremely slowly in LB medium containing IPTG (isopropyl-β-D-thiogalactopyranoside, 1 mM) and an appropriate antibiotic (25 μg/ml of chloramphenicol or 40 μg/ml of kanamycin), and the efficiency of λ Red-mediated recombination is extremely low ($10^{-8}$), if observed at all.

A variant strain of *Pantoea ananatis* which is resistant to expression of all of the λ Red genes was selected. For this purpose, the RSF-Red-TER plasmid was introduced into the *Pantoea* ananatis SC17 strain (U.S. Pat. No. 6,596,517) by electroporation. After an 18 hour culture, about $10^6$ transformants were obtained, and among these, 10 clones formed colonies of large size, and the remainder formed extremely small colonies. After an 18 hour culture, the large colonies had a size of about 2 mm, and the small colonies had a size of about 0.2 mm. Whereas the small colonies did not grow any more even if the culture was extended until another 24 hours, the large colonies continued to grow. One of the large colony *Pantoea ananatis* variant strains which was resistant to expression of all the λ Red genes (gam, bet, and exo) was used for the further analysis.

The RSF-Red-TER plasmid DNA was isolated from one clone of the large colony clones, and from several clones of the small colonies, and transformed again into *Escherichia coli* MG1655 to examine the ability of the plasmid to synthesize an active Red gene product. By a control experiment for Red-dependent integration in the obtained transformants, it was demonstrated that only the plasmid isolated from the large colony clone induced expression of the λ Red gene required for the Red-dependent integration. In order to investigate whether the Red-mediated integration occurs in the selected large colony clone, electroporation was performed by using a linear DNA fragment produced by PCR. This fragment was designed so that it contains a $Km^R$ marker and a flanking region of 40 bp homologous to the hisD gene. This fragment is integrated into the hisD gene of *Pantoea ananatis* at the SmaI recognition site. Two small colony clones were used as a control. The nucleotide sequence of the hisD gene of *Pantoea ananatis* is shown in SEQ ID NO: 3. For PCR, the oligonucleotides of SEQ ID NOS: 4 and 5 were used as primers, and the pMW118-(λatt-$Km^r$-λatt) plasmid was used as the template. The two small colony clones which were not resistant to the λ Red gene were used as a control. Construction of the pMW118-(λattL-Kmr-λattR) plasmid will be explained in detail in Reference Example 3.

The RSF-Red-TER plasmid can induce expression of the Red gene when the lac gene is present on the plasmid. Two kinds of induction conditions were investigated. In the first group, IPTG (1 mM) was added 1 hour before the electroporation, and in the second group, IPTG was added at the start of the culture. The growth rate of the cells harboring RSF-Red-TER derived from the large colony clone was not significantly lower than that of a strain not having the SC17 plasmid. The addition of IPTG only slightly decreased the growth rate of these cultures. On the other hand, the progeny of the small colony clones grew extremely slowly even without the addition of IPTG, and after induction, growth was substantially arrested. After electroporation of the cells of the progeny of the large colony clone, many $Km^R$ clones grew (18 clones after a short induction time, and about 100 clones after an extended induction time). All the 100 clones that were investigated had a $His^-$ phenotype, and about 20 clones were confirmed by PCR to have the expected structure of chromosome in the cells. On the other hand, even when electroporation was performed with the progeny of the small colony clones, an integrated strain was not obtained.

The large colony clone was grown on a plate containing 7% sucrose to eliminate the plasmid, and transformed again with RSF-Red-TER. The strain without the plasmid was designated SC17(0). This strain was deposited at the Russian National Collection of Industrial Microorganisms (VKPM, GNII Genetica, address: Russia, 117545 Moscow, 1 Dorozhny proezd. 1) on Sep. 21, 2005, and assigned an accession number of VKPM B-9246.

All the clones which grew after the aforementioned re-transformation showed large colony sizes like the parent strain clone SC17(0). The Red-mediated integration experiment was performed in the SC17(0) strain re-transformed with the RSF-Red-TER plasmid. Three of the independent transformants were investigated by using the same DNA fragment as that used for the previous experiment. The short induction time (1 hour before electroporation) was employed. $Km^R$ clones exceeding ten clones grew in each experiment. All the examined clones had the His-phenotype. In this way, a variant strain designated SC17(0) resistant to the expression of the λ Red gene was selected. This strain can be used as a recipient strain suitable for the Red-dependent integration into the *Pantoea ananatis* chromosome.

Reference Example 2

Construction of Helper Plasmid RSF-Red-TER

Figure 2:
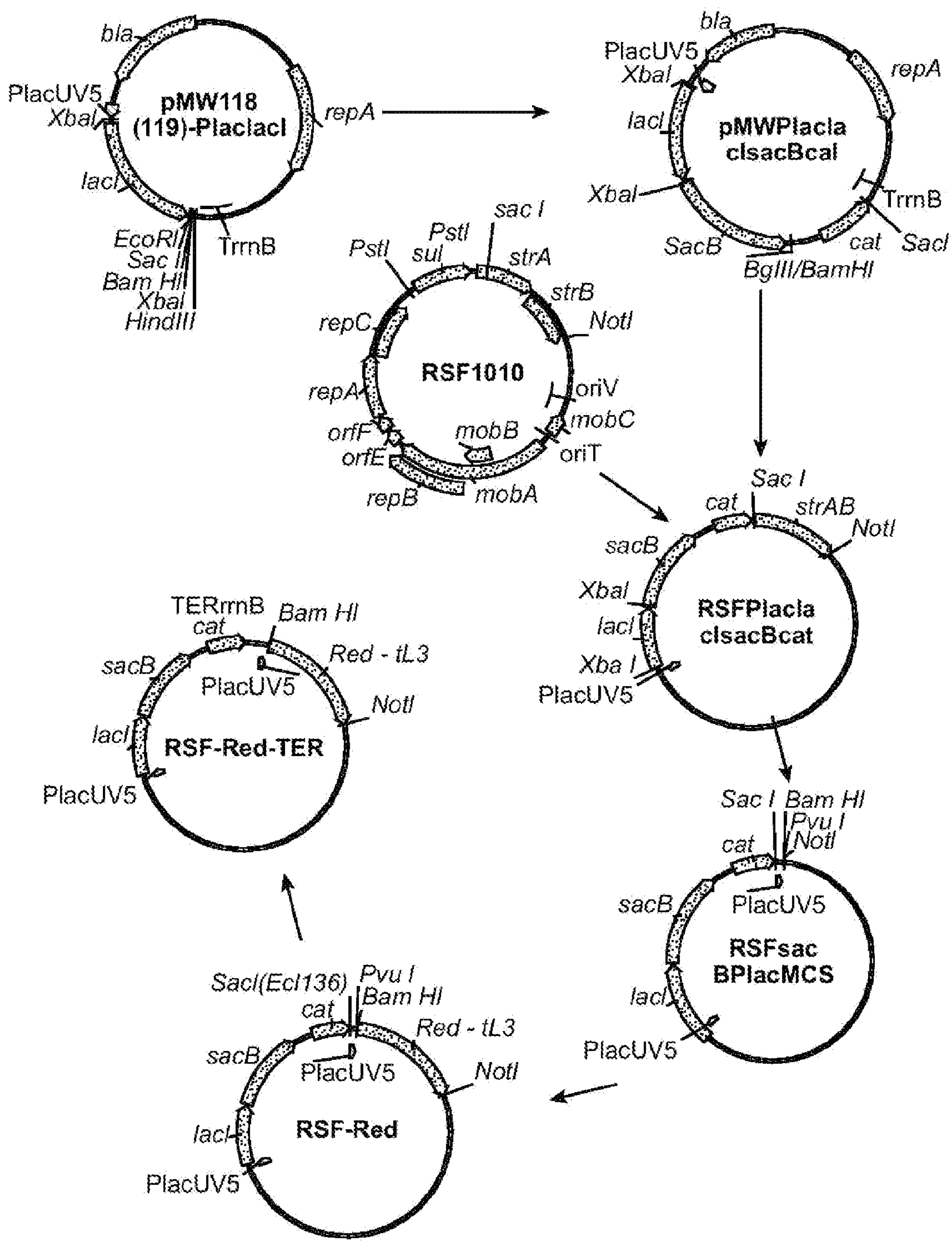
FIG. 2 shows the construction of the helper plasmid RSF-Red-TER.

The construction scheme of the helper plasmid RSF-Red-TER is shown in FIG. 2.

As a first step of the construction, a RSFsacBPlacMCS vector was designed. For this purpose, DNA fragments containing the cat gene of the pACYC184 plasmid and the structural gene region of the sacB gene of *Bacillus subtilis* were amplified by PCR using the oligonucleotides of SEQ ID NOS: 6 and 7, and 8 and 9, respectively. These oligonucleotides contained convenient BglII, SacI, XbaI, and BamHI restriction enzyme sites required for further cloning in the 5' end regions, respectively. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Yu et al, Biotekhnologiya (Rus), 5, 3-21 (2004)). However, this vector contained a polylinker moiety derived from pMW219 instead of the pMW218 plasmid.

Then, the aforementioned cat fragment of 1.0 kb was treated with BglII and SacI, and cloned into the RSF-$P_{lac}$lacIsacB plasmid obtained in the previous step at the BamHI-SacI site. The obtained plasmid PMW-$P_{lac}$lacIsacBcat contained the PlacUV5-lacI-sacB-cat fragment. In order to subclone this fragment into the RSF1010 vector, PMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from 1% agarose gel, and ligated with the RSF1010 vector which had been treated with PstI and SacI. *Escherichia coli* TG1 was transformed with the ligation mixture, and plated on the LB medium containing chloramphenicol (50 mg/L). The plasmids isolated from the grown clones were analyzed with restriction enzymes to obtain RSFsacB. In order to construct a RSFsacBP$_{lac}$MCS vector, a DNA fragment containing the $P_{lacUV5}$ promoter was amplified by PCR using oligonucleotides of SEQ ID NOS: 10 and 11 as primers and the pMW119-$P_{lac}$lacI plasmid as the template. The obtained fragment of 146 bp was digested with SacI and NotI, and ligated with the SacI-NotI large fragment of the RSFsacB plasmid. Then, by PCR using the oligonucleotides of SEQ ID NOS: 12 and 13 as primers, and the pKD46 plasmid (Datsenko, K A., Wanner, B. L., Proc. Natl. Acad. Sci. USA, 97, 6640-6645 (2000)) as the template, a DNA fragment of 2.3 kb containing the λRedαβγ gene and the transcription terminator tL3 was amplified. The obtained fragment was cloned into the RSFsacBP$_{lac}$MCS vector at the PvuI-NotI site. In this way, the RSFRed plasmid was designed.

In order to eliminate the read through transcription of the Red gene, a ρ-dependent transcription terminator of the rrnB operon of *Escherichia coli* was inserted at the position between the cat gene and the $P_{lacUV5}$ promoter. For this purpose, a DNA fragment containing the PlacUV5 promoter and the TrrnB terminator was amplified by PCR using the oligonucleotides of SEQ ID NOS: 14 and 11 as primers and the chromosome of *Escherichia coli* BW3350 as the template.

These obtained fragments were treated with KpnI and ligated. Then, the 0.5 kb fragment containing both $P_{lacUV5}$ and TrrnB was amplified by PCR using the oligonucleotides of SEQ ID NOS: 11 and 15 as primers. The obtained DNA fragment was digested with EcoRI, blunt-ended with DNA polymerase I Klenow fragment, digested with BamHI, and ligated with the Ecl136II-BamHI large fragment of the RSFsacBPlacMCS vector. The obtained plasmid was designated RSF-Red-TER.

Reference Example 3

Construction of the pMW118-(λattL-Km$^r$-λattR) plasmid

The pMW118-(λattL-Km$^r$-λattR) plasmid was constructed based on the pMW118-attL-Tc-attR (WO2005/010175) plasmid by replacing the tetracycline resistance marker gene with the kanamycin resistance marker gene from the pUC4K plasmid (Vieira, J. and Messing, J., *Gene,* 19(3): 259-68 (1982)). For that purpose, the large EcoRI-HindIII fragment from pMW118-attL-Tc-attR was ligated to two fragments from the pUC4K plasmid: HindIII-PstI (676 bp) and EcoRI-HindIII (585 bp). Basic pMW118-attL-Tc-attR was obtained by ligation of the following four DNA fragments:

1) the BglII-EcoRI fragment (114 bp) including attL (SEQ ID NO: 26) which was obtained by PCR amplification of the corresponding region of the *E. coli* W3350 (contained λ prophage) chromosome using oligonucleotides P1 and P2 (SEQ ID NOS: 53 and 54) as primers (these primers contained the subsidiary recognition sites for BglII and EcoRI endonucleases);
2) the PstI-HindIII fragment (182 bp) including attR (SEQ ID NO: 58) which was obtained by PCR amplification of the corresponding region of the *E. coli* W3350 (contained λ prophage) chromosome using the oligonucleotides P3 and P4 (SEQ ID NOS: 56 and 57) as primers (these primers contained the subsidiary recognition sites for PstI and HindIII endonucleases);
3) the large BglII-HindIII fragment (3916 bp) of pMW118-ter_rrnB. The plasmid pMW118-ter_rrnB was obtained by ligation of the following three DNA fragments:
a) the large DNA fragment (2359 bp) including the AatII-EcoRI fragment of pMW118 that was obtained by digesting pMW118 with EcoRI restriction endonuclease, treating with Klenow fragment of DNA polymerase I, and then digesting with AatII restriction endonuclease;
b) the small AatII-BglII fragment (1194 bp) of pUC19 including the bla gene for ampicillin resistance ($Ap^R$) was obtained by PCR amplification of the corresponding region of the pUC19 plasmid using oligonucleotides P5 and P6 (SEQ ID NOS: 59 and 60) as primers (these primers contained the subsidiary recognition sites for AatII and BglII endonucleases);
c) the small BglII-PstIpol fragment (363 bp) of the transcription terminator ter_rrnB was obtained by PCR amplification of the corresponding region of the *E. coli* MG1655 chromosome using oligonucleotides P7 and P8 (SEQ ID NOS: 61 and 62) as primers (these primers contained the subsidiary recognition sites for BglII and PstI endonucleases);
4) the small EcoRI-PstI fragment (1388 bp) (SEQ ID NO: 63) of pML-Tc-ter_thrL including the tetracycline resistance gene and the ter_thrL transcription terminator; the pML-Tc-ter_thrL plasmid was obtained in two steps:
the pML-ter_thrL plasmid was obtained by digesting the pML-MCS plasmid (Mashko, S. V. et al., Biotekhnologiya (in Russian), 2001, no. 5, 3-20) with the XbaI and BamHI restriction endonucleases, followed by ligation of the large fragment (3342 bp) with the XbaI-BamHI fragment (68 bp) including terminator ter_thrL obtained by PCR amplification of the corresponding region of the *E. coli* MG1655 chromosome using oligonucleotides P9 and P10 (SEQ ID NOS: 64 and 65) as primers (these primers contained the subsidiary recognition sites for the XbaI and BamHI endonucleases);
the pML-Tc-ter_thrL plasmid was obtained by digesting the pML-ter_thrL plasmid with the KpnI and XbaI restriction endonucleases followed by treatment with Klenow fragment of DNA polymerase I and ligation with the small EcoRI-Van91I fragment (1317 bp) of pBR322 including the tetracycline resistance gene (pBR322 was digested with EcoRI and Van91I restriction endonucleases and then treated with Klenow fragment of DNA polymerase I).

Example 1

(1) Cloning of d0191 Gene from *P. ananatis* SC17 Strain

By PCR using the genomic DNA of *P. ananatis* SC17 strain (U.S. Pat. No. 6,596,517) as the template, primers d0191 (Pa)-FW (CGCGGATCCAAGCTTTTCATTATCCAGCAGAGCG, SEQ ID NO: 16), and d0191 (Pa)-RV (CGCGGATCCTAATGCTGTAGGGCCTGAACCAG, SEQ ID NO: 17), a d0191 gene fragment containing 300 bp upstream and 200 bp downstream from the d0191 gene was obtained. Restriction enzyme BamHI sites were designed at the 5' ends of these primers. For PCR, Pyrobest polymerase (Takara) was used, and after a reaction at 94° C. for 5 minutes, a cycle of 98° C. for 5 seconds, 55° C. for 5 seconds and 72° C. for 1 minute and 30 seconds was repeated 30 times in the standard reaction composition described in the protocol of the polymerase to amplify the target fragment of about 1.6 kb. The obtained fragment was treated with BamHI and inserted into pSTV29 (Takara) at the BamHI site (in the same direction as the lacZ gene on the vector) to obtain a plasmid pSTV-d0191F (having a chloramphenicol resistance marker) in which d0191 was cloned. The same PCR fragment was also inserted into pACYC177 (Nippon Gene) at the BamHI site (in the same direction as the kanamycin resistance gene on the vector) to obtain the plasmid pACYC-d0191F (having a kanamycin resistant marker). It was confirmed by sequencing that there was no PCR error. In this way, plasmids with two different antibiotic resistance markers and the same d0191 region (both had the same p15A origin) were prepared. Furthermore, pHSG-d0191F was prepared, which corresponds to the high copy vector pHSG299 (Takara) in which the same DNA fragment of about 1.6 kb as mentioned above was inserted at the BamHI site in the same direction as the kanamycin resistant marker and the lacZ gene on the vector.

(2) Construction of d0191-Enhanced Strains from *P. ananatis* SC17 Strain (SC17/pSTV-d0191F, SC17/pHSG-d0191F)

*P. ananatis* SC17 was transformed with the pSTV-d0191F plasmid which was constructed as described above to prepare a d0191-enhanced strain, SC17/pSTV-d0191F. As a control strain, a strain transformed with the empty vector, SC17/pSTV29, was also prepared. Furthermore, a d0191-enhanced strain, SC17/pHSG-d0191F, was also prepared by transforming *P. ananatis* SC17 with the high copy pHSG-d0191F. As a control strain, a strain transformed with the empty vector, SC17/pHSG299, was also prepared. The transformation of *P.*

*ananatis* was performed by a conventional method based on electroporation, and selection of the transformants was performed on LB agar medium (5 g/L of yeast extract, 10 g/L of tryptone, 10 g/L of sodium chloride, 15 g/L of agar) containing an antibiotic corresponding to the antibiotic resistance marker of the plasmid (25 mg/L in the case of chloramphenicol, 20 mg/L in the case of kanamycin).

(3) Construction of a d0191-Enhanced Strain from *E. coli* MG1655 Strain (MG1655/pSTV-d0191F)

*E. coli* MG1655 was transformed with the plasmid pSTV-d0191F which was constructed as described above to prepare a d0191-enhanced strain, MG1655/pSTV-d0191F. As a control strain, a strain transformed with the empty vector, MG1655/pSTV29, was also prepared. The transformation of *E. coli* was performed by a conventional method based on electroporation, and selection of the transformants was performed on LB agar medium (5 g/L of yeast extract, 10 g/L of tryptone, 10 g/L of sodium chloride, 15 g/L of agar) containing an antibiotic corresponding to the antibiotic resistance marker of the plasmid (25 mg/L in the case of chloramphenicol, 20 mg/L in the case of kanamycin).

(4) Construction of d0191-deficient Strains from *P. ananatis* SC17 Strain (SC17 d0191::$Km^r$ Strain, SC17 Dd0191 Strain)

Deletion of the d0191 gene was performed by "Red-driven integration", first developed by Datsenko and Wanner (Proc. Natl. Acad. Sci. USA, 2000, vol. 97, No. 12, pp. 6640-6645). According to the "Red-driven integration" method, a gene-disrupted strain can be constructed in one step using a PCR product obtained with synthetic primers in which a part of a target gene is present on the 5' side, and a part of antibiotic resistance gene is present on the 3' side, respectively DNA fragment with sequences homologous to each end of the d0191 gene flanking an antibiotic resistance gene (kanamycin resistance gene) was obtained by PCR. The primers Dd0191-FW (CCGTGTCTGAAGCCTATTTGCCCGCCT-GCTGGGCTTGCCTTTTATTGCCTGAAGCCT GCTTTTTTATACTAAGTTGGCA, SEQ ID NO: 18), and Dd0191-RV (CTAGCCCAGTTCGCGCTGCCAGGGCG-TAATATCGCCAATGTGCTCGGCAACGCTCA AGT-TAGTATAAAAAAGCTGAACGA, SEQ ID NO: 19) were used, and pME118-(λ attL-$Km^r$-λattR) (WO2006/093322A2, SEQ ID NO: 18) was used as the template.

Figure 3:
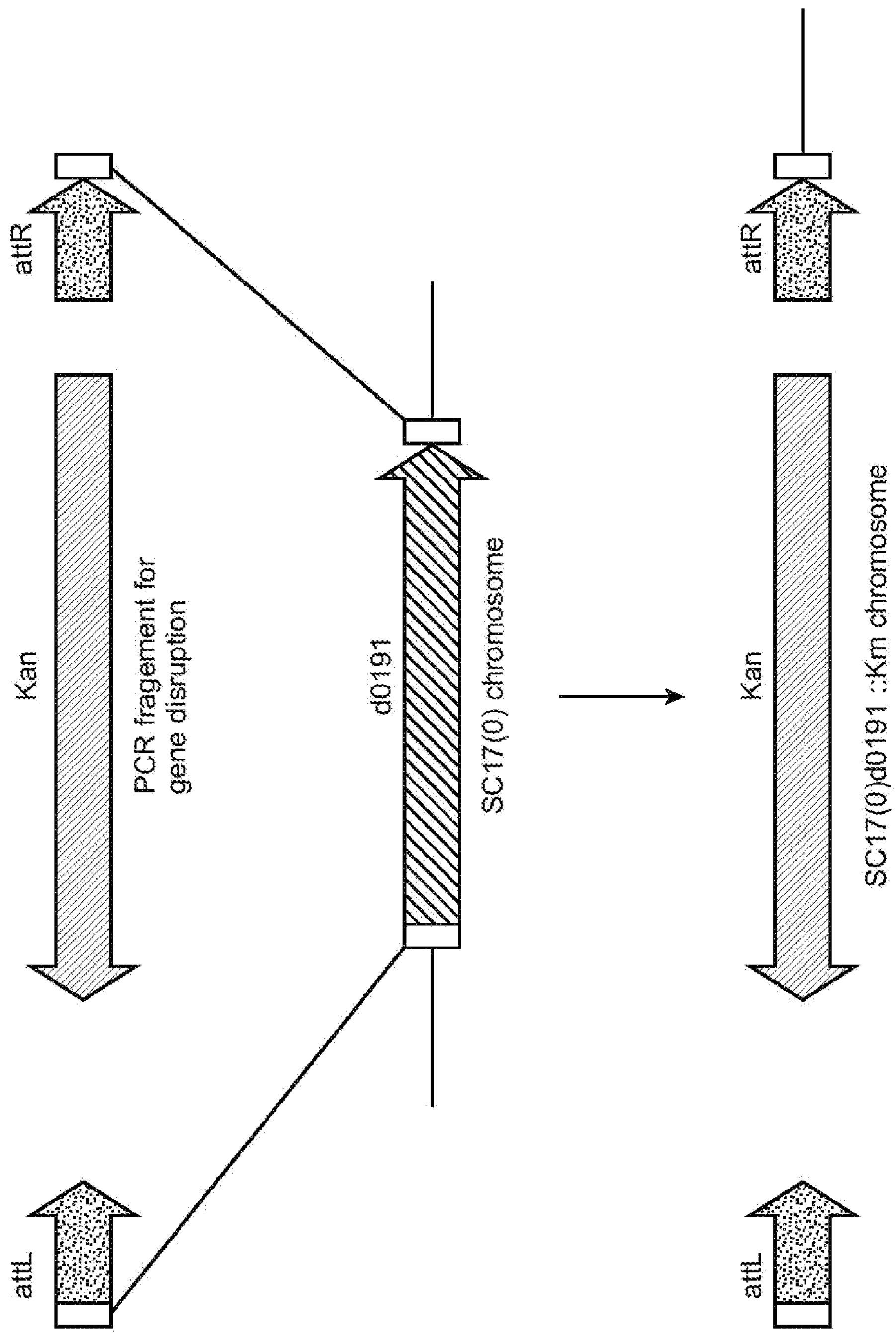
FIG. 3 shows the scheme of the deletion of the d0191 gene.

For PCR, Pyrobest polymerase (Takara) was used, and after a reaction at 94° C. for 5 minutes, a cycle of 98° C. for 5 seconds, 55° C. for 5 seconds and 72° C. for 2 minute and 30 seconds was repeated 30 times in the standard reaction composition described in the protocol of the polymerase to amplify the target DNA fragment. The obtained DNA fragment (DNA fragment with the kanamycin resistant marker and homologous sequences of d0191 on both sides of the marker, FIG. 3) was introduced into *P. ananatis* SC17(0)/RSF-Red-TER strain by electroporation to obtain a kanamycin-resistant strain. It was confirmed that the kanamycin-resistant strain contained a d0191 gene which had been disrupted by insertion of the kanamycin-resistant cassette into the d0191 gene on the chromosome with the homologous sequences of the d0191 gene region present at both ends of the DNA fragment (SC17(0) d0191::$Km^r$ strain, FIG. 3).

Then, by introducing the chromosomal DNA prepared from this SC17(0) d0191::$Km^r$ strain into the SC17 strain by electroporation, a SC17 d0191::$Km^r$ strain, which was a d0191 gene-disrupted strain derived from the SC17 strain, was finally obtained.

(5) Construction of Plasmid Carrying Inhibition-Desensitized Type SAT (Serine Acetyltransferase) Gene (pMIV-CysE5)

It is known that the pMIV-CysE5 plasmid includes the cysE5 gene encoding a mutant SAT which is desensitized to feedback inhibition (U.S. Patent Published Application No. 20050112731(A1)), and a cysteine-producing bacterium which produces a marked amount of cysteine can be prepared by introducing this plasmid (U.S. Patent Published Application No. 20050112731(A1), U.S. Pat. No. 5,972,663 etc.). The construction method of pMIV-CysE5 is described below.

The mutant allele *E. coli* cysE gene, cysE5 (U.S. Patent Published Application No. 20050112731(A1)) was obtained by PCR using a cysEplF primer (5'-agc-tga-gtc-gac-atg-tcg-tgt-gaa-gaa-ctg-gaa-3', SEQ ID NO: 20), a cysER primer (5'-agc-tga-tct-aga-ata-gat-gat-tac-atc-gca-tcc-3', SEQ ID NO: 21) and the template pMW-PompC-cysE5 (EP1650296A1) (a cycle of 94° C. for 0.5 minute, 57° C. for 0.5 minute and 72° C. for 1 minute was repeated 27 times, and then the reaction was allowed to stand at 72° C. for 7 minutes). The cysEplF primer was designed so as to bind with the start codon ATG and a downstream sequence of the *E. coli* cysE gene, and had a 6-mer SalI site at the 5' end. The cysER primer was designed so as to bind with the stop codon and an upstream sequence of the *E. coli* cysE gene, and had a 6-mer XbaI site at the 5' end. A DNA fragment of about 0.7 kb obtained by PCR was digested with SalI and XbaI, and the digestion product was inserted into pMIV-PompC which had been similarly digested with SalI and XbaI to construct pMIV-CysE5.

Figure 4:
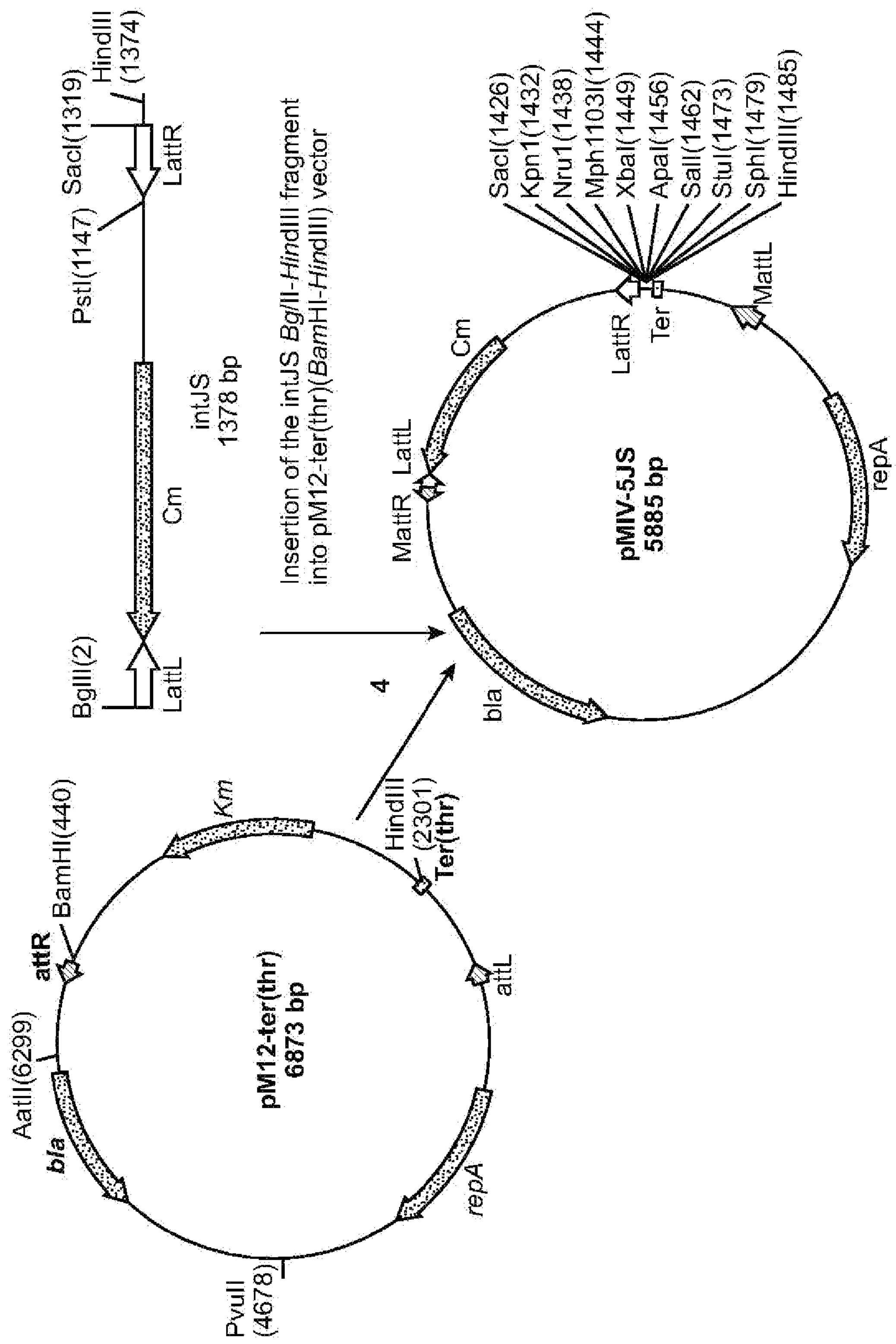
FIG. 4 shows the construction of the pMIV-5JS plasmid.

The pMIV-PompC plasmid described above was constructed as follows. By PCR using the genomic DNA of *E. coli* MG1655 strain as the template, a PrOMPCF primer (5'-agc-tga-gtc-gac-aac-cct-ctg-tta-tat-gcc-ttt-a-3', SEQ ID NO: 22), and a PrOMPCR primer (5'-agc-tga-gca-tgc-gag-tga-agg-ttt-tgt-ttt-gac-3', SEQ ID NO: 23), a DNA fragment containing about 0.3 kb of the promoter region of the ompC gene was obtained, and this fragment was inserted into pMIV-5JS at the PaeI and SalI sites to construct pMIV-PompC. The pMIV-5JS plasmid was constructed by ligating the BamHI and HindIII sites designed beforehand at both ends of the intJS cassette (described later) with the BglII and HindIII sites of pM12-ter(thr) (described later) (FIG. 4).

Figure 5:
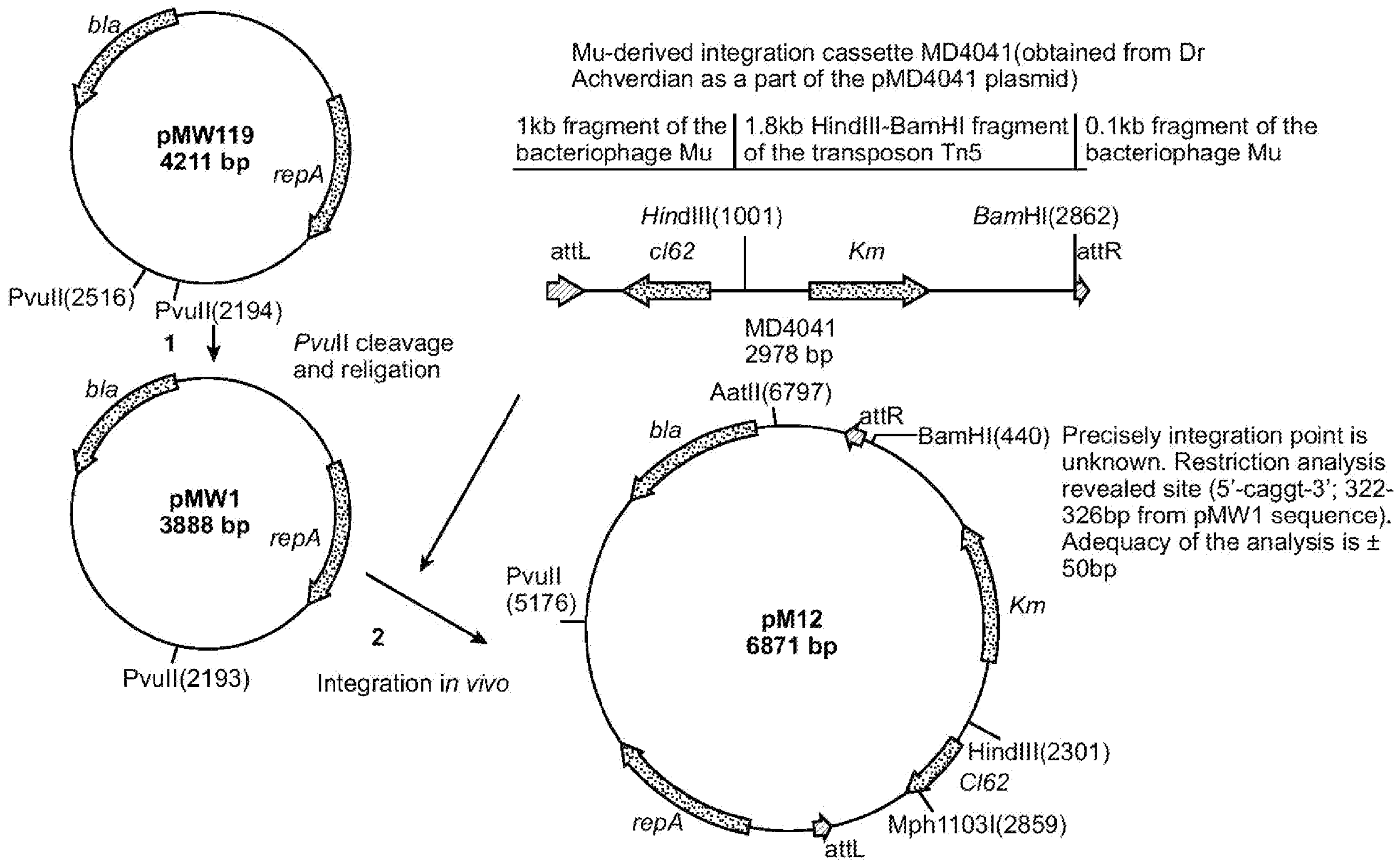
FIG. 5 shows the construction of pM12.
Figure 6:
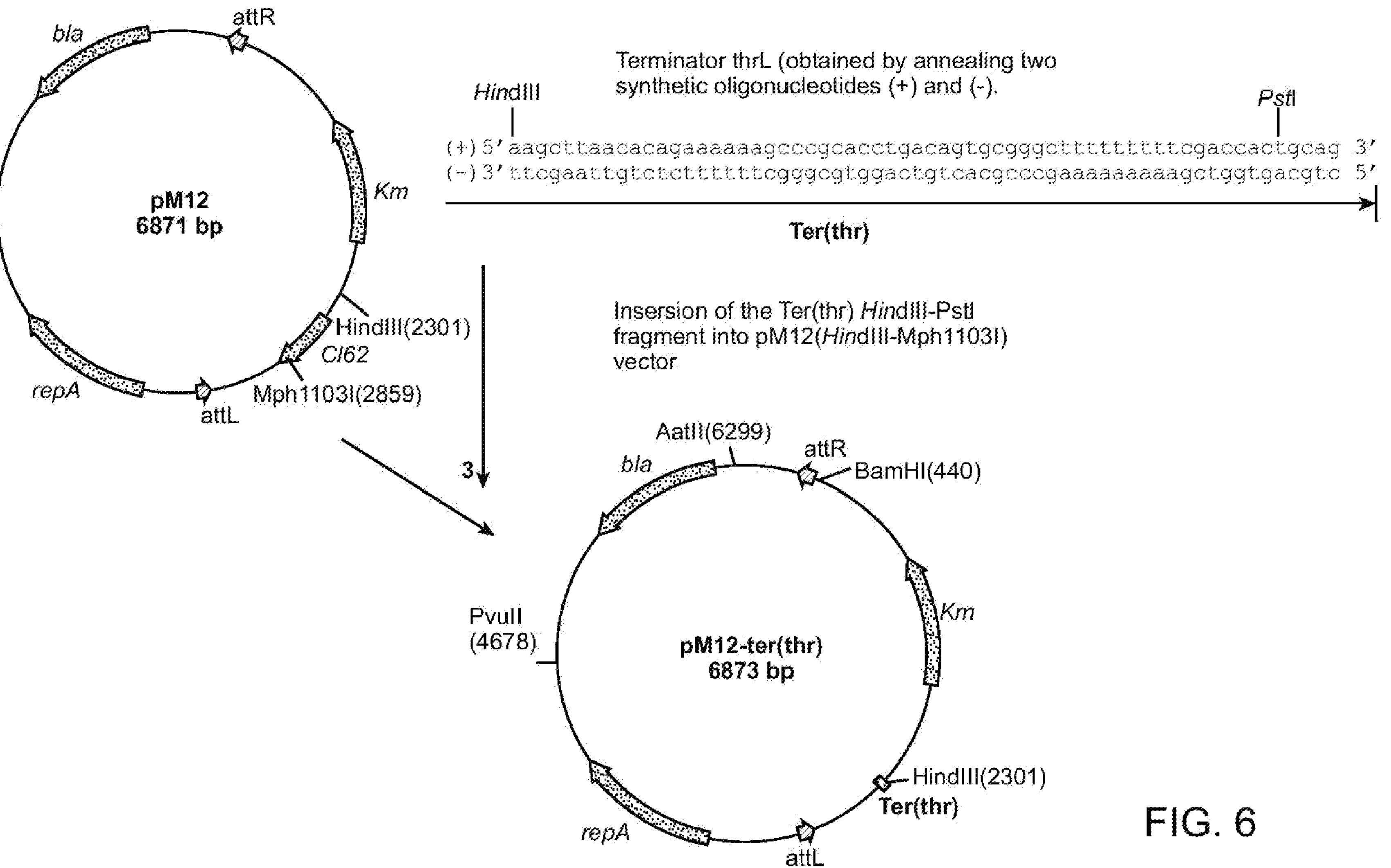
FIG. 6 shows the construction of the pM12-ter(thr) plasmid. The sequences in the drawing are shown as SEQ ID NOS: 24 and 25.
Figure 7:
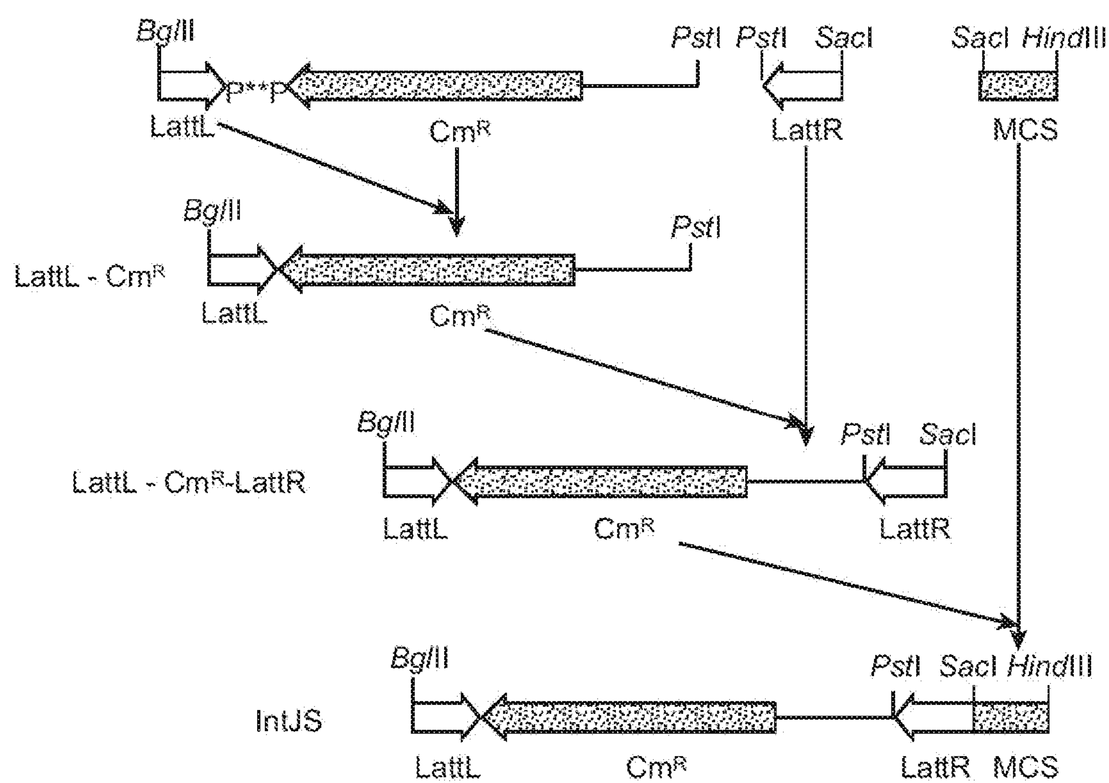
FIG. 7 shows the construction of the IntJS cassette.

The pM12-ter(thr) plasmid was constructed (FIG. 6) by inserting a double strand DNA fragment (thrL terminator, designed to have HindIII and PstI sites at both ends) produced by annealing a synthetic oligonucleotide (aagcttaaca cagaaaaaag cccgcacctg acagtgcggg cttttttttt cgaccactgc ag, SEQ ID NO: 24) and a complementary synthetic oligonucleotide (ttcgaattgt gtcttttttc gggcgtggac tgtcacgccc gaaaaaaaaa gctggtgacg tc, SEQ ID NO: 25) into pM12 which contains the integration cassette derived from Mu phage (EP1486570 (A1), FIG. 5) at the HindIII and Mphl 103I sites. The IntJS cassette was constructed by the following procedures (a) to (g) (FIG. 7).

(a) By PCR using an upstream primer (ccagatcttg aagcctgctt ttttatacta agttggc, SEQ ID NO: 26, designed to have BglII site), a downstream primer (gaaatcaaat aatgatttta ttttg, SEQ ID NO: 27, phosphorylated) and the pMW118-attL-tet-attR-ter_rrnB plasmid (WO2005/010175) as the template, a LattL fragment of 0.12 kbp was obtained.

(b) By PCR using an upstream primer (ttacgccccg ccctgccact catcgc, SEQ ID NO: 28, phosphorylated), a downstream primer (gtcactgcag ctgatgtccg gcggtgcttt tgcc, SEQ ID NO: 29, designed to have PstI site) and the pACYC184 plasmid (New England Biolabs) as the template, a $Cm^R$ fragment of 1.03 kbp was obtained.

(c) By PCR using an upstream primer (cagctgcagt ctgttacagg tcactaatac c, SEQ ID NO: 30, designed to have PstI site), a downstream primer (ccgagctccg ctcaagttag tataaaaaag ctgaacg, SEQ ID NO: 31, designed to have SacI site), and pMW118-attL-tet-attR-ter_rrnB (WO2005/010175) as the template, an LattR fragment of 0.16 kbp was obtained.

(d) By ligation of the LattL fragment and the $Cm^R$ fragment, a LattL-$Cm^R$ fragment of 1.15 kbp was obtained.

(e) By ligation of the LattL-$Cm^R$ fragment and the LattR fragment digested with PstI, a LattL-CmR-LattR fragment of 1.31 kbp was obtained.

(f) By annealing a synthetic oligonucleotide (cccgagctcg gtacctcgcg aatgcatcta gatgggcccg tcgactgcag aggcctgcat gcaagcttcc, SEQ ID NO: 32) and a synthetic oligonucleotide which is a complementary strand of the former, a double strand DNA fragment of 70 bp constituting a multi-cloning site (MCS) was obtained.

(g) By ligation of the LattL-$Cm^R$-LattR fragment and the double strand DNA fragment constituting a multi-cloning site (MCS), both digested with SacI, an IntJS fragment of 1.38 kbp was obtained.

(6) Construction of *P. ananatis* Strain Having Cysteine-Producing Ability and Enhanced d0191 (SC17/pMIV-CysE5/pACYC-d0191F Strain)

The plasmid pACYC-d0191F containing the d0191 gene (kanamycin resistant) constructed as described above was introduced into the SC17 strain (SC17/pACYC-d0191F), and the an inhibition-desensitized SAT gene-carrying plasmid pMIV-CysE5 (chloramphenicol resistant) was further introduced into the strain to construct a *P. ananatis* strain having cysteine-producing ability and enhanced d0191 (SC17/pMIV-CysE5/pACYC-d0191F strain). Furthermore, as a control strain, SC17/pMIV-CysE5/pACYC177 was prepared, which was transformed with the empty vector pACYC177 instead of pACYC-d0191F.

(7) Construction of *P. ananatis* Strain Having Cysteine-Producing Ability and Deficient in d0191 (SC17 d0191::$Km^r$/pMIV-CysE5 Strain).

The d0191-deficient strain, SC17 d0191::$Km^r$ strain, constructed as described above was transformed with the pMIV-CysE5 plasmid to prepare a d0191-deficient cysteine-producing bacterium, SC17 d0191::$Km^r$/pMIV-CysE5. As a control strain, an SC17/pMIV-CysE5 strain was prepared, which corresponded to the SC17 strain introduced with pMIV-CysE5.

(8) Effect of Deletion of d0191 and Enhancement of d0191 on Cysteine Resistance in *P. ananatis* SC17 Strain In order to investigate influence of the d0191 gene on cysteine resistance, the d0191-deficient strain, SC17 d0191::$Km^r$ strain, and the d0191-amplified strain, SC17/pSTV-d0191F strain, as well as the respective control strains, the SC17 strain and the SC17/pSTV29 strain, respectively, were each cultured in M9 minimal medium (Sambrook et al., Molecular Cloning, 3rd edition, 2001, Cold Spring Harbor Laboratory Press) containing cysteine of different concentrations, and the difference in cysteine resistance was evaluated by determining any increase in growth. In this culture, as the resistance to cysteine increased, the OD of the medium increased more quickly, and as the resistance to cysteine decreased, the OD of the medium increased at a much slower rate. The procedure of the experiment was as follows. Each strain was precultured overnight in M9 minimal medium containing 0.4% glucose (not containing cysteine) (3-ml test tube, 34° C., shaking culture), and then inoculated into the main culture medium. At the time of the inoculation, the OD of the preculture was measured, and the inoculation amount was adjusted so that the main culture is started with the same amounts of cells. The OD at the time of the start of the main culture was about 0.007.

Figure 8:
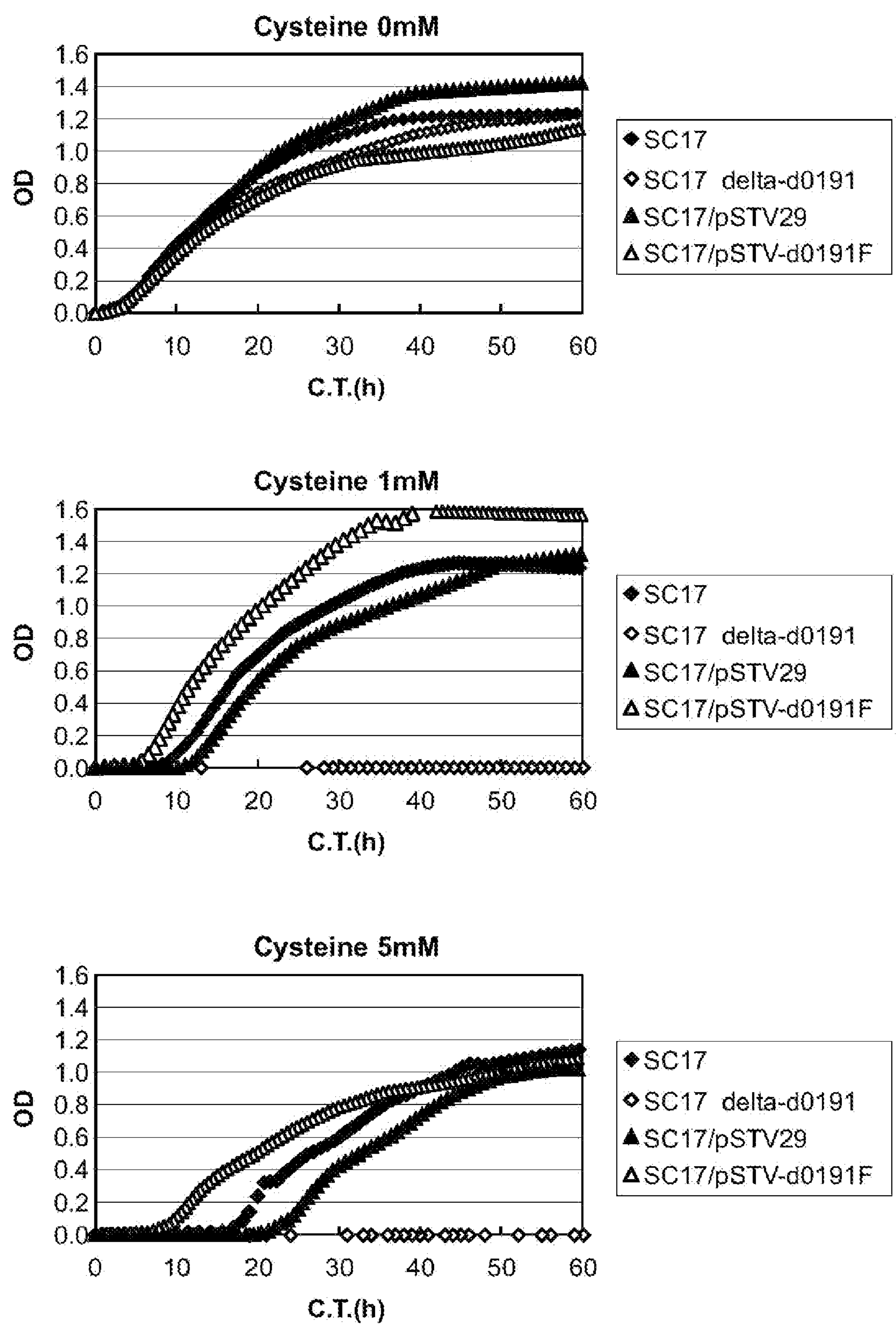
FIG. 8 shows the growth of a d0191-deficient strain and a d0191-enhanced strain of *P. ananatis* in the presence of L-cysteine.

The main culture was performed in 4 ml of the M9 minimal medium containing cysteine at one of various concentrations (0 mM, 1 mM, 5 mM) and 0.4% glucose using an automatically OD measuring culture apparatus, BIO-PHOTORECORDER TN-1506 (ADVANTEC) and the L-shaped test tube for the apparatus. 25 mg/L of chloramphenicol was added to the medium for the strains containing the plasmid. Progress of the culture (growth curves) are shown in FIG. 8. There was observed a tendency that as the concentration of cysteine increased, the increase of the OD was slower. However, the d0191-enhanced strain, SC17/pSTV-d0191F strain grew more quickly as compared to the control SC17/pSTV29 strain, and it was found that it was imparted with cysteine resistance. Furthermore, since growth of the d0191-deficient strain, SC17 d0191::$Km^r$, was completely inhibited by addition of cysteine, it was found that the cysteine resistance thereof decreased.

(9) Effect of Enhancing d0191 on Cysteine Production in *E. coli* MG1655 Strain

Figure 9:
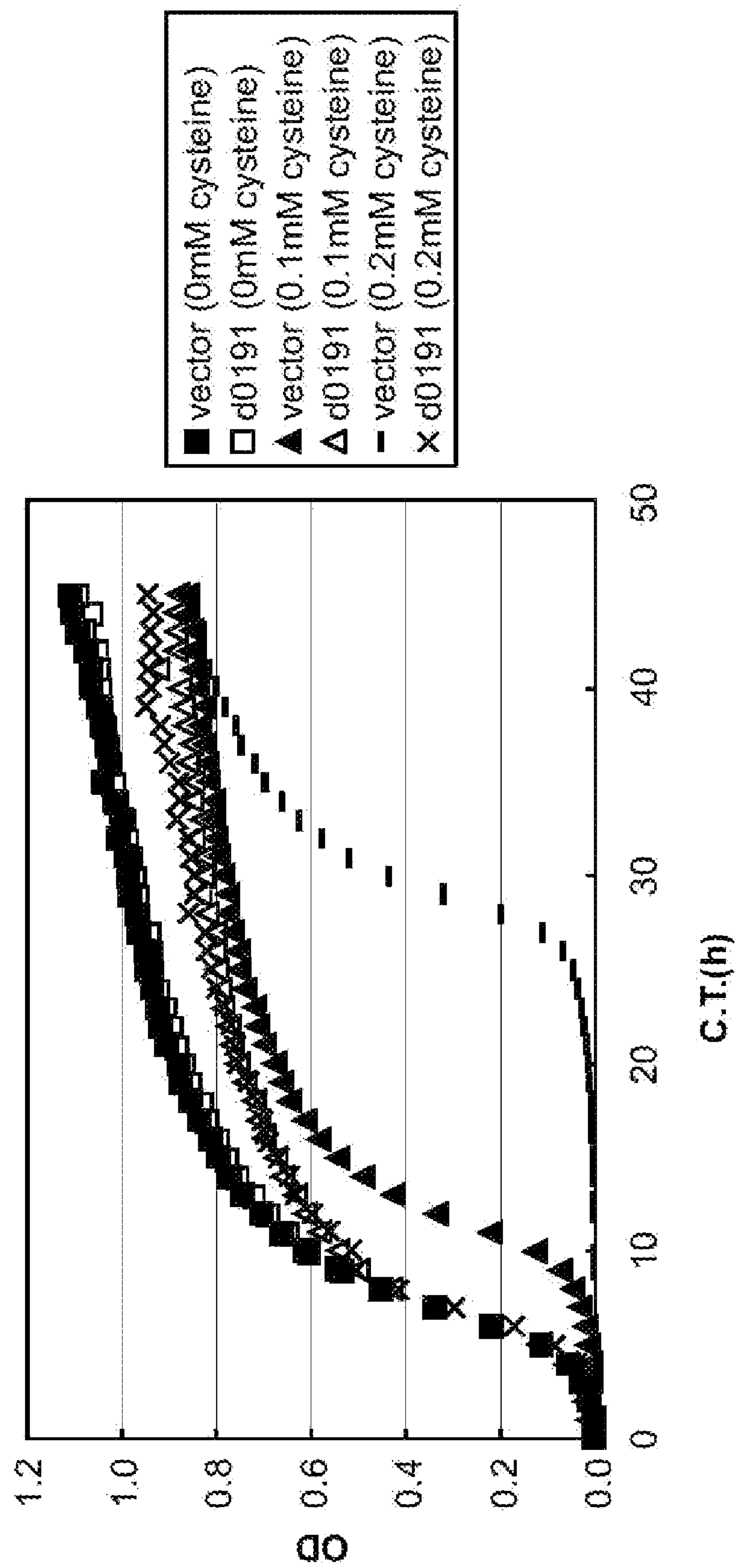
FIG. 9 shows the growth of a d0191-enhanced strain and a d0191-non-enhanced strain of *E. coli* in the presence of L-cysteine.

In order to investigate effect of enhancing the d0191 gene on cysteine resistance, the cysteine-producing abilities of the d0191-amplified strain, MG1655/pSTV-d0191F, a control strain thereof, MG1655/pSTV29, were each cultured in the M9 minimal medium containing cysteine at different concentrations, and difference in cysteine resistance was evaluated by determining rising of the growth. The culture was performed basically according to the method described in (8), except that the OD at the start of the main culture was about 0.006, the culture temperature was 37° C., and the cysteine concentrations were 0 mM, 0.1 mM, 0.2 mM. Progress of the culture (growth curves) is shown in FIG. 9. There was observed a tendency that as the concentration of cysteine increased, the increase in the OD was slower. However, the d0191-enhanced strain, MG1655/pSTV-d0191F strain grew more quickly compared with the control MG1655/pSTV29 strain, and it was found that it was imparted with cysteine resistance. From the above results, it was found that when d0191 was enhanced, cysteine resistance was enhanced regardless of whether the host is *P. ananatis* or *E. coli*.

(10) Detection of Cysteine Desulfhydrase Activity of d0191 Product by Activity Staining The phenotype concerning cysteine resistance suggested a possibility of involvement of the d0191 product in cysteine decomposition. Therefore, in order to examine whether the d0191 gene product had cysteine desulfhydrase activity (henceforth abbreviated as the "CD activity") indicative of cysteine decomposition, a d0191-deficient strain, a d0191-enhanced strain and their respective control strains were cultured, proteins in cell extracts of them were separated by native PAGE, and their CD activity was detected by activity staining. The methods of native PAGE and activity staining were according to the descriptions of N. Awano et al. (Effect of cysteine desulfhydrase gene disruption on L-cysteine overproduction in *Escherichia coli*, Appl. Microbiol. Biotechnol., 2003 August; 62(2-3):239-43).

First, the four strains, the d0191-deficient strain SC17 d0191::$Km^r$ strain constructed as described above and its control, the SC17 strain, as well as the d0191-enhanced strain SC17/pHSG-d0191F strain and its control, SC17/pHSG299, were cultured by the method described below, and cell extracts of each were prepared. An overnight culture in LB medium (5 g/L of yeast extract, 10 g/L of tryptone, 10 g/L of sodium chloride) for each strain was inoculated into 50 ml of LB medium contained in a Sakaguchi flask so as to be diluted 100 times, and culture was performed with shaking. After 3 hours, cells in the logarithmic phase were collected from the medium (OD was around 0.5), washed with a washing buffer (10 mM Tris-HCl (pH 8.6), 0.1 mM DTT (dithiothreitol), 0.01 mM PLP (pyridoxal-5'-phosphate)), then suspended in 1 ml of the washing buffer, and disrupted by ultrasonication, and the supernatant (cell extract) was obtained by centrifugation. The culture was performed at 34° C. for all the strains, and 20 mg/L of kanamycin was added to the medium for the strains containing a plasmid. Protein concentration of each cell extract prepared as described above was quantified, and the extract was diluted to a protein concentration of 2.5 mg/ml with the washing buffer, and 5× loading buffer was added (10 mM Tris-HCl (pH 8.6), 30% glycerol, 0.005% BPB (Bromophenol Blue)) to prepare a sample at a final concentration of 2 mg/ml.

Figure 10:
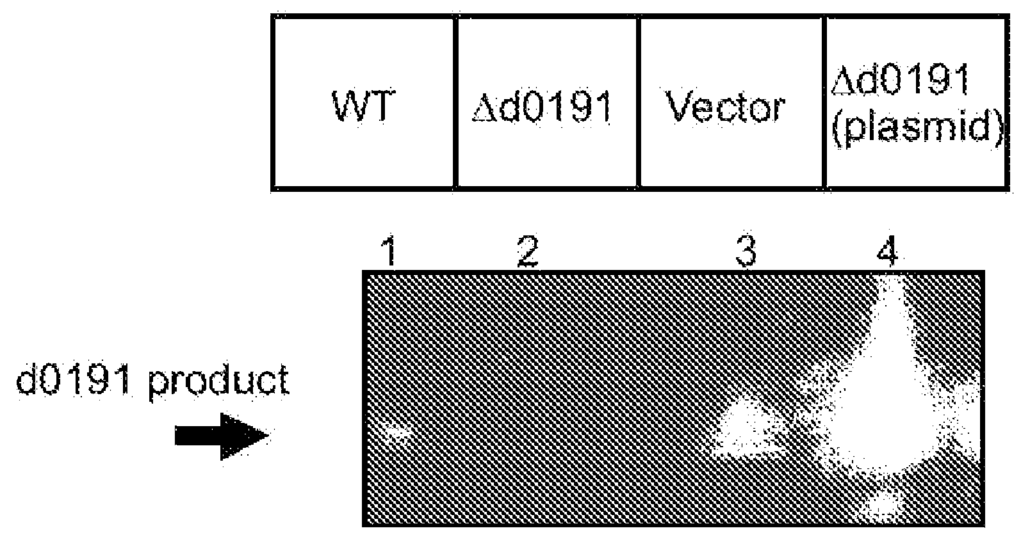
FIG. 10 shows results of cysteine desulfhydrase activity staining of d0191 product.

One microliter (2 μg of protein) of each sample was loaded onto a 10% native PAGE gel (TEFCO), and native PAGE was performed at 4° C. and 20 mA for 1.5 hours. The composition of the gel-running buffer used in the native PAGE consisted of 25 mM Tris-HCl (pH 8.3) and 192 mM glycine. After the electrophoresis, the gel was immersed in a staining solution (100 mM Tris-HCl (pH 8.6), 10 mM EDTA (ethylenediaminetetraacetic acid), 50 mM L-cysteine, 0.02 mM PLP, 1.6 mM bismuth(III) chloride), and activity staining was performed at room temperature by slowly shaking the gel until the appropriate coloring was observed. The detected bands of the d0191 product presented by the CD activity are shown in FIG. 10. A band not seen with the d0191-deficient strain was observed with the control strain, and increased intensity of this band was observed with the d0191-enhanced strain. From these results, it was shown that a band of the d0191 product stained by the CD activity. From the above results, it was revealed that d0191 coded for a novel cysteine desulfhydrase, and was involved in cysteine resistance.

(11) Effect of d0191 Enhancement on Cysteine Production in Cysteine-Producing Bacterium In order to investigate the effect of enhancing the d0191 gene on cysteine production, the cysteine-producing abilities of the cysteine-producing bacterium, *P. ananatis* SC17/pMIV-CysE5/pACYC-d0191F, in which d0191 is enhanced, and the control SC17/pMIV-CysE5/pACYC177 strain were compared. For the culture, a cysteine production medium (composition: 15 g/L of ammonium sulfate, 1.5 g/L of potassium dihydrogenphosphate, 1 g/L of magnesium sulfate heptahydrate, 0.1 mg/L of thiamine hydrochloride, 1.7 mg/L of ferrous sulfate heptahydrate, 0.15 mg/L of sodium molybdate dihydrate, 0.7 mg/L of cobalt chloride hexahydrate, 1.6 mg/L of manganese chloride tetrahydrate, 0.3 mg/L of zinc sulfate heptahydrate, 0.25 mg/L of copper sulfate pentahydrate, 0.6 g/L of tryptone, 0.3 g/L of yeast extract, 0.6 g/L of sodium chloride, 20 g/L of calcium carbonate, 135 mg/L of L-histidine monohydrochloride monohydrate, 4 g/L of sodium thiosulfate, 2 mg/L of pyridoxine hydrochloride, 60 g/L of glucose, 25 mg/L of chloramphenicol and 20 mg/L of kanamycin) was used.

The culture was performed according to the following procedures. The SC17/pMIV-CysE5/pACYC-d0191F and the SC17/pMIV-CysE5/pACYC177 strains were each applied and spread onto LB agar medium containing chloramphenicol and kanamycin, and precultured overnight at 34° C. The cells corresponding to about 7 cm on the plate were scraped with an inoculating loop of 10 μl size (NUNC Blue Loop), and inoculated into 2 ml of the cysteine production medium in a large test tube (internal diameter: 23 mm, length: 20 cm). The amounts of inoculated cells were adjusted so that the cell amounts at the time of the start of the culture were substantially the same. The culture was performed at 32° C. with shaking. For both strains, when glucose was completely consumed, the culture was ended (about 22 to 25 hours), and the amount of cysteine which accumulated in the medium was quantified. The quantification of cysteine was performed by the method described by Gaitonde, M. K. (Biochem. J., 1967 Aug., 104(2):627-33). The experiment was performed in tetraplicate for the both strains, and averages and standard deviations of the accumulated cysteine amounts are shown in Table 1. As shown in Table 1, it was revealed that enhancement of d0191 had the effect of decreasing cysteine accumulation amount.

TABLE 1

| Strain | Gene type | Cys (mg/L) |
|---|---|---|
| SC17/pMIV-CysE5/pACYC177 | Vector | 169.5 ± 3.7 |
| SC17/pMIV-CysE5/pACYC-d0191F | d0191 (plasmid) | 71.3 ± 4.6 |

(9) Effect of d0191 Deficiency on Cysteine-Producing Ability in Cysteine-Producing Bacterium Since it became clear that d0191 participates in decomposition of cysteine, and enhancing the gene reduced cysteine production, it was examined whether suppression of the activity of d0191 (specifically, deficiency of the gene) had a positive effect on the cysteine production. In order to examine whether the d0191-deficient cysteine-producing strain, SC17 d0191::Km$^r$/pMIV-CysE5, prepared as described above had superior cysteine production ability as compared to the d0191-non-disrupted strain, SC17/pMIV-CysE5, they were cultured for cysteine production, and the abilities thereof were compared. The methods for the cysteine production culture and quantification of cysteine were the same as those described in (11), provided that, as for the antibiotics, only chloramphenicol was added to the medium. The experiment was performed in tetraplicate for the control strain, and in octaplicate for the d0191-deficient strain. Averages and standard deviations of the accumulated cysteine amounts are shown in Table 2. As shown in Table 2, it was revealed that suppression of the activity of d0191 had an effect of increasing accumulation amount of cysteine.

TABLE 2

| Strain | Gene type | Cys (mg/L) |
|---|---|---|
| SC17/pMIV-CysE5 | Vector | 202 ± 14 |
| SC17 d0191::Km$^r$/pMIV-CysE5 | Δd0191 | 516 ± 46 |

Explanation of Sequence Listing:

SEQ ID NO: 1: Nucleotide sequence of *P. ananatis* d0191 gene

SEQ ID NO: 2: Amino acid sequence of *P. ananatis* D0191

SEQ ID NO: 3: Nucleotide sequence of *P. ananatis* hisD gene

SEQ ID NOS: 4 to 32: PCR primers

SEQ ID NO: 33: Nucleotide sequence of *Citrobacter koseri* d0191 gene

SEQ ID NO: 34: Amino acid sequence of *Citrobacter koseri* D0191

SEQ ID NO: 35: Nucleotide sequence of *Klebsiella pneumoniae* d0191 gene

SEQ ID NO: 36: Amino acid sequence of *Klebsiella pneumoniae* D0191

SEQ ID NO: 37: Nucleotide sequence of *Enterobacter* sp. 638 d0191 gene

SEQ ID NO: 38: Amino acid sequence of *Enterobacter* sp. 638 D0191

SEQ ID NO: 39: Nucleotide sequence of *Salmonella typhimurium* d0191 gene

SEQ ID NO: 40: Amino acid sequence of *Salmonella typhimurium* D0191

SEQ ID NO: 41: Nucleotide sequence of *Serratia proteamaculans* d0191 gene

SEQ ID NO: 42: Amino acid sequence of *Serratia* proteamaculans D0191

SEQ ID NO: 43: Nucleotide sequence of *Erwinia carotovora* d0191 gene

SEQ ID NO: 44: Amino acid sequence of *Erwinia carotovora* D0191

SEQ ID NO: 45: Nucleotide sequence of *Vibrio cholerae* d0191 gene

SEQ ID NO: 46: Amino acid sequence of *Vibrio cholerae* D0191

SEQ ID NO: 47: Nucleotide sequence of *Pseudomonas fluorescens* d0191 gene

SEQ ID NO: 48: Amino acid sequence of *Pseudomonas fluorescens* D0191

SEQ ID NO: 49: Nucleotide sequence of *Streptomyces coelicolor* d0191 gene

SEQ ID NO: 50: Amino acid sequence of *Streptomyces coelicolor* D0191

SEQ ID NO: 51: Nucleotide sequence of *Mycobacterium avium* d0191 gene

SEQ ID NO: 52: Amino acid sequence of *Mycobacterium avium* D0191

SEQ ID NO: 53: Primer for attL amplification

SEQ ID NO: 54: Primer for attL amplification

SEQ ID NO: 55: Nucleotide sequence of attL

SEQ ID NO: 56: Primer for attR amplification

SEQ ID NO: 57: Primer for attR amplification

SEQ ID NO: 58: Nucleotide sequence of attR

SEQ ID NO: 59: Primer for amplification of DNA fragment containing bla gene

SEQ ID NO: 60: Primer for amplification of DNA fragment containing bla gene

SEQ ID NO: 61: Primer for amplification of DNA fragment containing ter_rrnB

SEQ ID NO: 62: Primer for amplification of DNA fragment containing ter_rrnB

SEQ ID NO: 63: Nucleotide sequence of the DNA fragment containing ter_thrL terminator SEQ ID NO: 64: Primer for amplification of DNA fragment containing ter_thrL terminator SEQ ID NO: 65: Primer for amplification of DNA fragment containing ter_thrL terminator.

SEQ ID NO: 66: Nucleotide sequence of *P. ananatis* ybaO (c0263) gene

SEQ ID NO: 67: Amino acid sequence of *P. ananatis* YbaO (C0263).

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid selected from the group consisting of L-cysteine, L-cystine, derivatives thereof, and combinations thereof, which comprises culturing a bacterium belonging to the family *Enterobacteriaceae* in a medium and collecting the L-amino acid from the medium, wherein the bacterium has L-cysteine-producing ability and has been modified to decrease the activity of a protein selected from the group consisting of:

(A) a protein comprising the amino acid sequence of SEQ ID NO:2, and (B) a protein comprising the amino acid sequence of SEQ ID NO:2 but which includes substitutions, deletions, insertions, or additions of 1 to 10 amino acid residues, and wherein said protein comprises cysteine desulfhydrase activity.

2. The method according to claim 1, wherein the derivative of L-cysteine is a thiazolidine derivative.

3. The method according to claim 1, wherein the activity of the protein is decreased by a method selected from the group consisting of decreasing the expression of a gene encoding the protein, and by disrupting the gene encoding the protein.

4. The method according to claim 1, wherein the protein is encoded by a gene selected from the group consisting of:

(a) a DNA comprising the nucleotide sequence of SEQ ID NO:1, and (b) a DNA which is able to hybridize with a sequence complementary to the nucleotide sequence of SEQ ID NO:1under stringent conditions comprising washing at 60° C., 0.1×SSC, 0.1% SDS, and encodes a protein comprising cysteine desulfhydrase activity.

5. The method according to claim 1, wherein the bacterium further comprises a serine acetyltransferase which has been mutated so that feedback inhibition by L-cysteine is attenuated.

6. The method according to claim 1, wherein the bacterium is a *Pantoea* bacterium.

7. The method according to claim 6, wherein the bacterium is *Pantoea ananatis*.

* * * * *